(12) United States Patent
Bhimavarapu et al.

(10) Patent No.: US 11,337,872 B2
(45) Date of Patent: May 24, 2022

(54) PATIENT SUPPORT SYSTEMS AND METHODS FOR ASSISTING CAREGIVERS WITH PATIENT CARE

(71) Applicant: Stryker Corporation, Kalamazoo, MI (US)

(72) Inventors: Krishna S. Bhimavarapu, Kalamazoo, MI (US); Annie Desaulniers, Bothell, WA (US); Ming Chen, Ann Arbor, MI (US); Marco Constant, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 122 days.

(21) Appl. No.: 16/020,068

(22) Filed: Jun. 27, 2018

(65) Prior Publication Data
US 2018/0369039 A1 Dec. 27, 2018

Related U.S. Application Data

(60) Provisional application No. 62/525,353, filed on Jun. 27, 2017.

(51) Int. Cl.
*A61G 7/018* (2006.01)
*G06F 3/0482* (2013.01)
(Continued)

(52) U.S. Cl.
CPC ........... *A61G 7/018* (2013.01); *A61G 7/0506* (2013.01); *A61G 7/0507* (2013.01); *A61G 7/10* (2013.01);
(Continued)

(58) Field of Classification Search
CPC .... A61G 7/018; A61G 7/0506; A61G 7/0507; A61G 7/10; A61G 7/001; A61G 7/012;
(Continued)

(56) References Cited

U.S. PATENT DOCUMENTS 5,113,214 A 5/1992 Nagata et al.
5,276,432 A 1/1994 Travis
(Continued)

FOREIGN PATENT DOCUMENTS

CN 101789230 A 7/2010
DE 19505162 C1 3/1996
(Continued)

OTHER PUBLICATIONS

Apple, "Adjust the Brightness on you iPhone, IPad, or IPod Touch", https://support.apple.com/en-us/HT202613, 2018, 2 pages.
(Continued)

*Primary Examiner* — Andrew T Chiusano
(74) *Attorney, Agent, or Firm* — Howard & Howard Attorneys PLLC

(57) ABSTRACT

A patient support system for providing customized user menus. The system comprises a patient support apparatus, a user interface configured to receive input from a user, and a display configured to display user menus or information. The user menus may comprise indicia representative of the operational functions of the patient support apparatus. A controller determines the customized user menu based on usage characteristics, a position of the user interface in proximity to the patient support apparatus, a location of the user interface within a facility, an identification of the user, and/or a patient condition. A touchscreen and/or a mobile device may comprise the user interface and the display. The mobile device may be removably coupled to the patient support apparatus. Methods for improving patient care by providing the customized user menu are also disclosed.

10 Claims, 27 Drawing Sheets

(51) Int. Cl.
  *G06F 3/04883* (2022.01)
  *G06F 3/0484* (2022.01)
  *A61G 7/05* (2006.01)
  *A61G 7/10* (2006.01)
  *G16H 40/63* (2018.01)
  *A61G 7/012* (2006.01)
  *A61G 7/053* (2006.01)
  *A61G 7/00* (2006.01)

(52) U.S. Cl.
  CPC .......... *G06F 3/0482* (2013.01); *G06F 3/0484* (2013.01); *G06F 3/04883* (2013.01); *G16H 40/63* (2018.01); *A61G 7/001* (2013.01); *A61G 7/012* (2013.01); *A61G 7/053* (2013.01); *A61G 2203/12* (2013.01); *A61G 2203/16* (2013.01); *A61G 2203/18* (2013.01); *A61G 2203/20* (2013.01); *A61G 2203/70* (2013.01); *A61G 2205/60* (2013.01)

(58) Field of Classification Search
  CPC ................ A61G 7/053; A61G 2203/12; A61G 2203/16; A61G 2203/18; A61G 2203/20; A61G 2203/70; A61G 2203/60; G06F 3/0482; G06F 3/0484; G06F 3/04883; G16H 40/63
  See application file for complete search history.

(56) References Cited

U.S. PATENT DOCUMENTS

| | | | |
|---|---|---|---|
| 5,434,621 | A | 7/1995 | Yu |
| 5,640,953 | A | 6/1997 | Bishop et al. |
| 5,645,667 | A | 7/1997 | Kusen |
| 5,664,270 | A | 9/1997 | Bell et al. |
| 5,971,913 | A | 10/1999 | Newkirk et al. |
| 6,320,510 | B2 | 11/2001 | Menkedick et al. |
| 6,340,977 | B1 | 1/2002 | Lui et al. |
| 6,362,725 | B1 | 3/2002 | Ulrich et al. |
| 6,702,314 | B1 | 3/2004 | Crose |
| 6,876,303 | B2 | 4/2005 | Reeder et al. |
| 6,948,592 | B2 | 9/2005 | Kavounas |
| 7,036,087 | B1 * | 4/2006 | Odom ................ G06F 3/04817 715/779 |
| 7,154,397 | B2 | 12/2006 | Zerhusen et al. |
| 7,296,312 | B2 | 11/2007 | Menkedick et al. |
| 7,319,386 | B2 | 1/2008 | Collins, Jr. et al. |
| 7,336,187 | B2 | 2/2008 | Hubbard, Jr. et al. |
| 7,389,552 | B1 | 6/2008 | Reed et al. |
| 7,443,302 | B2 | 10/2008 | Reeder et al. |
| 7,472,439 | B2 | 1/2009 | Lemire et al. |
| 7,487,562 | B2 | 2/2009 | Frondorf et al. |
| 7,490,021 | B2 | 2/2009 | Holland et al. |
| 7,570,152 | B2 | 8/2009 | Smith et al. |
| 7,690,059 | B2 | 4/2010 | Lemire et al. |
| 7,747,644 | B1 | 6/2010 | Reihl et al. |
| 7,888,901 | B2 | 2/2011 | Larson et al. |
| 7,895,519 | B1 | 2/2011 | Allegrezza et al. |
| 8,069,157 | B2 | 11/2011 | Jam |
| 8,117,701 | B2 | 2/2012 | Bobey et al. |
| 8,121,856 | B2 | 2/2012 | Huster et al. |
| 8,143,846 | B2 | 3/2012 | Herman et al. |
| 8,165,908 | B2 | 4/2012 | Bolle et al. |
| 8,209,608 | B1 | 6/2012 | Linyard et al. |
| 8,266,742 | B2 | 9/2012 | Andrienko |
| 8,308,237 | B2 | 11/2012 | Kunou |
| 8,319,633 | B2 | 11/2012 | Becker et al. |
| 8,334,777 | B2 | 12/2012 | Wilson et al. |
| 8,334,779 | B2 | 12/2012 | Zerhusen et al. |
| 8,341,777 | B2 | 1/2013 | Hensley et al. |
| 8,344,860 | B2 | 1/2013 | Collins, Jr. et al. |
| 8,410,943 | B2 | 4/2013 | Metz et al. |
| 8,413,270 | B2 | 4/2013 | Turner et al. |
| 8,413,271 | B2 | 4/2013 | Blanchard et al. |
| 8,432,287 | B2 | 4/2013 | O'Keefe et al. |
| 8,442,738 | B2 | 5/2013 | Patmore |
| 8,464,380 | B2 | 6/2013 | Bobey et al. |
| 8,525,682 | B2 | 9/2013 | Dixon et al. |
| 8,544,126 | B2 | 10/2013 | Elliott et al. |
| 8,552,880 | B2 | 10/2013 | Kopp et al. |
| 8,604,917 | B2 | 12/2013 | Collins et al. |
| 8,641,301 | B2 | 2/2014 | Yang et al. |
| 8,650,682 | B2 | 2/2014 | Herman |
| 8,674,839 | B2 | 3/2014 | Zerhusen et al. |
| 8,716,941 | B2 | 5/2014 | Kim |
| 8,756,078 | B2 | 6/2014 | Collins, Jr. et al. |
| 8,768,520 | B2 | 7/2014 | Oexman et al. |
| 8,789,102 | B2 | 7/2014 | Pickelsimer et al. |
| 8,847,756 | B2 | 9/2014 | Tallent et al. |
| 8,868,542 | B2 | 10/2014 | Kimball et al. |
| 8,870,812 | B2 | 10/2014 | Alberti et al. |
| 8,896,524 | B2 | 11/2014 | Birnbaum et al. |
| 8,923,994 | B2 | 12/2014 | Laikari et al. |
| 8,924,218 | B2 | 12/2014 | Corpier et al. |
| 8,926,535 | B2 | 1/2015 | Rawls-Meehan |
| 8,984,685 | B2 | 3/2015 | Robertson et al. |
| 9,001,038 | B2 | 4/2015 | Kasahara |
| 9,032,510 | B2 | 5/2015 | Sampathkumaran et al. |
| 9,038,217 | B2 | 5/2015 | Elliot et al. |
| 9,088,282 | B2 | 7/2015 | Holenarsipur et al. |
| 9,126,571 | B2 | 9/2015 | Lemire et al. |
| 9,138,173 | B2 | 9/2015 | Penninger et al. |
| 9,173,792 | B2 | 11/2015 | Goffer |
| 9,204,823 | B2 | 12/2015 | Derenne et al. |
| 9,220,650 | B2 | 12/2015 | Bobey et al. |
| 9,230,421 | B2 | 1/2016 | Reeder et al. |
| 9,233,033 | B2 | 1/2016 | Valentino et al. |
| 9,259,369 | B2 | 2/2016 | Derenne et al. |
| 9,262,876 | B2 | 2/2016 | Wood et al. |
| 9,320,664 | B2 | 4/2016 | Newkirk et al. |
| 9,342,677 | B2 | 5/2016 | Ali et al. |
| 9,381,125 | B2 | 7/2016 | Herbst et al. |
| 9,424,699 | B2 | 8/2016 | Kusens et al. |
| 9,456,938 | B2 | 10/2016 | Blickensderfer et al. |
| 9,463,126 | B2 | 10/2016 | Zerhusen et al. |
| 9,466,163 | B2 | 10/2016 | Kusens et al. |
| 9,486,084 | B2 | 11/2016 | Connell et al. |
| 9,569,591 | B2 | 2/2017 | Vanderpohl, III |
| 9,593,833 | B2 | 3/2017 | McMannon et al. |
| 9,655,798 | B2 | 5/2017 | Zerhusen et al. |
| 9,691,206 | B2 | 6/2017 | Kusens et al. |
| 9,774,991 | B2 | 9/2017 | Kusens |
| 9,814,410 | B2 | 11/2017 | Kostic et al. |
| 9,838,849 | B2 | 12/2017 | Kusens |
| 9,844,275 | B2 | 12/2017 | Nunn et al. |
| 9,849,051 | B2 | 12/2017 | Newkirk et al. |
| 9,858,741 | B2 | 1/2018 | Kusens et al. |
| 9,892,310 | B2 | 2/2018 | Kusens et al. |
| 9,892,311 | B2 | 2/2018 | Kusens et al. |
| 9,916,649 | B1 | 3/2018 | Kusens |
| 9,934,427 | B2 | 4/2018 | Derenne et al. |
| 9,940,810 | B2 | 4/2018 | Derenne et al. |
| 9,984,521 | B1 | 5/2018 | Kusens et al. |
| 9,997,001 | B2 | 6/2018 | Kusens et al. |
| 9,998,857 | B2 | 6/2018 | Kusens |
| 9,999,555 | B2 | 6/2018 | Magill et al. |
| 10,004,654 | B2 | 6/2018 | Zerhusen et al. |
| 10,013,831 | B1 | 7/2018 | Kusens et al. |
| 10,034,979 | B2 | 7/2018 | Bechtel et al. |
| 10,052,249 | B2 | 8/2018 | Elliott et al. |
| 10,090,068 | B2 | 10/2018 | Kusens et al. |
| 10,096,101 | B2 | 10/2018 | Kusens |
| 10,098,796 | B2 | 10/2018 | Valentino et al. |
| 10,109,179 | B2 | 10/2018 | Kusens |
| 10,115,253 | B2 | 10/2018 | Kusens et al. |
| 10,115,254 | B1 | 10/2018 | Kusens et al. |
| 10,121,299 | B2 | 11/2018 | Kusens et al. |
| 10,136,841 | B2 | 11/2018 | Alghazi |
| 10,147,184 | B2 | 12/2018 | Kusens et al. |
| 10,147,256 | B2 | 12/2018 | Kusens et al. |
| 10,172,752 | B2 | 1/2019 | Goffer |
| 10,187,755 | B2 | 1/2019 | Kusens et al. |
| 10,188,569 | B2 | 1/2019 | Elku et al. |

(56) References Cited

U.S. PATENT DOCUMENTS

| | | |
|---|---|---|
| 10,194,278 B1 | 1/2019 | Kusens |
| 10,198,886 B2 | 2/2019 | Kusens et al. |
| 10,210,378 B2 | 2/2019 | Kusens et al. |
| 10,410,500 B2 | 9/2019 | Derenne et al. |
| 2002/0000727 A1 | 1/2002 | Rass et al. |
| 2002/0014951 A1 | 2/2002 | Kramer et al. |
| 2003/0183427 A1 | 10/2003 | Tojo et al. |
| 2004/0083394 A1 | 4/2004 | Brebner et al. |
| 2006/0077186 A1 | 4/2006 | Park et al. |
| 2006/0102392 A1 | 5/2006 | Johnson et al. |
| 2007/0163045 A1 | 7/2007 | Becker et al. |
| 2007/0219950 A1 | 9/2007 | Crawford |
| 2008/0141459 A1 | 6/2008 | Hamberg et al. |
| 2008/0172789 A1* | 7/2008 | Elliot .................. G06F 19/00 5/616 |
| 2008/0235872 A1* | 10/2008 | Newkirk ............ G06F 3/04847 5/600 |
| 2009/0153370 A1 | 6/2009 | Cooper et al. |
| 2009/0275886 A1* | 11/2009 | Blomquist ............ G09G 3/344 604/66 |
| 2010/0039414 A1 | 2/2010 | Bell |
| 2010/0212087 A1 | 8/2010 | Leib et al. |
| 2011/0080421 A1 | 4/2011 | Capener |
| 2011/0162067 A1 | 6/2011 | Shuart et al. |
| 2011/0169653 A1 | 7/2011 | Wang et al. |
| 2011/0258581 A1* | 10/2011 | Hu .................... G06F 3/04817 715/811 |
| 2012/0023670 A1 | 2/2012 | Zerhusen et al. |
| 2012/0089419 A1* | 4/2012 | Uster .................. A61B 5/1115 705/3 |
| 2012/0137436 A1 | 6/2012 | Andrienko |
| 2012/0215360 A1 | 8/2012 | Zerhusen et al. |
| 2012/0239173 A1 | 9/2012 | Laikari et al. |
| 2013/0138452 A1 | 5/2013 | Cork et al. |
| 2013/0142367 A1 | 6/2013 | Berry et al. |
| 2013/0227787 A1 | 9/2013 | Herbst et al. |
| 2013/0238991 A1 | 9/2013 | Jung et al. |
| 2013/0300867 A1 | 11/2013 | Yoder |
| 2013/0318716 A1 | 12/2013 | Vanderpohl, III |
| 2014/0076644 A1 | 3/2014 | Derenne et al. |
| 2014/0080413 A1 | 3/2014 | Hayes et al. |
| 2014/0259410 A1 | 9/2014 | Zerhusen et al. |
| 2014/0265181 A1 | 9/2014 | Lambarth et al. |
| 2014/0297327 A1 | 10/2014 | Heil et al. |
| 2014/0313700 A1 | 10/2014 | Connell et al. |
| 2014/0342330 A1 | 11/2014 | Freeman et al. |
| 2015/0002393 A1 | 1/2015 | Cohen et al. |
| 2015/0060162 A1 | 3/2015 | Goffer |
| 2015/0077534 A1 | 3/2015 | Derenne et al. |
| 2015/0082242 A1* | 3/2015 | Antipa .................. G06F 3/0482 715/811 |
| 2015/0109442 A1 | 4/2015 | Derenne et al. |
| 2015/0154002 A1 | 6/2015 | Weinstein et al. |
| 2015/0195179 A1* | 7/2015 | Skare .................. G06F 3/0482 715/745 |
| 2015/0213214 A1* | 7/2015 | Patak .................. G16H 40/63 715/727 |
| 2015/0250669 A1 | 9/2015 | Elliott et al. |
| 2015/0257952 A1* | 9/2015 | Zerhusen ............ A61G 7/001 340/12.5 |
| 2015/0317068 A1 | 11/2015 | Marka et al. |
| 2016/0012218 A1 | 1/2016 | Pema et al. |
| 2016/0022039 A1 | 1/2016 | Paul et al. |
| 2016/0038361 A1 | 2/2016 | Bhimavarapu et al. |
| 2016/0045382 A1 | 2/2016 | Goffer |
| 2016/0049028 A1 | 2/2016 | Kusens et al. |
| 2016/0050217 A1 | 2/2016 | Mare et al. |
| 2016/0065909 A1 | 3/2016 | Derenne et al. |
| 2016/0095774 A1 | 4/2016 | Bobey et al. |
| 2016/0098676 A1 | 4/2016 | Kusens et al. |
| 2016/0140307 A1 | 5/2016 | Brosnan et al. |
| 2016/0180668 A1 | 6/2016 | Kusens et al. |
| 2016/0183864 A1 | 6/2016 | Kusens et al. |
| 2016/0193095 A1 | 7/2016 | Roussy et al. |
| 2016/0199240 A1 | 7/2016 | Newkirk et al. |
| 2016/0247342 A1 | 8/2016 | Kusens et al. |
| 2016/0296396 A1 | 10/2016 | Kolar et al. |
| 2016/0320924 A1* | 11/2016 | Mizuguchi ............ A61H 9/0078 |
| 2016/0324705 A1 | 11/2016 | Bach Castillo |
| 2016/0338891 A1 | 11/2016 | Agdeppa et al. |
| 2016/0366327 A1 | 12/2016 | Kusens |
| 2016/0367420 A1 | 12/2016 | Zerhusen et al. |
| 2016/0371786 A1 | 12/2016 | Kusens et al. |
| 2017/0027789 A1 | 2/2017 | St.John et al. |
| 2017/0049642 A9 | 2/2017 | Valentino et al. |
| 2017/0055113 A1 | 2/2017 | Kusens |
| 2017/0076526 A1 | 3/2017 | Kusens et al. |
| 2017/0094477 A1 | 3/2017 | Kusens et al. |
| 2017/0097800 A1 | 4/2017 | Vanderpohl, III |
| 2017/0098048 A1 | 4/2017 | Brosnan et al. |
| 2017/0109770 A1 | 4/2017 | Kusens et al. |
| 2017/0111770 A1 | 4/2017 | Kusens |
| 2017/0116790 A1 | 4/2017 | Kusens et al. |
| 2017/0124844 A1 | 5/2017 | Huster et al. |
| 2017/0128296 A1 | 5/2017 | Kostic et al. |
| 2017/0143565 A1* | 5/2017 | Childs .................. A61G 7/018 |
| 2017/0193177 A1 | 7/2017 | Kusens |
| 2017/0193180 A1 | 7/2017 | Kusens et al. |
| 2017/0193279 A1 | 7/2017 | Kusens et al. |
| 2017/0193772 A1 | 7/2017 | Kusens et al. |
| 2017/0195637 A1 | 7/2017 | Kusens et al. |
| 2017/0213445 A1 | 7/2017 | Kusens |
| 2017/0224562 A1 | 8/2017 | Zerhusen et al. |
| 2017/0229009 A1 | 8/2017 | Foster et al. |
| 2017/0259811 A1 | 9/2017 | Coulter et al. |
| 2017/0281440 A1 | 10/2017 | Puvogel et al. |
| 2017/0352212 A1 | 12/2017 | Kusens et al. |
| 2018/0017945 A1 | 1/2018 | Sidhu et al. |
| 2018/0039743 A1 | 2/2018 | Dixon et al. |
| 2018/0040091 A1 | 2/2018 | Kusens |
| 2018/0041864 A1 | 2/2018 | Kusens |
| 2018/0055418 A1 | 3/2018 | Kostic et al. |
| 2018/0056985 A1 | 3/2018 | Coulter et al. |
| 2018/0084390 A1 | 3/2018 | Kusens |
| 2018/0096550 A1 | 4/2018 | Kusens et al. |
| 2018/0110445 A1 | 4/2018 | Bhimavarapu et al. |
| 2018/0114053 A1 | 4/2018 | Kusens et al. |
| 2018/0137340 A1 | 5/2018 | Kusens et al. |
| 2018/0151010 A1 | 5/2018 | Kusens et al. |
| 2018/0161225 A1 | 6/2018 | Zerhusen et al. |
| 2018/0167816 A1 | 6/2018 | Kusens et al. |
| 2018/0184984 A1 | 7/2018 | Zerhusen et al. |
| 2018/0189946 A1 | 7/2018 | Kusens et al. |
| 2018/0211464 A1 | 7/2018 | Kusens et al. |
| 2018/0218489 A1 | 8/2018 | Kusens |
| 2018/0232979 A1 | 8/2018 | Kusens et al. |
| 2018/0232980 A1 | 8/2018 | Kusens et al. |
| 2018/0247476 A1 | 8/2018 | Kusens et al. |
| 2018/0250177 A1 | 9/2018 | Magill et al. |
| 2018/0271286 A1 | 9/2018 | Jacobs et al. |
| 2018/0271287 A1 | 9/2018 | Jacobs et al. |
| 2018/0279075 A1 | 9/2018 | Kusens |
| 2018/0293826 A1 | 10/2018 | Kusens et al. |
| 2018/0300977 A1 | 10/2018 | Kusens et al. |
| 2018/0303687 A1 | 10/2018 | Moreno et al. |
| 2018/0369035 A1 | 12/2018 | Bhimavarapu et al. |
| 2018/0369039 A1 | 12/2018 | Bhimavarapu et al. |
| 2018/0376300 A1 | 12/2018 | Kusens et al. |
| 2019/0006046 A1 | 1/2019 | Kusens et al. |
| 2019/0008708 A1 | 1/2019 | Moreno et al. |
| 2019/0019283 A1 | 1/2019 | Kusens |
| 2019/0024882 A1 | 1/2019 | Jonsson et al. |
| 2019/0043192 A1 | 2/2019 | Kusens et al. |
| 2019/0046373 A1 | 2/2019 | Coulter et al. |
| 2019/0073849 A1 | 3/2019 | Kusens et al. |

FOREIGN PATENT DOCUMENTS

| | | |
|---|---|---|
| DE | 10018560 A1 | 10/2001 |
| DE | 102008011899 A1 | 9/2009 |
| DE | 102010015736 A1 | 10/2010 |
| EP | 0727298 A1 | 8/1996 |
| EP | 0727298 B1 | 8/1999 |

(56) References Cited

FOREIGN PATENT DOCUMENTS

| | | |
|---|---|---|
| EP | 1146185 A2 | 10/2001 |
| EP | 1146185 A3 | 3/2003 |
| EP | 1146185 B1 | 6/2005 |
| EP | 2489341 A2 | 8/2012 |
| EP | 2531159 A2 | 12/2012 |
| EP | 2619724 A2 | 7/2013 |
| EP | 2918255 A1 | 9/2015 |
| JP | 2003140631 A | 5/2003 |
| KR | 20130076922 A | 7/2013 |
| WO | 0101913 A1 | 1/2001 |
| WO | 2006089399 A2 | 8/2006 |
| WO | 2011097569 A2 | 8/2011 |
| WO | 2012040554 A2 | 3/2012 |
| WO | 2014021873 A1 | 2/2014 |
| WO | 2015148578 A2 | 10/2015 |
| WO | 2015157402 A1 | 10/2015 |
| WO | 2015171365 A1 | 11/2015 |
| WO | 2016025927 A1 | 2/2016 |
| WO | 2016049593 A1 | 3/2016 |
| WO | 2016049593 A4 | 5/2016 |
| WO | 2016123595 A1 | 8/2016 |
| WO | 2016196403 A1 | 12/2016 |
| WO | 2016200556 A1 | 12/2016 |
| WO | 2017027427 A1 | 2/2017 |
| WO | 2017031111 A1 | 2/2017 |
| WO | 2017058991 A1 | 4/2017 |
| WO | 2017061471 A1 | 4/2017 |
| WO | 2017070350 A1 | 4/2017 |
| WO | 2017058991 A4 | 5/2017 |
| WO | 2017070350 A4 | 7/2017 |
| WO | 2017124056 A1 | 7/2017 |
| WO | 2017201513 A1 | 11/2017 |
| WO | 2018026979 A1 | 2/2018 |
| WO | 2018154819 A1 | 8/2018 |
| WO | 2018203476 A1 | 11/2018 |
| WO | 2018216387 A1 | 11/2018 |
| WO | 2018236588 A2 | 12/2018 |
| WO | 2018236588 A3 | 1/2019 |

OTHER PUBLICATIONS

Astral Healthcare, "Opthalmology Day Surgery Chair Webpage", Apr. 2018, http://astralhealthcare.com/?product=opthalmology-day-surgery-chair, 6 pages.
Campbell, Mikey, "Apple Expected to Replace Touch ID With Two-Step Facial, Fingerprint Bio-Recognition Tech", Apple Insider, Jan. 21, 2017, http://iphone.appleinsider.com/articles/17/01/21/apple-expected-to-replace-touch-id-with-two-step-facial-fingerprint-bio-recognition-tech, 4 pages.
Doge Medical, "DOC Classic—DOC Surgery Chairs Webpage", 2014, 2 pages, https://web.archive.org/web/20140214203605/http://www.dogemedical.com/pages/en/products/surgery-chairs/doc-classic.php?lang=EN.
English language abstract and machine-assisted English translation for CN 101789230 extracted from espacenet.com database on Aug. 30, 2018, 31 pages.
English language abstract and machine-assisted English translation for JP 2003-140631 extracted from espacenet.com database on Aug. 30, 2018, 19 pages.
English language abstract and machine-assisted English translation for KR 2013-0076922 A extracted from espacenet.com database on Aug. 16, 2018, 8 pages.
English language abstract for DE 195 05 162 C1 extracted from espacenet.com database on Aug. 16, 2018, 1 page.
English language abstract for EP 0 727 298 A1 extracted from espacenet.com database on Aug. 16, 2018, 1 page.
English language abstract for EP 0 727 298 B1 extracted from espacenet.com database on Aug. 16, 2018, 1 page.
Hall, Stephen, "Nest's 3rd Generation Thermostat Gets Some New Views for its Farsight Feature", 9 to 5 Google, Jun. 14, 2016, https://9to5google.com/2016/06/14/nest-3rd-gen-thermostat-views-farsight/, 4 pages.
Hill-Rom, "Centrella Smart+Bed Brochure" 2017, 11 pages.
Imore, "How to Use Night Shift on your iPhone or iPad", video also found at https://www.imore.com/night-shift, Nov. 1, 2017, 12 pages.
Recliners.LA "Stellar 550 Large Lift Chair Recliner Webpage", Apr. 2018, https://www.recliners.la/products/ultra-comfort-stellar-550-large-lift-chair, 4 pages.
Stryker Medical, "InTouch Critical Care Bed Operations Manual", Aug. 2014, 125 pages.
Stryker, "InTouch Critical Care Bed Model FL27 (2130/2140) Operations Manual—Optional Pendant Control", 2130-009-001 Rev C, Apr. 2008, p. 25.
Supportec-Trade, "Portfolilio Webpage", 2017, https://supportec-trade.nl/en, 2 pages.
U.S. Appl. No. 16/019,973, filed Jun. 27, 2018, 90 pages.
U.S. Appl. No. 16/019,986, filed Jun. 27, 2018, 57 pages.
U.S. Appl. No. 16/020,003, filed Jun. 27, 2018, 37 pages.
U.S. Appl. No. 16/020,052, filed Jun. 27, 2018, 48 pages.
U.S. Appl. No. 16/020,068, filed Jun. 27, 2018, 125 pages.
U.S. Appl. No. 16/020,085, filed Jun. 27, 2018, 67 pages.
U.S. Appl. No. 62/525,359, filed Jun. 27, 2017.
U.S. Appl. No. 62/525,363, filed Jun. 27, 2017.
U.S. Appl. No. 62/525,368, filed Jun. 27, 2017.
U.S. Appl. No. 62/525,373, filed Jun. 27, 2017.
U.S. Appl. No. 62/525,377, filed Jun. 27, 2017.
Youtube, "Memory Seat Escape Video", Nov. 4, 2013, https://www.youtube.com/watch?v=xlghNmAK-7A, 1 page.
Youtube, "Microsoft HoloLens: Partner Spotlight with Stryker Communications Video", Feb. 21, 2017, https://www.youtube.com/watch?v=FTPxUGRGpnA, 3 pages.
English language abstract for DE 100 18 560 extracted from espacenet.com database on Mar. 20, 2019, 2 pages.
English language abstract and machine-assisted English translation for DE 10 2008 011 899 extracted from espacenet.com database on Mar. 20, 2019, 13 pages.
English language abstract and machine-assisted English translation for DE 10 2010 015 736 extracted from espacenet.com database on Mar. 20, 2019, 7 pages.
English language abstract for EP 1 146 185 A2 extracted from espacenet.com database on Mar. 20, 2019, 2 pages.
English language abstract for EP 1 146 185 A3 extracted from espacenet.com database on Mar. 20, 2019, 2 pages.
English language abstract for EP 1 146 185 B1 extracted from espacenet.com database on Mar. 20, 2019, 2 pages.
English language abstract and machine-assisted English translation for WO 2017/061471 extracted from espacenet.com database on Mar. 25, 2019, 26 pages.
English language abstract and machine-assisted English translation for WO 2018/154819 extracted from espacenet.com database on Mar. 25, 2019, 35 pages.
English language abstract and machine-assisted English translation for WO 2018/203476 extracted from espacenet.com database on Mar. 25, 2019, 37 pages.
English language abstract and machine-assisted English translation for WO 2018/216387 extracted from espacenet.com database on Mar. 25, 2019, 43 pages.
Youtube, "Umano Medical Med Surg Bed: The Next Generation of Medical Bed (Canadian Version) Video", https://www.bing.com/videos/search?q=umano+ook+snow&&view=detail&mid=2407A16C09D0734591912407A16C09D073459191&rvsmid=FFCD5876C49E791738DFFFCD5876C49E791738DF&FORM=VDRVRV, Apr. 14, 2015, 3 pages.

\* cited by examiner

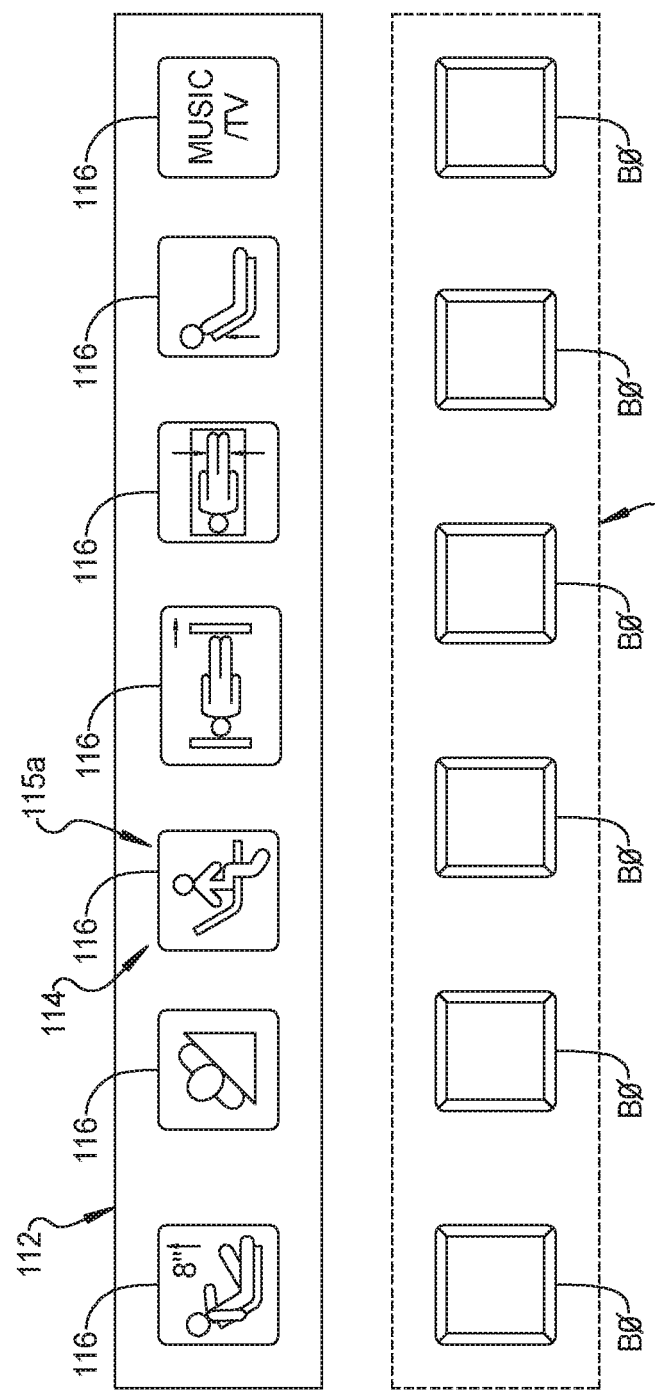

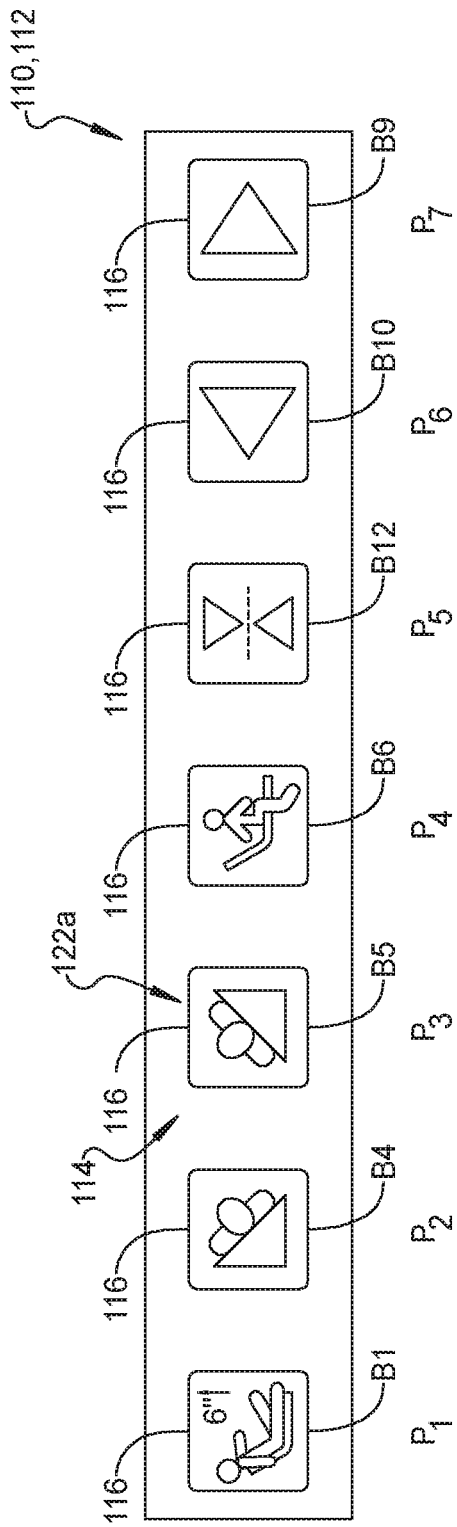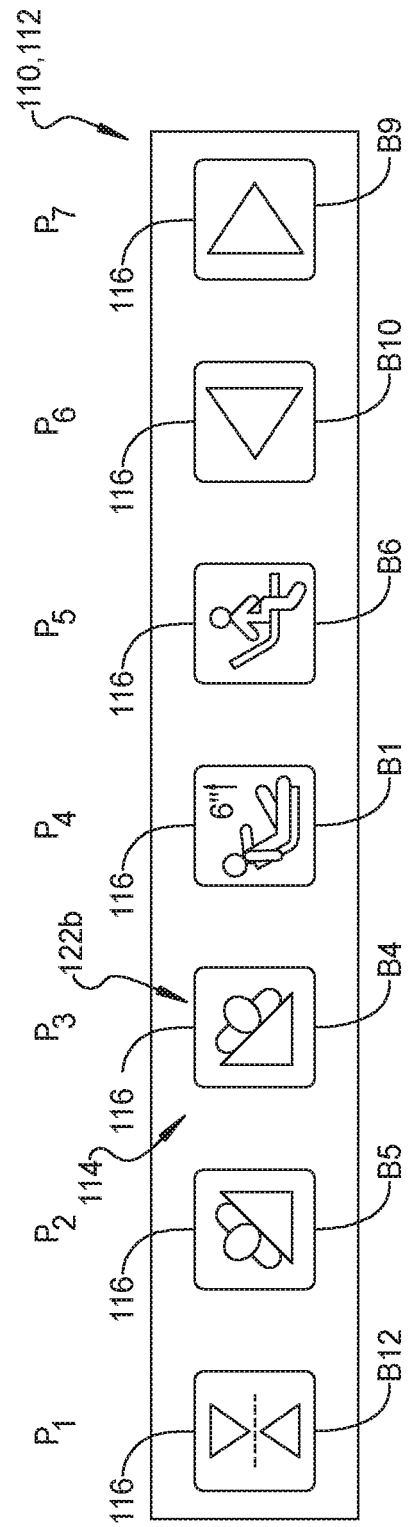

| UPPER LIMB OBSERVATION CHART | | | DATE OF BIRTH | | |
|---|---|---|---|---|---|
| CONSULTANT | | | | | |
| DATE | | | INITIALS | | |
| TIME | | | | | |
| COLOUR | | RIGHT | SWELLING | | RIGHT |
| | | LEFT | | | LEFT |
| WARMTH | | RIGHT | PULSES | | RIGHT |
| | | LEFT | | | LEFT |
| MOVEMENT | RADIAL | RIGHT | VENOUS RETURN | | RIGHT |
| | | LEFT | | | LEFT |
| | MEDIAN | RIGHT | PAIN SCORE 1-10 | | RIGHT |
| | | LEFT | | | LEFT |
| | ULNAR | RIGHT | ADDITIONAL COMMENTS | | |
| | | LEFT | | | |
| SENSATION | RADIAL | RIGHT | | | |
| | | LEFT | | | |
| | MEDIAN | RIGHT | | | |
| | | LEFT | | | |
| ULNAR | | RIGHT | | | |
| | | LEFT | | | |

FIG. 11A

| LOWER LIMB OBSERVATION CHART | | | DATE OF BIRTH | | |
|---|---|---|---|---|---|
| CONSULTANT | | | | | |
| DATE | | | INITIALS | | |
| TIME | | | | | |
| COLOUR | | RIGHT | SWELLING | RIGHT | |
| | | LEFT | | LEFT | |
| WARMTH | | RIGHT | PULSES | RIGHT | |
| | | LEFT | | LEFT | |
| MOVEMENT | PERONEAL | RIGHT | VENOUS RETURN | RIGHT | |
| | | LEFT | | LEFT | |
| | TIBIAL | RIGHT | PAIN SCORE 1-10 | RIGHT | |
| | | LEFT | | LEFT | |
| SENSATION | PERONEAL NERVE | RIGHT | ADDITIONAL COMMENTS | | |
| | | LEFT | | | |
| | TIBIAL NERVE | RIGHT | | | |
| | | LEFT | | | |

| IDENTIFIER | USER | USER GROUP | CONDITION 1 | CONDITION 2 | USER PERMISSIONS |
|---|---|---|---|---|---|
| PH1234 | PETER HANSON | PATIENT | MIGRAINE | COUGH | PATIENT |
| SC5201 | STEVE CHANG | PATIENT | DVT | | PATIENT |
| SQ5185 | SUSIE QUEUE | PATIENT | UPPER LIMB FRACTURE | HEAD CONTUSION | PATIENT |
| JS9821 | JILL SMITH | PHYSICIAN | | | LEVEL 5 |
| SC5461 | SCOTT CLINTON | NURSE PRACTITIONER | | | LEVEL 4 |
| JJ7321 | JOHN JONES | PHYSICIAN ASSISTANT | | | LEVEL 3 |
| SS3354 | SAM SAMSON | PHYSICAL THERAPIST | | | LEVEL 2 |
| JW2694 | JIM WEBSTER | ORDERLY | | | LEVEL 1 |

FIG. 18

| IDENTIFIER | USER | USER GROUP | USER PERMISSIONS | | | |
|---|---|---|---|---|---|---|
| | | | Rx | VIEW EMR | EDIT EMR | PSA |
| JS9821 | JILL SMITH | PHYSICIAN | X | X | X | X |
| SC5461 | SCOTT CLINTON | NURSE PRACTITIONER | X | X | X | X |
| JJ7321 | JOHN JONES | PHYSICIAN ASSISTANT | | X | X | X |
| SS3354 | SAM SAMSON | PHYSICAL THERAPIST | | X | | X |
| JW2694 | JIM WEBSTER | ORDERLY | | | | X |

FIG. 19

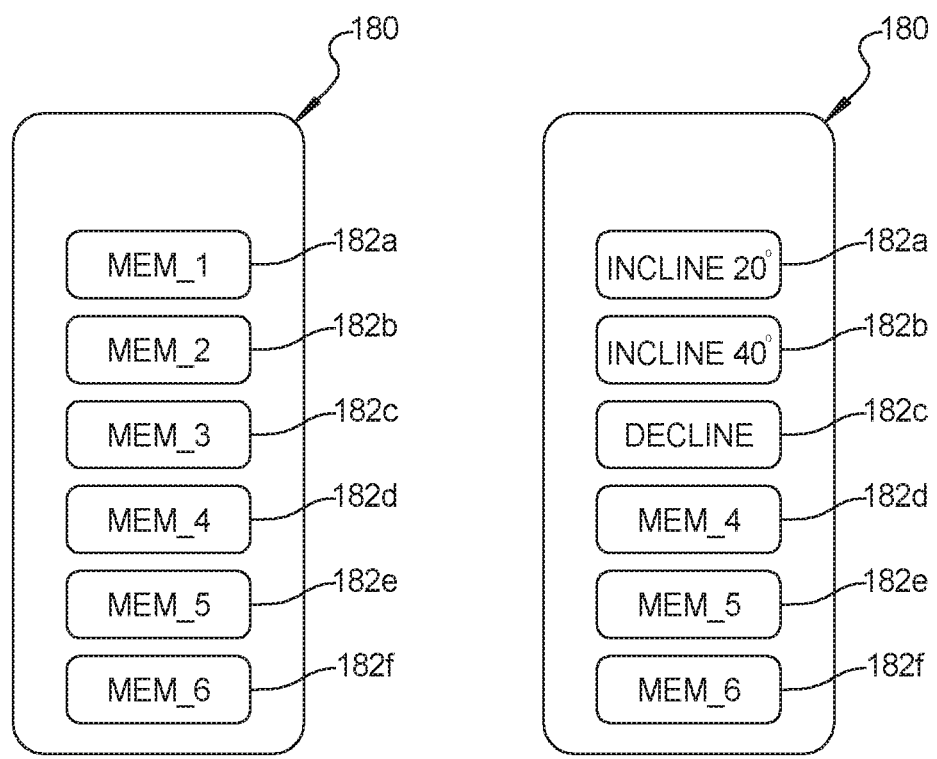

PATIENT SUPPORT SYSTEMS AND METHODS FOR ASSISTING CAREGIVERS WITH PATIENT CARE

CROSS REFERENCE TO RELATED APPLICATIONS

This application claims priority to and the benefit of U.S. Provisional Patent Application No. 62/525,353, entitled PATIENT SUPPORT SYSTEMS AND METHODS FOR ASSISTING CAREGIVERS WITH PATIENT CARE and filed on Jun. 27, 2017, the contents of which is hereby incorporated by reference in its entirety.

BACKGROUND

Patient support systems facilitate care of patients in a health care setting. Patient support systems comprise patient support apparatuses such as, for example, hospital beds, stretchers, cots, tables, wheelchairs, and chairs. Conventional patient support apparatuses comprise a base and a patient support surface upon which the patient is supported. Often, these patient support apparatuses have one or more powered devices to perform one or more functions on the patient support apparatus. These functions can include lifting and lowering the patient support surface, raising a patient from a slouched position, turning a patient, centering a patient, extending a length or width of the patient support apparatus, and the like. When a user such as a caregiver wishes to operate a powered device to perform a function, the user actuates a user interface. Conventional user interfaces may comprise a panel of buttons configured to selectively operate the various functions of the patient support apparatus.

The number and complexity of the functions integrated into the patient support apparatus continue to increase, and the user interfaces have become correspondingly advanced. Yet certain functions of the patient support apparatus, such as lifting and lowering the patient support surface, are commonly utilized more frequently than others. Similarly, only a portion of the available functions of the patient support apparatus may be utilized for a particular patient based on his or her condition. Making those functions more readily accessible to the user would be beneficial. Therefore, there is a need in the art for a patient support system comprising a user interface with customizable and/or adaptive user menus. The customized and/or adaptive user menus improve accessibility of commonly utilized or more desirable functions of the patient support apparatus, thereby improving ease of operating the patient support apparatus.

BRIEF DESCRIPTION OF THE DRAWINGS

Advantages of the present disclosure will be readily appreciated as the same becomes better understood by reference to the following detailed description when considered in connection with the accompanying drawings.

FIG. 4 is a user interface and a display displaying a user menu in accordance with another exemplary embodiment. The user interface may comprise generic buttons corresponding to indicia displayed on the display.

FIG. 6A is an initial user comprising indicia representative of the operations of the patient support apparatus of FIG. 1 with the indicia comprising an initial arrangement.

FIG. 6B is a customized user menu comprising the indicia of FIG. 6A with an updated arrangement different from the initial arrangement of the indicia.

FIG. 11A is a position-based output comprising an upper limb observation chart.

FIG. 18 is a referential database correlating the identifier of a plurality of users with one or more of a user group, condition(s) and user permissions.

FIG. 19 is another referential database correlating the identifier of a plurality of users with one or more of a user group, and user permissions.

FIG. 20 is a control suite with customizable controls.

FIG. 21 is the control suite of FIG. 20 with two of the customizable controls provided with user-selected labels.

DETAILED DESCRIPTION

Figure 1:
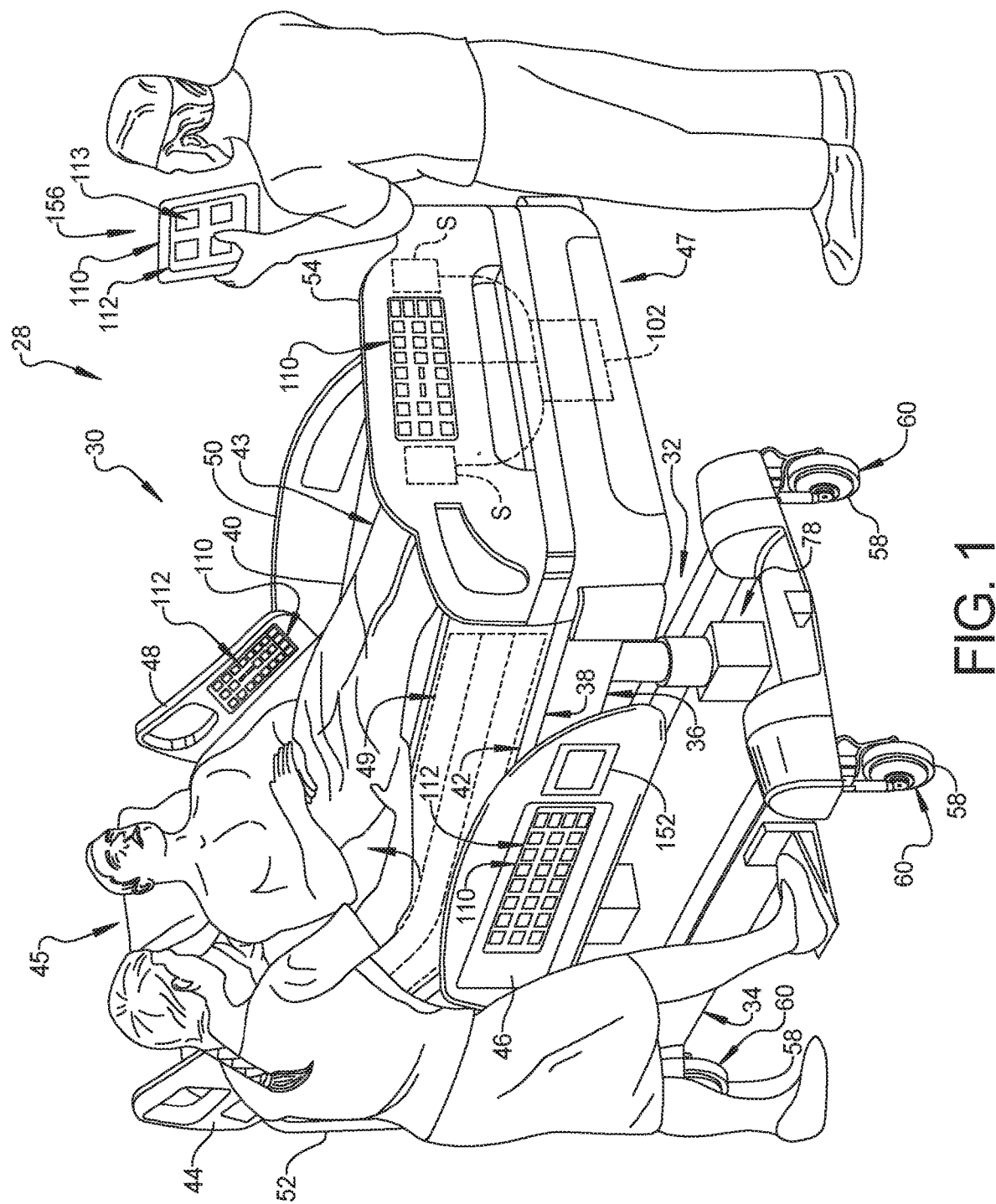
FIG. 1 is perspective view of a patient support system in accordance with an exemplary embodiment of the present disclosure. The patient is supported on a patient support apparatus. Two caregivers are positioned in proximity to the patient support apparatus.

FIG. 1 shows a patient support system 28 comprising a patient support apparatus 30 for supporting a patient. The patient support apparatus 30 illustrated in FIG. 1 comprises a hospital bed. In other embodiments, the patient support apparatus 30 may comprise a stretcher, cot, table, wheelchair, chair, or similar apparatus utilized in the care of a patient.

A support structure 32 provides support for the patient. The support structure 32 illustrated in FIG. 1 comprises a base 34 and an intermediate frame 36. The intermediate frame 36 is spaced above the base 34. The support structure 32 also comprises a patient support deck 38 disposed on the intermediate frame 36. The patient support deck 38 comprises several sections, some of which are pivotable relative to the intermediate frame 36, such as a fowler section, a seat section, a thigh section, and a foot section. The patient support deck 38 provides a patient support surface 42 upon which the patient is supported.

A mattress 40 is disposed on the patient support deck 38. The mattress 40 comprises a secondary patient support surface 43 upon which the patient is supported. The base 34, intermediate frame 36, patient support deck 38, and patient support surfaces 42, 43 each have a head end 45 and a foot end 47 corresponding to a designated placement of the patient's head and feet on the patient support apparatus 30. The construction of the support structure 32 may take on any known or conventional design, and is not limited to that specifically set forth above. In addition, the mattress 40 may be omitted in certain embodiments, such that the patient rests directly on the patient support surface 42.

Side rails 44, 46, 48, 50 are coupled to the intermediate frame 36 and thereby supported by the base 34. A first side rail 44 is positioned at a right head end of the intermediate frame 36. A second side rail 46 is positioned at a right foot end of the intermediate frame 36. A third side rail 48 is positioned at a left head end of the intermediate frame 36. A fourth side rail 50 is positioned at a left foot end of the intermediate frame 36. If the patient support apparatus 30 is a stretcher or a cot, there may be fewer side rails. The side rails 44, 46, 48, 50 are movable between a raised position in which they block ingress into and egress out of the patient support apparatus 30, one or more intermediate positions, and a lowered position in which they are not an obstacle to such ingress and egress. In still other configurations, the patient support apparatus 30 may not include any side rails.

A headboard 52 and a footboard 54 are coupled to the intermediate frame 36. In other embodiments, when the headboard 52 and the footboard 54 are included, the headboard 52 and the footboard 54 may be coupled to other locations on the patient support apparatus 30, such as the base 34. In still other embodiments, the patient support apparatus 30 does not include the headboard 52 and/or the footboard 54.

Wheels 58 are coupled to the base 34 to facilitate transport over floor surfaces. The wheels 58 are arranged in each of four quadrants of the base 34 adjacent to corners of the base 34. In the embodiment shown, the wheels 58 are caster wheels able to rotate and swivel relative to the support structure 32 during transport. Each of the wheels 58 forms part of a caster assembly 60. Each caster assembly 60 is mounted to the base 34. It should be understood that various configurations of the caster assemblies 60 are contemplated. In addition, in some embodiments, the wheels 58 are not caster wheels and may be non-steerable, steerable, non-powered, powered, or combinations thereof. Additional wheels are also contemplated. For example, the patient support apparatus 30 may comprise four non-powered, non-steerable wheels, along with one or more powered wheels. In some cases, the patient support apparatus 30 may not include any wheels.

Figure 2:
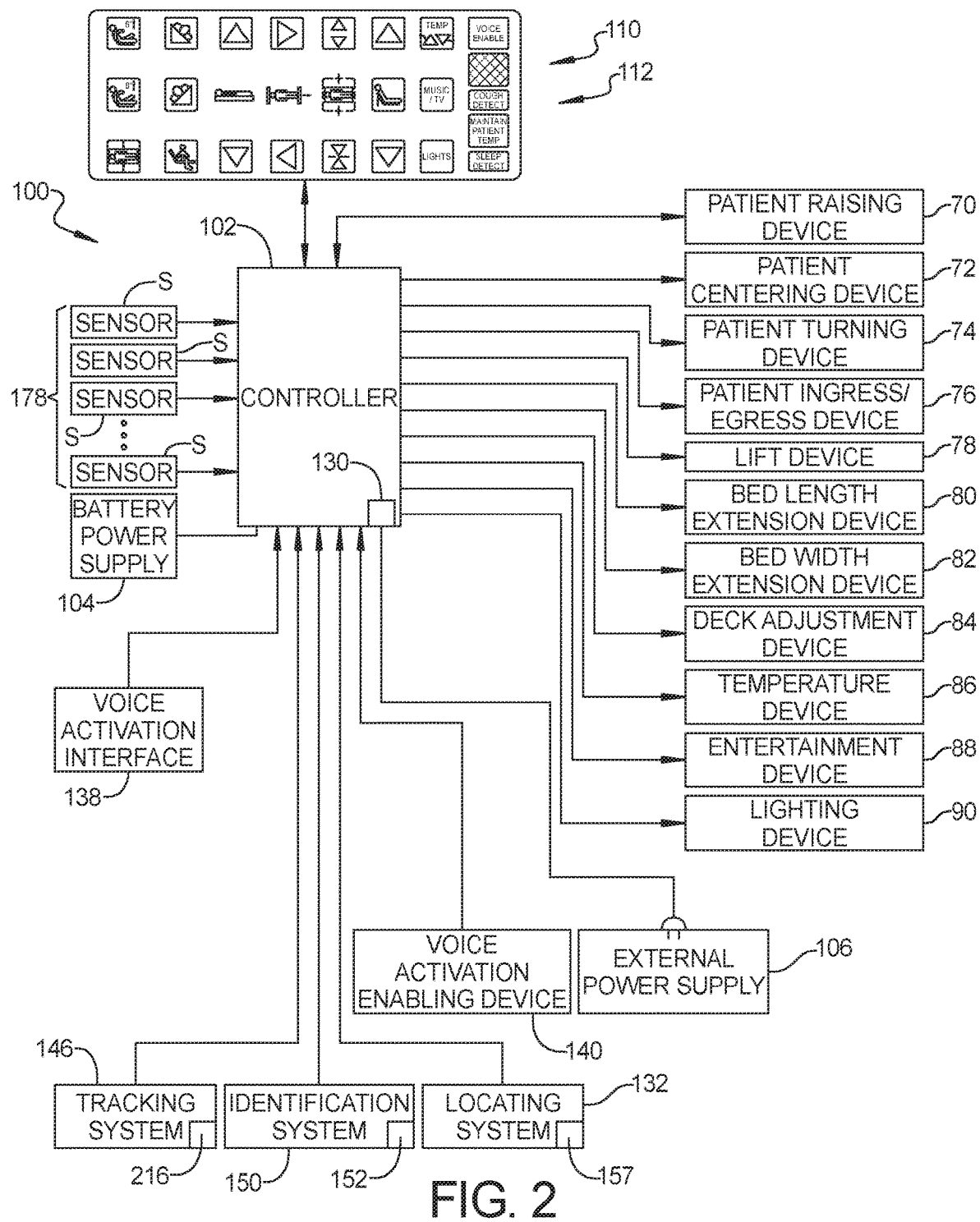
FIG. 2 is a schematic view of the patient support system of FIG. 1.

Referring to FIG. 2, the patient support system 28 may comprise one or more operational devices 70-90 of the patient support apparatus 30, each configured to perform one or more predetermined operational functions. The operational devices 70-90 utilize one or more components that require electricity. The operational devices 70-90 may comprise powered devices for adjustment, such as a patient raising device 70, a patient centering device 72, a patient turning device 74, a patient ingress/egress device 76, a lift device 78, a bed length extension device 80, a bed width extension device 82, and a deck adjustment device 84. The operational devices 70-90 may also comprise powered devices for comfort, such as a temperature device 86, an entertainment device 88, and a lighting device 90. Other devices are also contemplated. For instance, operational devices comprising percussion devices, compression devices, vibration devices, and other patient therapy devices may also be employed.

The patient support system 28 comprises a control system 100 to control the operational devices 70-90 of the patient support apparatus 30, and a controller 102. The control system 100 controls the operational devices 70-90, or components thereof, to operate their associated actuators, control their pumps, control their valves, or otherwise cause the operational devices 70-90 to perform one or more of the desired functions. The control system 100 may comprise the controller 102 such that the controller 102 is a functional subsystem of the control system 100. In other embodiments, the controller 102 may be a discrete system separate from the control system 100. In other words, the control system 100 and the controller 102 may be structurally integrated or separate. In one embodiment, the controller 102 is on-board the patient support apparatus 30 (e.g., coupled to the base 34, the footboard 54, or the like), and in another embodiment, the controller 102 is remotely located from the patient support apparatus 30 and in communication with the operational devices 70-90 disposed on-board the patient support apparatus 30. The controller 102 may communicate with the operational devices 70-90 via wired or wireless connections.

The controller 102 may comprise one or more microprocessors for processing instructions or for processing an algorithm stored in non-transitory memory 130 to control the operational devices 70-90. The control system 100 and/or controller 102 may comprise one or more microcontrollers, subcontrollers, field programmable gate arrays, systems on a chip, discrete circuitry, and/or other suitable hardware, software, or firmware that is capable of carrying out the functions described herein. Power to the operational devices 70-90 and/or the controller 102 may be provided by a battery power supply 104 or an external power source 106.

The operational devices 70-90 may have many possible configurations for performing the predetermined functions of the patient support apparatus 30. Exemplary embodiments of the operational devices 70-90 are described further below, including the patient raising device 70, the patient centering device 72, the patient turning device 74, the patient ingress/egress device 76, the lift device 78, the bed length extension device 80, the bed width extension device 82, the deck adjustment device 84, the temperature device 86, the entertainment device 88, and the lighting device 90. Further specifics regarding the exemplary devices are described in commonly owned U.S. patent application Ser. No. 15/353,179, filed on Nov. 16, 2016, which is hereby incorporated by reference herein in its entirety. Numerous devices other than those specifically described are contemplated, including a gatch adjustment device, a cleaning device, a coordinated motion device, a transport device, a cardiopulmonary resuscitation (CPR) device, an information transmission device (to the patient's electronic medical record (EMR) or electronic health record (EHR)), a sit-to-stand assist device, a cough detection device, a sleep detection device, among others. Any of the described and/or contemplated devices may be integrated into the customized and/or adaptive user menus of the present disclosure.

The patient raising device 70 is configured to perform the function of moving the patient from a slouched position towards a non-slouched position by moving the patient towards the head end of the patient support apparatus 30. The patient raising device 70 may comprise a patient raising bladder structure within the mattress 40. The patient raising bladder structure may comprise patient raising inflation bladders that are connected together longitudinally so that each of the patient raising inflation bladders spans across a majority of a width of the mattress 40 below the patient, and the patient raising inflation bladders span a majority of a length of the mattress 40 below the patient. A progressive inflation scheme with the patient raising bladder structure is used to raise the patient from the slouched position to the non-slouched position. In response to a control signal from the controller 102, the patient raising inflation bladders are inflated and deflated to create a wave-like force directed towards the head end of the patient support apparatus 30 to push the patient toward the head end. In one example, only one of the patient raising inflation bladders is fully inflated at a time to create the wave-like force needed to raise the patient. Once fully inflated, each patient raising inflation bladder begins to deflate and the next adjacent patient raising inflation bladder toward the head end begins to inflate.

The patient centering device 72 is configured to move the patient from an off-center position toward a longitudinal centerline of the mattress 40, such as when the patient has shifted too far to one side or the other of the mattress 40. The patient centering device 72 may comprise a patient centering/turning bladder structure within the mattress 40. The patient centering/turning bladder structure comprises a pair of elongate bladders that are connected together along a longitudinal seam so that each of the elongate bladders spans a majority of the length of the mattress 40, but spans one half or less the width of the mattress 40, below the patient. In response to a control signal from the controller 102, the elongate bladders are selectively inflated to guide the patient toward the longitudinal centerline of the mattress 40 when desired. Movement of the patient toward the longitudinal centerline may not be immediate, but may occur gradually as the elongate bladders remain inflated.

The patient turning device 74 is configured to perform the function of turning the patient and/or providing rotational therapy to the patient. The patient turning device 74 may utilize the patient centering/turning bladder structure as the patient centering device 72. In response to a control signal from the controller 102, the elongate bladders are independently inflated to raise one side or the other of the patient. If used for rotation therapy, then the elongate bladders are used for rotation therapy by sequentially inflating/deflating the elongate bladders to raise one side of the patient to a desired angle, lower the patient, and then raise the other side of the patient to the desired angle such that the patient experiences a side-to-side rotation that shifts pressures between the patient and the mattress 40.

The patient ingress/egress device 76 is configured to perform the function of easing ingress and/or egress of the patient to and/or from the patient support apparatus 30. The patient ingress/egress device 76 comprises a main air bladder positioned within the mattress 40. The main air bladder is sized to extend substantially the full width of the mattress 40 and a majority of the length of the mattress 40. In an exemplary embodiment, the main air bladder comprises a single air bladder that can be inflated and deflated, depending on the needs of the patient or the caregiver. The controller 102 transmits a control signal to fully inflate the main air bladder to ease ingress and egress of the patient. For instance, if the main air bladder is less than fully inflated, e.g., to soften the mattress 40 and provide additional comfort to the patient, it can be difficult for the patient to move across the mattress 40 for ingress or egress. Accordingly, by fully inflating, and stiffening the mattress 40, movement across the mattress 40 can be made easier for the patient.

The lift device 78 is configured to lift and lower the patient between the minimum and maximum heights of the patient support apparatus 30, and intermediate positions therebetween. Referring to FIG. 1, a pair of column lifts are illustrated to perform this function. In other embodiments, the lift device 78 comprises a pair of lift arms vertically extending between the base 34 and the intermediate frame 36. The lift device 78 may comprise electromagnetic, electric, pneumatic, or hydraulic actuators, or other types of linear actuators. In response to a control signal from the controller 102, the lift device 78 operates to raise or lower the patient support surface 42, 43 relative to the base 34.

The bed length extension device 80 is configured to perform the function of adjusting a length of the patient support apparatus 30 to accommodate patients of greater than average height. In an exemplary embodiment, the bed length extension device 80 comprises a pair of actuators to move a bed extension between an unextended position and extended positions with respect to the intermediate frame 36. In some embodiments, the bed extension is movable from zero to at least twelve inches from the unextended position to a fully-extended position. In other embodiments, the bed extension is able to move less or more than twelve inches and may be extendable to any position between the unextended and fully-extended position using the actuators 192. The bed extension may have two, three, four, or nearly an infinite number of extended positions in which to be adjusted by the actuators.

The bed width extension device 82 is configured to perform a function of adjusting a width of the patient support apparatus 30 to accommodate patients of greater than average width. The bed width extension device 82 may operate in the same manner as the bed length extension device 80. The bed width extension device 82 may comprise two sets of actuators to move four bed extensions between unextended and extended positions with respect to the intermediate frame 36. In some cases only one actuator or one set of actuators is employed. In some embodiments, each of the bed extensions is movable from zero to at least twelve inches from the unextended position to a fully-extended position. In other embodiments, each of the bed extensions is able to move less or more than twelve inches and may be extendable to any position between the unextended and the fully extended position using the actuators. Each of the bed extensions may have two, three, four, or nearly an infinite number of extended positions in which to be adjusted by the actuators.

The deck adjustment device 84 is configured to articulate one or more of the deck sections of the patient support apparatus 30. In an exemplary embodiment, the deck adjustment device 84 comprises one or more deck actuators to move one or more of the deck sections of the patient support apparatus 30 including but not limited to the fowler section, the seat section, the thigh section, and the foot section. The actuators may comprise electric linear actuators extending between the intermediate frame 36 and the particular deck section being adjusted. For example, in response to a control signal from the controller 102, actuation of the deck actuator raises and lowers the fowler section at various inclination angles relative to the intermediate frame 36. Suitable linear actuators are supplied by LINAK A/S located at Smedevænget 8, Guderup, DK-6430, Nordborg, Denmark. It is contemplated that any suitable deck adjustment system may be utilized in conjunction with the patient support apparatus 30, so long as the deck adjustment is configured to move one or more of the deck sections.

The temperature device 86 is configured to adjust the temperature of the patient, the temperature of the patient support apparatus 30, and/or the temperature of the room in which the patient resides for purposes of patient comfort, therapy, or recovery.

An entertainment device 88 may be activated or adjusted for patient comfort or therapeutic purposes. The entertainment device 88 may be activated or adjusted to provide soothing entertainment or background noise to the patient. In some embodiments the entertainment device 88 comprises at least one piece of entertainment equipment (e.g., television, radio, etc.).

The lighting device 90 may comprise one or more light sources and a dimmer apparatus connected to the light sources to provide lighting that makes the patient more comfortable. In some embodiments one or more of the light sources may be adjusted to be on, off, dimmed or brightened to provide soothing lighting to the patient. In other embodiments, active cancelling of noise may also be employed to make the patient more comfortable.

The operational devices 70-90 of the patient support apparatus 30 are controlled by the control system 100 in response to the user providing an input to a user interface 110. Referring to FIGS. 1 and 2, the patient support system 28 comprises the user interface 110 in communication with the controller 102 and configured to receive input from the user. Based on the input from the user to the user interface 110, the controller 102 generates and transmits a control signal to control the operational devices 70-90. The user interface 110 may comprise devices capable of being actuated by or receiving input from a user, such as the caregiver or the patient. The user interface 110 may be configured to be actuated in a variety of different ways, including but not limited to, mechanical actuation (e.g., hand, foot, finger, etc.), hands-free actuation (e.g., voice, foot, etc.), and the like. Each user interface 110 may comprise a button, a gesture sensing device for monitoring motion of hands, feet, or other body parts of the caregiver (such as through a camera), a microphone for receiving voice activation commands, and a sensor (e.g., infrared sensor such as a light bar or light beam to sense a user's body part, ultrasonic sensor, etc.). It should be appreciated that any combination of user interfaces 110 may also be utilized for any of the operational devices 70-90.

The user interface 110 may be located on one of the side rails 44, 46, 48, 50, the headboard 52, the footboard 54, or other suitable locations. FIG. 1 shows the user interface 110 is located on two of the side rails 46, 48 and the footboard 54. Additionally or alternatively, the user interface 110 may also be located on the mobile device 156 (e.g., iWatch®, iPhone®, iPad®, or similar electronic devices). FIG. 1 shows a caregiver holding the mobile device 156 comprising a touchscreen 113 with the user interface 110.

The patient support system 28 further comprises a display 112 in communication with the controller 102. The display may comprise devices capable of displaying or otherwise outputting information to the user, such as the caregiver or the patient. Suitable displays (e.g., liquid crystal display, light-emitting diode, cathode ray tube, etc.) are well known in the art. The display 112 may be located on one of the side rails 44, 46, 48, 50, the headboard 52, the footboard 54, or other suitable locations. In the embodiment shown in FIG. 1, the display 112 is located on two of the side rails 46, 48 and the footboard 54. Additionally or alternatively, the user interface 110 may also be located on the mobile device 156. FIG. 1 shows a caregiver holding the mobile device 156 comprising the touchscreen 113 with the display 112.

In certain embodiments, the user interface 110 and/or the display 112 may be integrated into a pendant (not shown) coupled to the patient support apparatus 30. The pendant may be handheld and coupled to the patient support apparatus 30 with a tether, which may also include the electrical and data connection. The pendant may serve as the control suite for some or all of the functions of the patient support system 28 described throughout the present disclosure. In certain embodiments, the pendant integrates the entertainment device 88 and the lighting device 90. In particular, the pendant includes a plurality of tactile and/or touch-sensitive buttons for actuating certain features of the entertainment device 88 and the lighting device 90. Exemplary features include "channel up," "channel down," "music up," "music down," "television," "radio," "room lights," "reading lights," and the like. An exemplary pendant suitable for the present application is included on the In-Touch Critical Care Bed manufactured by Stryker Corp. (Kalamazoo, Mich.).

Figure 3:
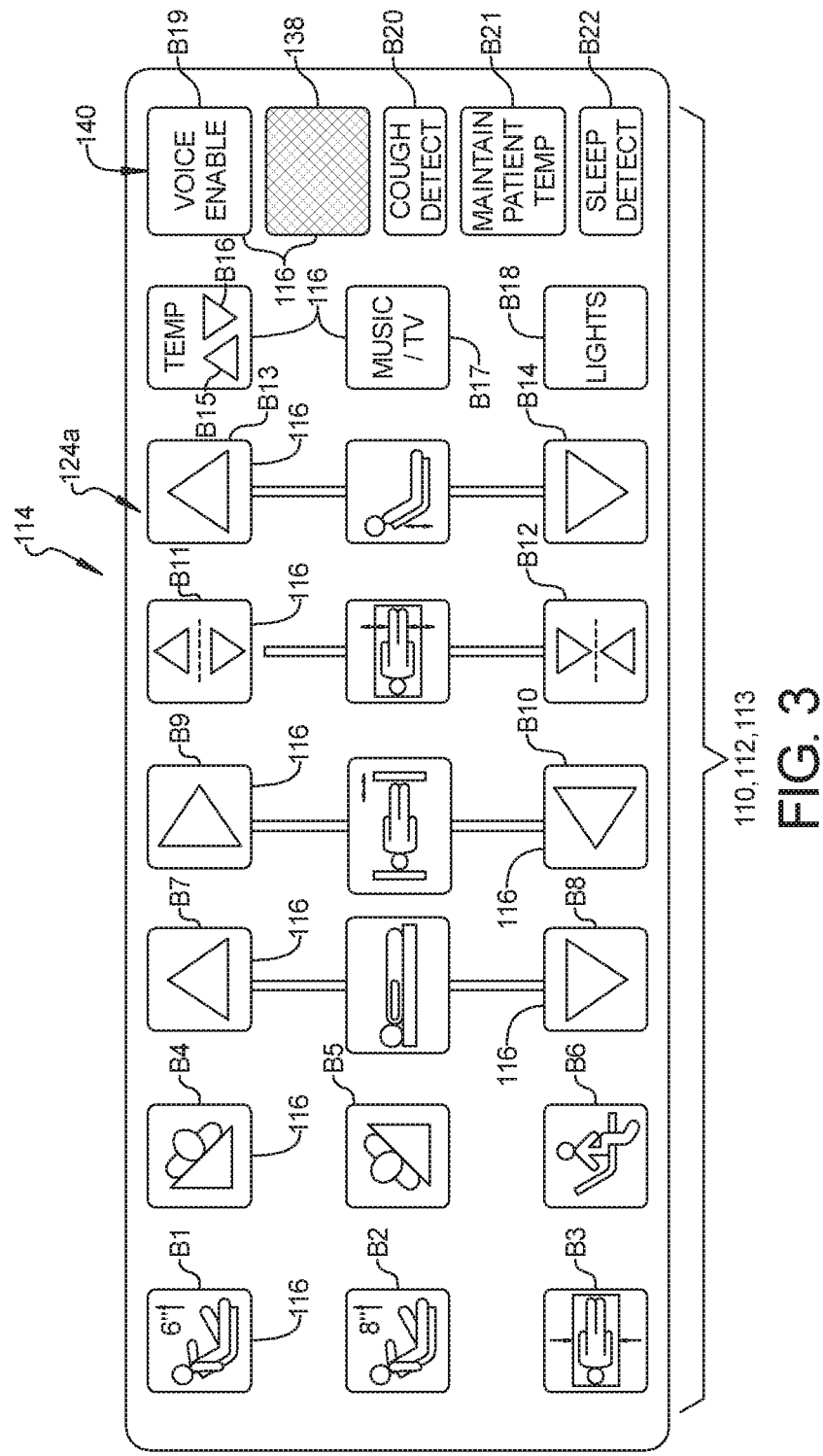
FIG. 3 is a user interface and a display of the patient support system of FIG. 1 with the display displaying a user menu. The user interface and the display may be embodied in a touchscreen.

In certain embodiments, the user interface 110 is integrated with the display 112 as a touchscreen 113, as shown in FIGS. 1 and 3. Capacitive touchscreens and other types of displays capable of receiving a touch-sensitive input are well known to those skilled in the art. Additionally or alternatively, the user interface 110 may be separate or remote from the display 112. FIG. 4 shows an illustrative example with the user interface 110 comprising tactile or virtual buttons B0 positioned adjacent the display 112. The buttons B0 are generic in appearance and function and correspond to adjacent indicia 116 displayed on the display 112.

The display 112 is configured to display user menus 114 comprising indicia 116 representative of the operational devices 70-90 of the patient support apparatus 30. The user menu 114 may be broadly defined as more than one option representative of the operational devices 70-90 displayed on the display 112. Any suitable format of the user menus 114 is contemplated, including but not limited to lists, grids and/or arrays of text, graphics, icons and/or other indicia. In the exemplary embodiments illustrated in FIGS. 3 and 4, the indicia 116 of the user menus 114 are textual and graphical icons arranged in a grid.

The user interface 110 is configured to receive the input from the user in any suitable manner including, but not limited to, mechanical actuation, voice commands, and gesturing. The user typically provides the input to the user interface 110 through the touch of a tactile or virtual button. Referring to FIG. 3, the touchscreen 113 integrates the user interface 110 and the display 112 such that each of the indicia 116 of the user menu 114 is associated with one of the virtual buttons B1-B22. Touching the corresponding indicia 116 on the touchscreen provides the input to the user interface 110.

Each of the indicia 116 displayed on the display 112 may be representative of different operational devices 70-90 of the patient support apparatus 30, or operational functions of the same. In embodiments with the touchscreen, each of the buttons B1-B22 is configured to control one of the operational devices 70-90 (or operational functions thereof). Using the virtual buttons B1-B14 shown in FIG. 3 as exemplary, the button B1, upon actuation, causes the control system 100 to control the patient raising device 70 to raise the patient six inches toward the head end of the patient support deck 38 (as may be needed when the patient is in a slouched position). The button B2, upon actuation, causes the control system 100 to control the patient raising device 70 to raise the patient eight inches toward the head end of the patient support deck 38 (as may be needed when the patient is in a slouched position and six inches of raising is not enough). The button B3, upon actuation, causes the control system 100 to control the patient centering device 72 to laterally urge the patient towards the longitudinal centerline of the mattress 40. The buttons B4 and B5, upon actuation, cause the control system 100 to control the patient turning device 74 to turn the patient on one side or another, respectively. The button B6, upon actuation, causes the control system 100 to control the patient ingress/egress device 76 to enable easier ingress/egress for the patient. The buttons B7 and B8, upon actuation, cause the control system 100 to control the lift device 78 to lift or lower the patient support surface 42 relative to the floor surface, respectively. The buttons B9 and B10, upon actuation, cause the control system 100 to control the bed length extension device 80 to lengthen or shorten the patient support apparatus 30 to accommodate taller or shorter patients. The buttons B11 and B12, upon actuation, cause the control system 100 to control the bed width extension device 82 to widen or narrow the patient support apparatus 30 to accommodate larger or smaller patients, respectively. The buttons B13 and B14, upon actuation, cause the control system 100 to control the deck adjustment device 84 to adjust a position of one or more of the deck sections of the patient support deck 38, such as the fowler section. Other buttons, not shown, are contemplated to adjust other deck sections. The caregiver may be required to continue actuating (e.g., continue depressing or continue touching) the button B1-B14 until the caregiver is satisfied with the operation that was performed. The user interface 110 may be continually actuated in other ways depending on the mode of actuation.

In some embodiments, the user input device 110 comprises a voice actuation interface 138 in communication with the controller 102. The voice actuation interface 138 may comprise a microphone in communication with the controller 102 to receive voice activation commands from the caregiver. Referring to FIG. 2, the voice activation commands are associated with the operational functions of the operational devices 70-90 in the same manner as buttons B1-B14. A voice activation enabling device 140 communicates with the controller 102. The voice activation enabling device 140 may be mounted to the base 34, the intermediate frame 36, the side rails 44, 46, 48, 50, the headboard 52, the footboard 54, or other suitable locations on the patient support apparatus 30. The voice activation enabling device 140 may also be located on a portable electronic device or otherwise remote from the patient support apparatus 30. In the embodiment shown in FIG. 3, the voice activation enabling device 140 comprises a button B19. The voice activation enabling device 140 is actuated by the caregiver to enable voice activation commands. In some embodiments, if the voice activation enabling device 140 is not actuated before voice activation commands are made, the controller 102 will not respond to the voice activation commands. In other embodiments, the voice activation interface 138 is always enabled and triggered by an initializing voice command, such that the voice activation interface 138 is ready to receive voice activation commands once the initializing voice command is given. The initializing voice command could be "ON BED" or "READY BED."

Figure 5A:
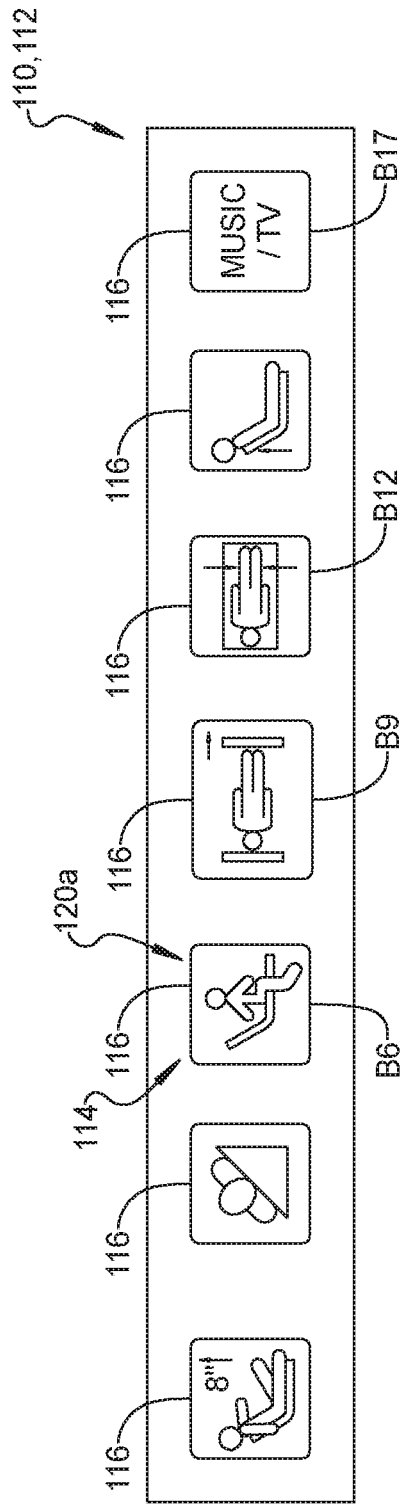
FIG. 5A is an initial user menu comprising indicia representative of the operations of the patient support apparatus of FIG. 1.
Figure 5B:
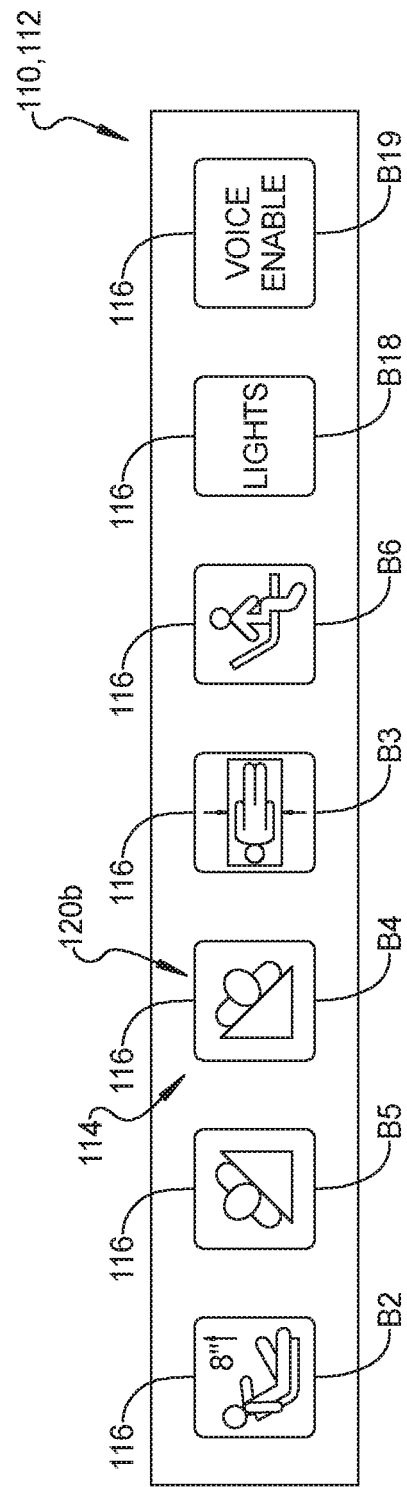
FIG. 5B is a customized user menu comprising at least one updated indicia representative of the operations of the patient support apparatus of FIG. 1.

The patient support system 28 advantageously provides customized and/or adaptive user menus in response to input from the user. FIGS. 5A and 5B illustrate exemplary user menus 114. The user menus 114 shown in FIGS. 5A and 5B may be representative of a portion of the user menu 114 of FIG. 3, the user menu 114 of FIG. 4, or any other user menu consistent with the present disclosure. The singular row of indicia 116 of the user menus 114 of FIGS. 5A and 5B (and FIGS. 6A-7B) are merely illustrative to describe the systems and methods of providing customized and/or responsive user menus in response to input from the user. The systems and methods described below may be readily applied to user menus 114 of any type, size and/or complexity.

FIG. 5A shows an exemplary initial user menu. The initial user menu 120a may be broadly defined as the user menu 114 presented to the user on the display 112 before providing a customized user menu 120b (FIG. 5B) to the user on the display 112. The initial user menu 120a may be presented, for example, after initialization of the patient support system 28 (i.e., powered up) and/or after a reset input provided to the controller 102 (e.g., when the patient support apparatus 30 is being used by a new patient for the first time or when a new user is present). The initial user menu 120a may further be considered as the user menu 114 presented to the user on the display 112 prior to each instance the user menu 114 is updated as described herein.

To display the initial user menu 120a, the controller 102 is configured to transmit an initial display signal to the display 112. In response to receiving the initial display signal, the display 112 displays the initial user menu 120a. The initial user menu 120a of FIG. 5A comprises indicia 116 representative of the patient raising device 70 (button B2), the patient turning device 74 (button B5), and the entertainment device 88 (button B17). While the initial user menu 120a is displayed on the display 112, the user provides input through any suitable manner described herein. In an exemplary embodiment, the input comprises a user selection of one of the indicia 116 from the initial user menu 120a. In response to the user selection, an input signal is generated. The input signal may be generated by the user interface 110, the display 112, the controller 102, or other suitable electronic component of the patient support system 28. The controller 102 is configured to receive the input signals from the user interface 110 based on the input (e.g., the user selection) from the user to the user interface 110 while displaying the initial user menu 120a.

Based on the input signals from the user interface 110, the controller 102 is further configured to determine usage characteristics. The usage characteristics may be broadly defined as any information discernable over time based on the nature of the user's interaction with the user interface 110. The usage characteristics may comprise a frequency that the user selects a particular one or more of the indicia 116 representative of the operational devices 70-90. For example, each time an input is provided to the user interface 110, the controller 102 receives an input signal that is stored in the non-transitory memory 130. The input signals may be processed and analyzed to determine the frequency over time the user selects indicia 116 representative of each of the operational devices 70-90 of the patient support apparatus 30. The most frequently selected indicia 116 may be presented to the user on the display 112 as the customized user menu 120b, or a portion thereof. Additionally or alternatively, the usage characteristics may comprise a previous user selection of one of the indicia 116 representative one of the operational devices 70-90. The most recently selected one, two or more indicia 116 may be presented to the user on the display 112 as the customized user menu 120b, or a portion thereof. Additionally or alternatively, the usage characteristics may comprise a time of day the user selects of one of the indicia 116 representative of one of the operational devices 70-90. For example, a user may be more likely to utilize the patient raising device 70 during the day, and the lighting device 90 during the evening. The time-appropriate indicia may be presented to the user on the display 112 as the customized user menu 120b, or a portion thereof. A combination of the above exemplary usage characteristics may be simultaneously utilized. For example, a portion of the customized user menu 120b may comprise the most frequently selected indicia, another portion the most recently selected indicia, and/or another portion the time-appropriate indicia. In other embodiments, a weighted average or a selection of more than one of the usage characteristics may be utilized in combination to determine the customized user menu 120b. The controller 102 is configured to determine the customized user menu 120b based, at least in part, on the usage characteristics in additional manners to be described.

The controller 102 generates an updated display signal representative of the customized user menu 120b. The updated display signal is transmitted to the display 112 to display the customized user menu 120b. FIG. 5B shows an exemplary customized user menu 120b. The customized user menu 120b of FIG. 5B comprises indicia 116 representative of the patient raising device 70 (button B2), the patient turning device 74 (buttons B4 and B5), the patient centering device 72 (button B3), the patient ingress/egress device 76 (button B6), the lighting device 90 (button B18), and the voice activation enabling device 140 (button B19). All, some, or none of the indicia 116 of the customized user menu 120b may be different than the indicia 116 of the initial user menu 120a. For example, both of the initial and customized user menus 120a, 120b of FIGS. 5A and 5B comprise indicia 116 representative of the patient raising device 70 (button B2) and the patient turning device 74 (button B5). The remaining indicia 116 of the initial user menu 120a have been updated with indicia 116 different from the customized user menu 120b illustrated in FIG. 5B.

In an exemplary operation, the user selects one of the indicia 116 of the initial user menu 120a, such as button B2. The controller 102 receives the input signals based on the input and determines the usage characteristics. For example, the patient raising device 70 (button B2) may be determined to be the most frequently selected one of the operational devices 70-90. For another example, the patient raising device 70 (button B2) may be the most recently selected one of the operational devices 70-90. Based on one or more of these exemplary usage characteristics, the controller 102 determines that the customized user menu 120b comprises indicia 116 representative of the patient raising device 70. The controller 102 generates the updated display signal representative of the customized user menu 120b and transmits the updated display signal to the display 112. The display 112 displays the customized user menu 120b including the indicia 116 representative of the patient raising device 70.

The representation of the indicia 116 of the customized user menu 120b may be the same or different than the indicia 116 of the initial user menu 120a. The indicia 116 of the customized user menu 120b is, in some embodiments, the same textual or pictorial representation as the initial user menu 120a such that the user maintains the association between the indicia 116 and the corresponding operational devices 70-90 of the patient support apparatus 30. Certain indicia 116 of the customized user menu 120b may be modified or updated with a visual effect (e.g., a "halo" around an icon) to represent and emphasize that those indicia 116 are unique to the customized user menu 120b as being most frequently selected, most recently selected, and the like. The visual emphasis may also include altering the size, shape, color, look, and/or feel of the indicia 116.

The customized user menu 120b may provide indicia 116 representative of the operational devices 70-90 of the patient support apparatus 30 related to the selected one of the operational devices 70-90. In any exemplary embodiment, the updated indicia 116 of the customized user menu 120b may comprise indicia 116 associated with selected indicia 116 of the initial user menu 120a. For example and with reference to FIGS. 5A and 5B, the user selects the patient turning device 74 (button B5) on the initial user menu 120a. In addition to displaying button B5 on the customized user menu 120b, the customized menu 120b may further comprise button B4 as illustrated in FIG. 5B, also corresponding to the patient turning device 74 (left turn versus right turn). Should, for example, the patient turning device 74 be the most frequently selected or most recently selected one of the operational devices 70-90, it would be beneficial for the customized user menu 120b to display the indicia 116 associated with the patient turning device 74. The indicia 116 displayed may be all of the indicia 116 associated with the patient turning device 74, or a subset thereof. The association between various operational devices 70-90 of the patient support apparatus 30 may be predefined and programmed to the controller 102, and/or determined by the controller 102 based on usage characteristics over time.

In addition to the content of a customized user menu being determined by the controller 102, other properties of the customized user menu 120b may be updated or otherwise controlled. Referring to FIGS. 6A and 6B, an exemplary initial user menu 122a comprises an initial arrangement of the indicia 116, and an exemplary updated user menu 122b comprises an updated arrangement of the indicia 116 different from the initial arrangement. The arrangements may be broadly defined as the layout of the indicia 116 on the user menus 114. The initial and updated user menus 122a, 122b of FIGS. 6A and 6B each comprises indicia 116 representative of the patient raising device 70 (button B1), the patient turning device 74 (buttons B4 and B5), the bed length extension device 80 (buttons B9 and B10), and the bed with extension device 82 (button B12). Each of the indicia 116 is at a position P1-P7 along the singular row of the user menu 114. It should be appreciated that the single row of indicia 116 of FIGS. 6A and 6B is merely illustrative, and the systems and methods described below may be readily applied to user menus 114 of any type, size and/or complexity.

In an exemplary embodiment, the input comprises a user selection of one of the indicia 116 from the initial user menu 122a. In response to the user selection to the user interface 110 while displaying the initial user menu 122a, the input signal is generated and received by the controller 102. Based on the input signals, the controller 102 is further configured to determine the usage characteristics, and further determine the customized user menu 122b based on the usage characteristics. The updated user menu 122b may include the updated arrangement of the indicia 116 comprising at least one of the indicia 116 at a different position than the initial arrangement of the indicia 116. In some cases, the most commonly or recently selected one of the indicia 116 is positioned at P1, as many individuals read left to right and are more likely to first see the indicia 116 at position P1. In the exemplary embodiment of FIGS. 6A and 6B, button B1 is positioned at P1 in the initial user menu 122a and at P4 in the updated user menu 122b; button B4 is positioned at P2 in the initial user menu 122a and at P3 in the updated user menu 122b; button B5 is positioned at P3 in the initial user menu 122a and at P2 in the updated user menu 122b; button B6 is positioned at P4 in the initial user menu 122a and at P5 in the updated user menu 122b; and button B12 is positioned at P5 in the initial user menu 122a and at P1 in the updated user menu 122b. Not all of the indicia 116 may be rearranged. FIGS. 6A and 6B show the buttons B9 and B10 remaining in the same respective positions, P7 and P6. Updating the arrangement on the display 112 provides the user with the indicia 116 representative of the more commonly and/or recently used operational devices 70-90 positioned in a readily identifiable or preferred position of the customized user menu 120b.

The initial and/or updated arrangements may maintain relative positions of the indicia 116 representative of related operational devices 70-90. In particular, when more than one indicia 116 represents opposing features (e.g., left turn and right turn) of the operational devices 70-90, it is beneficial for the updated user menu 122b to arrange those indicia 116 in a logical manner. For example, buttons B4 and B5, corresponding to the patient turning device 74, may be positioned adjacent one another in one or more of the initial and updated arrangements. Likewise, buttons B9 and B10, corresponding to the bed length extension device 80, are positioned adjacent one another in the initial and updated arrangements of FIGS. 6A and 6B. In some cases, the indicia 116 representative of related operational devices 70-90 may be arranged in a logical manner (e.g., adjacent) even if other usage characteristics (e.g., frequently selected, recently selected, etc.) suggests otherwise.

Figure 7:
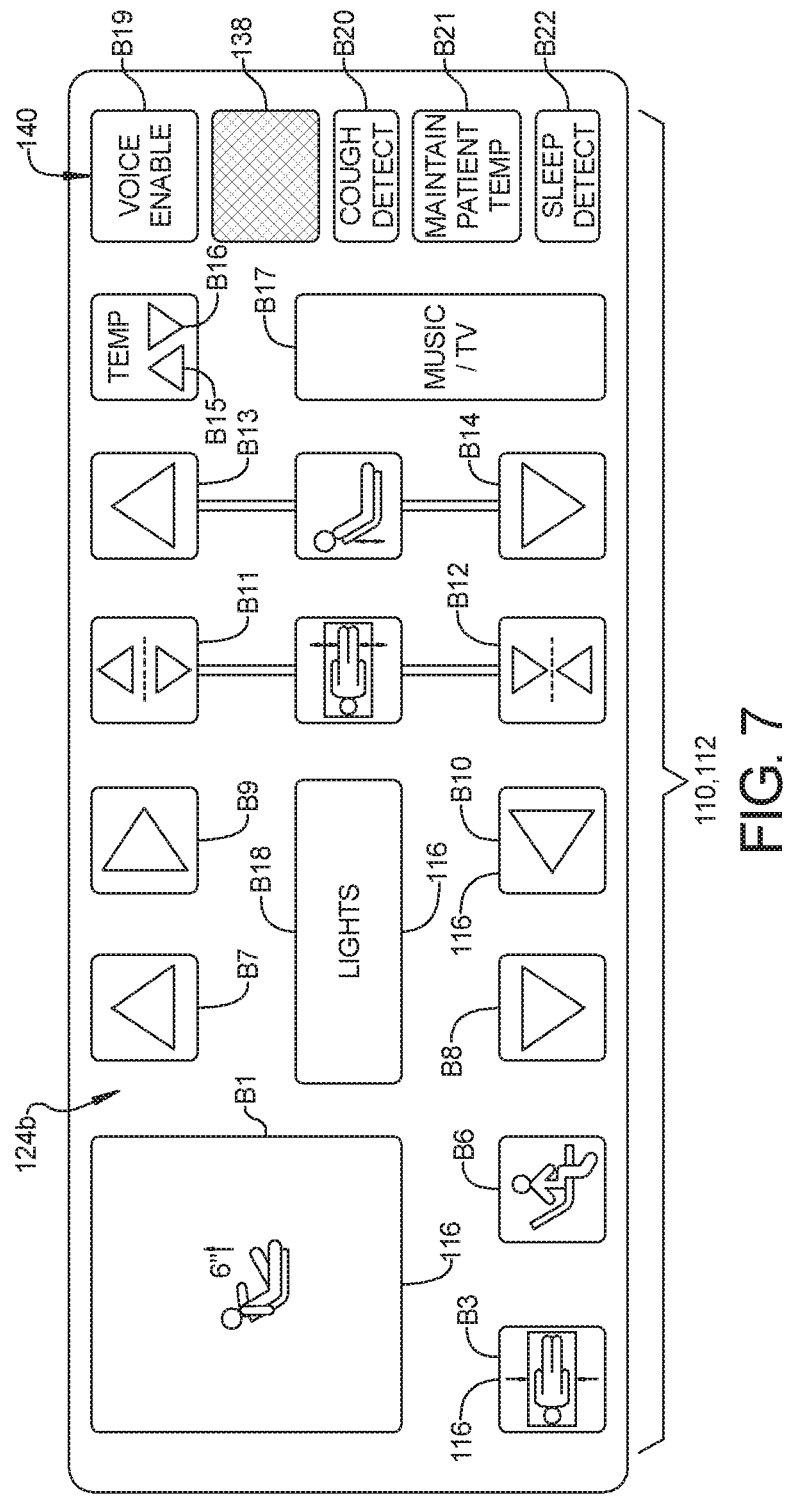
FIG. 7 is a customized user menu with an updated scaling different from an initial scaling of indicia.

The scaling of the indicia 116 may be updated based on the usage characteristic(s) or otherwise. Referring now to FIGS. 3 and 7, exemplary initial and customized user menus 124a, 124b are shown. The initial user menu 124a comprises an initial scaling of the indicia 116, and the customized user menu 124b comprises an updated scaling of the indicia 116 different from the initial scaling. The indicia 116 of the initial user menu 124a of FIG. 3 is representative of the patient raising device 70 (button B1), the entertainment device 88 (button B17), and the lighting device 90 (button B5), among others. Most of the indicia 116 of the initial user menu 124a of FIG. 3 are displayed as square tiles of equal size. Referring now to FIG. 7, some of the indicia 116 of the updated user menu 124b are displayed as different sizes relative to the corresponding indicia 116 on the initial user menu 124a. Specifically, button B1 is a square with a size approximately equal to four square tiles of the initial user menu 124a; button B17 is a vertically oriented rectangle with a size approximately equal to two square tiles of the initial user menu 124a; and button B18 is a horizontally oriented rectangle with a size approximately equal to two square tiles of the initial user menu 124a. The updated scaling of FIG. 7 is one non-limiting example. In another example, the square tiles of the updated user menu 124b may be updated with triangles, circles, and/or other shapes that are larger, smaller, and/or the same size as the initial user menu 124a.

The updating scaling illustrated in FIG. 7 generally maintains the grid-like pattern of the initial user menu 124a. The present disclosure contemplates the updated scaling may result in a different spatial alignment of the indicia 116 on the display 112. Often, modern software may be configured to provide an aesthetically pleasing visual experience for the user with graphics that are not constrained to a grid or specific spatial alignment. In such instances, changing the content or appearance of the display 112 (and user interface 110) in any manner is considered contemplated by the present disclosure.

Exemplary methods of providing the customized user menu 120b, 122b, 124b are also described. The initial user menu 120a, 122a, 124a is displayed on the display 112. The initial user menu 120a, 122a, 124a comprises indicia 116 representative of the operational devices 70-90 of the patient support apparatus. Input from the user is received on the user interface 110. The input comprises the user selection of one of the indicia 116. A control signal is generated by the controller 102 based on the user selection. The control system 100 controls the operational devices 70-90 of the patient support apparatus 30.

The input signal is transmitted from the user interface 110 to the controller 102. The input signal is based on the user selection. The controller 102 determines the usage characteristic(s) based on the input signals from the user interface 110. The controller 102 determines the customized user menu 120b, 122b, 124b based on the usage characteristic(s). The controller 102 generates an updated display signal representative of the customized user menu 120b, 122b, 124b. The updated display signal is transmitted from the controller 102 to the display 112. The customized user menu 120b, 122b, 124b is displayed on the display 112.

The controller 102 may determine the customized user menu 120b, 122b, 124b after each user selection or after a predetermined number of user selections over time, or periodically after a certain passage of time. For example, the controller 102 may update the usage characteristic(s) after a subsequent user selection to determine the customized user menu 120b, 122b, 124b. For example, the usage characteristic may comprise the frequency of selection of one of the indicia 116 with the usage characteristic stored in the non-transitory memory 130. After each subsequent user selection, the controller 102 determines the updated frequencies that each of the indicia 116 has been selected and stores the updated frequencies in the non-transitory memory 130. For another example, the usage characteristic may comprise the recent selection of one of the indicia 116 with the usage characteristic stored in the non-transitory memory 130. After the subsequent user selection, the controller 102 determines the customized user menu 120b, 122b, 124b comprising the most recently selected indicia 116. In certain embodiments, the non-transitory memory 130 is configured to store at least one of the indicia 116, the initial user menu 120a, 122a, 124a, the customized user menu 120b, 122b, 124b, and the usage characteristics.

Subsequent to updating the usage characteristic(s) and/or determining the customized user menu 120b, 122b, 124b based on the updated usage characteristic(s), the customized user menu 120b, 122b, 124b is displayed on the display 112. The (updated) customized user menu 120b, 122b, 124b may be displayed on the display 112 after each user selection or after each instance the usage characteristic(s) are updated or after a predetermined number of updates of the usage characteristic(s).

The usage characteristics may comprise the frequency of selection of the indicia 116, the recency of the selection of the indicia 116, a time of day of the selection of the indicia 116, or any other suitable information discernable over time based on the nature of the user's interaction with the user interface 110. More than one usage characteristic may be used by the controller 102 to determine the customized user menu 120b, 122b, 124b. For example, a portion of the customized user menu 120b, 122b, 124b may comprise most frequently selected indicia 116, another portion the most recently selected indicia 116, and still another portion time-appropriate indicia 116.

The usage characteristics may further be correlated with the user providing the input signals to the user interface 110. In certain embodiments, the user provides an identifier 158 to the user interface 110 prior to providing the input (e.g., user selection of indicia 116) to the user interface 110. The identifier 158 may comprise an alphanumeric code, a name, or any other information unique to the user providing input to the user interface 110 (see FIGS. 18 and 19). For example, the identifier 158 is a user profile 160 associated with the user. For another example, the identifier 158 is a user group 166 such as physicians, nurse practitioners, physicians' assistants, physical therapists, occupational therapists, patients, orderlies, and the like, with whom the user identifies. Such identifier 158 may also be automatically obtained by the control system 100 via an identification system as described further below.

The controller 102 may receive the identifier 158 prior to receiving the input signals from the user interface 110, and correlate the usage characteristics with the identifier 158. For example, each of the users may select which user group 166 he or she is associated. The controller 102 uses the subsequent input to the user interface 110 to determine the usage characteristics not only for the user but also for the user group 166. The usage characteristics for the user profile 162 and/or the user group 166 may be stored in the non-transitory memory 130 and grouped, aggregated and/or updated over time such that the customized user menu 120b, 122b, 124b is customized to the user and/or the user group 166. The subsequent occasion that, for example, a physician initiates using the user interface 110 and selects his or her user group 166, the indicia 116 representative of operational devices 70-90 most frequently used by the same physician and/or other physicians may be included in the customized user menu 120b, 122b, 124b.

Figure 8:
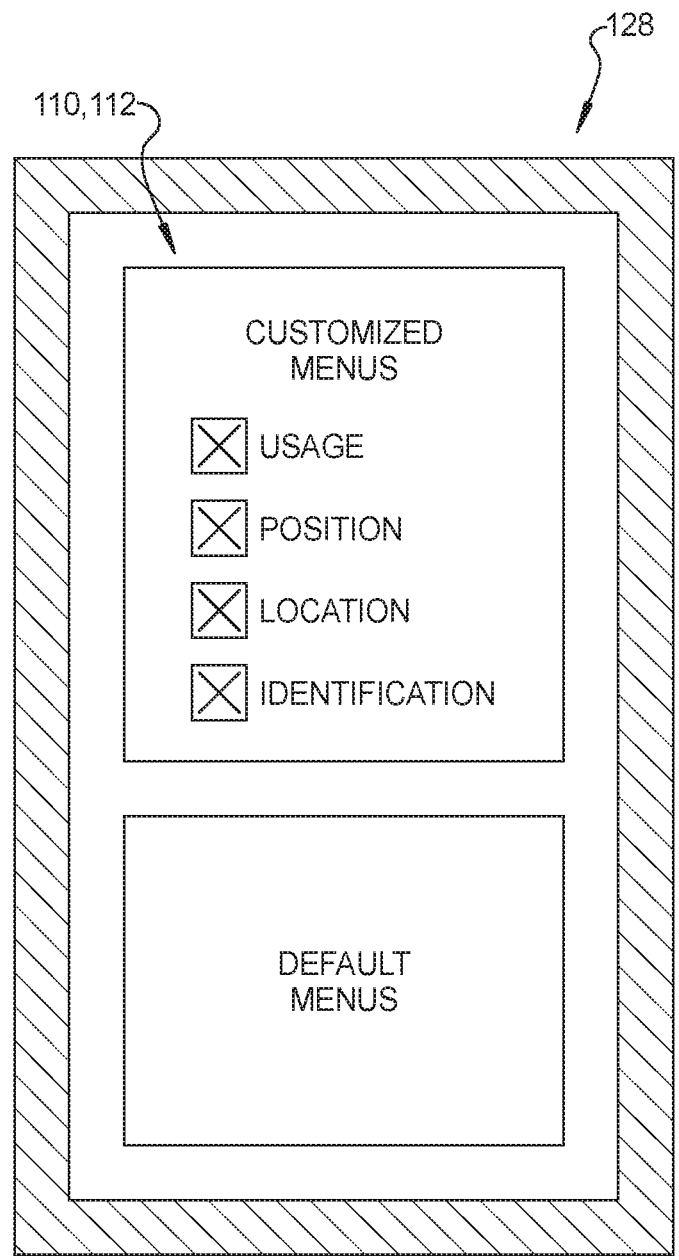
FIG. 8 is an options menu.

The display 112 and/or the user interface 110 may provide an options menu 128 to the user to select which one or more of the usage characteristics to use to determine the customized user menu 120b, 122b, 124b. FIG. 8 shows one exemplary options menu 128. The options menu 128 may also display options representative of a plurality of user menus comprising at least the initial user menu 120a, 122a, 124a and the customized user menu 120b, 122b, 124b. With the user interface 110 the user may select from the options menu 128 which one or more of the menus to display on the display 112. For example, the display 112 of FIG. 8 shows "usage," "position," "location," and "identification," corresponding to the customized user menu 120b, 122b, 124b using usage characteristics, and to a position-based user menu 134, a location-based user menu 144, and an identification-based user menu 154, respectively, to be described. The user may select one or more of the options with the user interface 110 to selectively enable and disable the customized user menu(s) associated with the parameter. FIG. 8 shows all of the parameters enabled such that the customized user menu 120b, 122b, 124b is based on one or more of the usage characteristics, the position-based user menu 134, location-based user menu 144, and the identification-based user menu 154. In certain embodiments, the user may select, with the user interface, a "default menus" option to disable the customized user menus.

In an exemplary embodiment, the initial user menu 120a, 122a, 124a is a default user menu comprising indicia representative of a predefined set of operational devices 70-90 of the patient support apparatus 30. A selection with the user interface 110 may be received from the user. The selection may comprise the user selecting to either view a default user menu or the customized user menu 120b, 122b, 124b. The selected one of the user menus is displayed on the display 112.

During the facilitation of patient care, the user, such as a caregiver, is typically positioned about the patient support apparatus 30 supporting the patient. Depending where the user is positioned about the patient support apparatus 30, it may be beneficial to display different user menus or information most appropriate to the position of the user. For example, if the user is at one of the sides 49 of the patient support apparatus 30, it may be beneficial for the user interface 110 and/or the display 112 to display the patient turning device 74. For another example, if the user is at the foot end 47 of the patient support apparatus 30, it may be beneficial for the user interface 110 and/or display 112 to display a lower extremity examination report, particularly if the user is identified as being a nurse or physician. The patient support system 28 advantageously provides position-based user menus and information, which may also be combined with user-based menus and information.

Referring to FIGS. 9 and 10A-10C, the patient support system 28 comprises the patient support apparatus 30 supporting the patient. The patient support apparatus 30 comprises the patient support surface 42, 43 (see also FIG. 1) with the head end 45 and the foot end 47 of the patient support surface 42, 43 corresponding to a designated placement of the patient's head and feet on the patient support apparatus 30, respectively. The patient support surface 42, 43 includes opposing sides 49 extending between the head end 45 and the foot end 47. The patient support surface 42, 43 comprises a perimeter 51 defined by the head end 45, the foot end 47, and the opposing sides 49. The headboard 52 is positioned at the head end 45, the footboard 54 at the foot end 47, and the side rails 44, 46, 48, 50 at the opposing sides 49, as illustrated in FIG. 1 and shown schematically in FIG. 9.

The patient support system 28 comprises the user interface 110 configured to receive input from the user, and the display 112 configured to display user menus. In an exemplary embodiment, the user menus comprise indicia 116 representative of the operational devices 70-90 of the patient support apparatus 30. In some embodiments, the user menus comprise options, items, instructions, or other output or information (see FIGS. 11A and 11B).

The patient support system 28 comprises the controller 102 in communication with the user interface 110 and the display 112. The patient support apparatus 30 may comprise the control system 100 configured to control operational devices 70-90 of the patient support apparatus 30.

The user interface 110, and in many cases the display 112, are positionable at a position in proximity to the patient support apparatus 30. The patient support system 28 comprises a locating system 132 configured to determine the position of the user interface 110 (and the display 112, if applicable) with respect to the patient support apparatus 30. The locating system 132 is in communication with the controller 102 (FIG. 2) and configured to generate and transmit a position input signal based on the position of the user interface 110. The controller 102 is configured to receive the position input signal from the locating system 132. The controller 102 is further configured to determine a position-based user menu 134 based on the position input signal. The controller 102 generates an updated display output signal representative of the position-based user menu 134 and transmits the updated display output signal to the display 112 to display the position-based user menu 134.

In one exemplary embodiment, the position of the user interface 110, as determined by the locating system 132, is with respect to the head end 45, the foot end 47, and/or the opposing sides 49 of the patient support surface 42, 43. At least two of the head end 45, the foot end 47, and the opposing sides 49 are associated with a different position input signal such that the position-based user menu 134 is based on the position of the user interface 110 proximate the head end 45, the foot end 47, and the opposing sides 49. For example, should the user interface 110 be positioned proximate the head end 45, the position input signal may be such that the position-based user menu 134 comprises indicia 116 representative of the patient lifting device 70 (e.g., buttons B1 and B2 of FIG. 3). For another example, should the user interface 110 be positioned proximate one of the opposing sides 49, the position input signal may be different such that the position-based user menu 134 comprises indicia 116 representative of the patient turning device 74 (e.g., buttons B4 and B5 of FIG. 3).

Figure 9:
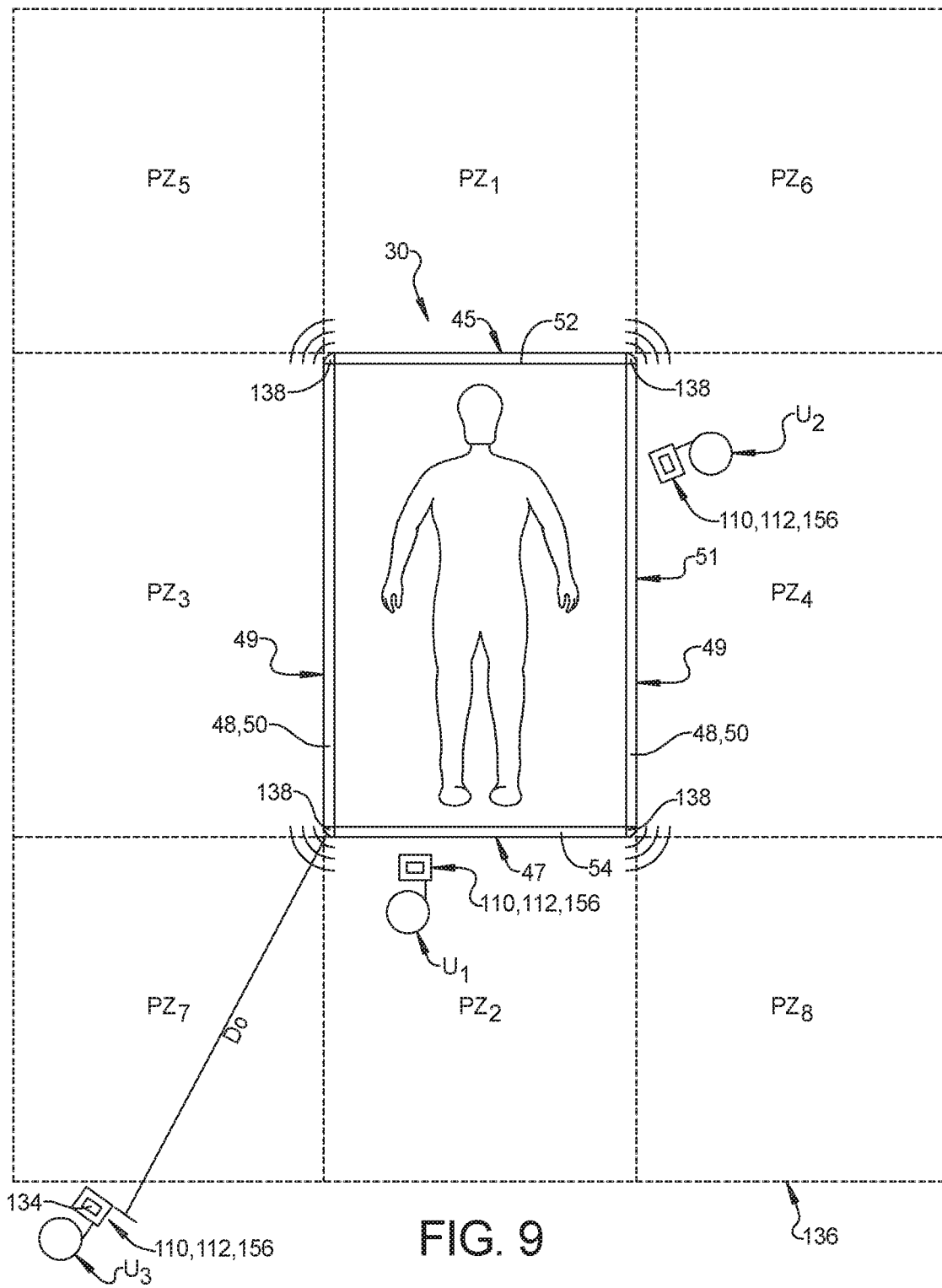
FIG. 9 is a plan view of the patient support apparatus of FIG. 1 with a schematic representation of proximate position zones to facilitate a determination of the position of the user interface in proximity to the patient support apparatus.

The position of the user interface 110 with respect to the patient support apparatus 30 may be determined with the locating system 132 in any suitable manner. FIG. 9 shows one exemplary embodiment with each of the head end 45, the foot end 47, and the opposing sides 49 associated with one of a plurality of proximate position zones PZ1-PZ8. Proximate position zone PZ1 is associated with the head end 45, proximate position zone PZ2 is associated with the foot end 47, and proximate position zones PZ3, PZ4 are associated with the opposing sides 49. In the exemplary embodiment of FIG. 9, the associated proximate positions zones PZ1-PZ4 are adjacent to and extend generally away from the patient support apparatus 30. Position proximate zones PZ5-PZ8 may be at least partially between by adjacent proximate positions zones PZ1-PZ4, as illustrated in FIG. 9, such that the patient support apparatus 30 is bounded by the proximate position zone PZ1-PZ8. The proximate position zones PZ1-PZ8 may extend infinitely away from the patient support apparatus 30, or extend for a predetermined distance 136 away from the patient support apparatus 30. The present disclosure contemplates a fewer or greater number of proximate position zones than shown in FIG. 9. For example, the proximate position zones PZ3, PZ4 associated with the opposing sides 49 may be subdivided into additional zones.

To determine the position of the user interface, the locating system 132 may comprise one or more sensors 138 configured to wirelessly detect the user interface 110. Wireless detection means such as Wi-Fi, Bluetooth, other radiofrequency (RF) communication protocols, and the like, are well known to those having skill in the art. In the illustrative embodiment of FIG. 9, the sensors 138 are coupled at each of the corners of the patient support apparatus 30, but any suitable number and position of the sensors 138 is contemplated. The user interface 110 and the display 112 may be integrated on the mobile device 156 configured to be wirelessly detected by the sensor(s) 138. The sensors 138 may also be configured to require docking of the mobile device, pendant, or other user interface 110 device to the patient support apparatus 30. In this case, the sensors 138 may be proximity switches, limit switches, hall-effect sensors, or simple electrical circuits. The locating system 132 generates the position input signal based on the position of the mobile device as detected by the sensor(s) 138.

The position input signal is based on the position of the user interface 110 within one of the proximate position zone PZ1-PZ8. At least two of the position proximate zones PZ1-PZ8 are associated with a different position input signal. FIG. 9 shows three users U1-U3 each holding the mobile device 156 such as a touchscreen 113 embodying the user interface 110 and the display 112. User U1 is standing within position proximate zone PZ2. The locating system 134 determines the user interface 110 is within the position proximate zone PZ2 and generates the position input signal based on the position of the user U1. The locating system 134 transmits the position input signal to the controller 102.

Based on the received position input signal, the controller 102 determines the position-based user menu 134. In one exemplary embodiment, the position-based user menu 134 comprises indicia 116 representative of the operational devices 70-90 of the patient support apparatus 30 and/or other suitable devices contemplated by the present disclosure. At least some of the operational devices 70-90 represented as indicia 116 on the position-based user menu 134 are associated with the position of the user interface 110 such that the display 112 displays indicia 116 most desirable to the user based on his or her position in proximity to the patient support apparatus 30. Since the user U1 is positioned within position proximate zone PZ2 at the foot end 47, the position-based user menu 134 may comprise indicia 116 representative of the bed length extension device 80 or any other suitable one of the operational devices 70-90 of the patient support apparatus 30. User U2 is positioned at one of the opposing sides 49 of the bed, and more particularly within position proximate zone PZ4. Based on the position input signal from the locating system 132, the controller 102 may determine that the position-based user menu 134 comprises indicia 116 (e.g., buttons B4 and B5) representative of the patient turning device 74 or any other suitable one of the operational devices 70-90 of the patient support apparatus 30.

Figure 11B:
FIG. 11B is another position-based output comprising a lower limb observation chart.

In another exemplary embodiment, the controller 102 is configured to determined position-based output 142 based on the position of the user interface 110 in proximity to the patient support apparatus 30. The position-based output 142 may comprise selectable options, written or graphical instructions, or other information. Alternatively, the position-based output 142 may comprise the user menus 114 having indicia 116 representative of the operational devices 70-90 of the patient support apparatus 30. FIGS. 11A and 11B each show an exemplary position-based output 142. FIG. 11A is an upper limb observation chart, and FIG. 11B is a lower limb observation chart. The observation charts of FIGS. 11A and 11B are often utilized by caregivers when performing physical examinations of the upper and lower extremities, respectively. Thus, it would be beneficial for the display 112 to display the position-based output 142 of FIG. 11A when the user interface 110, and more particularly the user, is in a suitable position to perform the upper extremity examination. Likewise, it would be beneficial for the display 112 to display the position-based output 142 of FIG. 11B when the user interface 110, and more particularly the user, is in a suitable position to perform the lower extremity examination. The user may complete the observation charts while performing the physical examinations of the upper and/or lower extremities. The concept may be extended to examinations of other body systems (e.g., neurologic observation chart when user interface 110 is positioned at the head end 45) or any other position-based items, instructions, and/or operations.

In an exemplary embodiment, the locating system 134 generates a first position signal based on a first position of the user interface in proximity to the patient support apparatus 30. The controller 102 determines a first position-based output based on the first position signal and generates a first display output signal representative of the first position-based output. The first display output signal representative of the first position-based output is transmitted to the display 112. The first position-based output is displayed on the display 112.

The user interface 110 may be moved to a second position different from the first position. For example, the user carrying the touchscreen 113 (embodying the user interface 110 (and the display 112) may walk about the patient support apparatus 30. The locating system generates a second position signal based on the second position of the user interface in proximity to the patient support apparatus 30. The controller 102 determines a second position-based output based on the second position signal and generates a second display output signal representative of the second position-based output. The second display output signal is transmitted to the display 112. The display 112 displays on the display the second position-based output based on the second display output signal.

In another exemplary embodiment, the locating system 132 may automatically detect a change in the position of the user interface 110 between the proximate position zones PZ1-PZ8. Upon detection of the change, the locating system 132 generates and transmits an updated position input signal to the controller 102. The controller 102 determines an updated position-based user menu 134, generates the updated display output signal, and transmits the updated display output signal to the display 112. The display 112 displays the updated position-based user menu 134. In the above exemplary methods, the position-based user menu 134 automatically updates as the position of the user interface 110 changes, thereby providing convenience to the user as the user moves about the patient support apparatus 30.

The user carrying the mobile device 156 may move freely about the patient support apparatus 30 with the user menus automatically updating and displaying the most relevant user menus 114 or position-based output 142 at any particular instant.

It may be further beneficial for the position-based user menu 134 to be displayed as the user approaches the patient support apparatus 30. The position-based user menu 134 and/or position-based output may automatically be displayed on the display 112 once the user interface 110 is within a predetermined distance. With continued reference to FIG. 9, the predetermined distance 136 is shown as a boundary enveloping the proximate position zones PZ1-PZ8. The position of the user interface 110 includes a distance of the mobile device 156 (embodying the user interface 110 and the display 112) from the patient support apparatus 30. One exemplary distance DO shown in FIG. 9 comprises the distance from one of the sensors 138 at a corner of the patient support apparatus 30 to the mobile device carried by the user U3. The distance DO is greater than the predetermined distance 136 shown in FIG. 9. The locating system 132 determines the distance of the user interface 110 from the patient support apparatus 30. When the distance is within the predetermined distance 136, as determined by the locating system 132, the locating system 132 generates the position input signal (e.g., one of the first or second position signals). Effectively, as the user U3 passes through the boundary comprising the predetermined distance 136, the position-based user menu 134 and/or position-based output 142 is automatically determined. In one embodiment, the position-based user menu 134 and/or position-based output 142 is automatically determined and displayed once the distance is within the predetermined distance 136.

When the distance is not within the predetermined distance 136, the locating system 132 may provide a non-proximity signal to the controller 102. In response to the non-proximity signal, the controller 102 may be configured to transmit an inactive display output signal such that the display is in an inactive state. For example, the inactive state may comprise a "home screen" or "screen saver" being displayed on the display 112, a default user menu, or any other information other than the position-based user menu 132. The present disclosure further contemplates that the controller 102 may be configured to lock or disable the user interface 110 in response to receiving the non-proximity signal from the locating system 132. Locking or disabling the user interface 110 when the mobile device 156 is not within the predetermined distance 136 is a safety feature that ensures that the input to the mobile device corresponds to the appropriate patient support apparatus 30. In other words, the user interface 110 is required to be positioned sufficiently proximate the patient support apparatus 30 to control the operational devices 70-90 of the same.

Figure 10A:
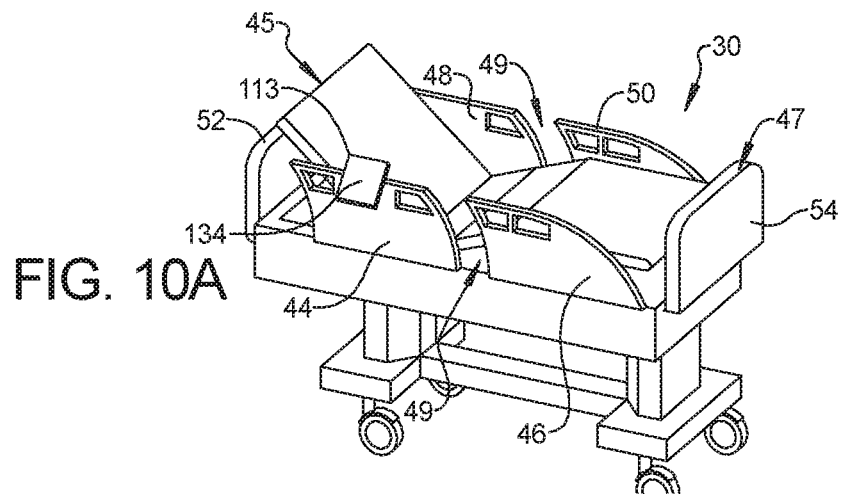
FIG. 10A is a perspective view of the patient support apparatus of FIG. 1 with a touchscreen comprising the user interface and the display coupled to one of the side rails of the patient support apparatus.
Figure 10B:
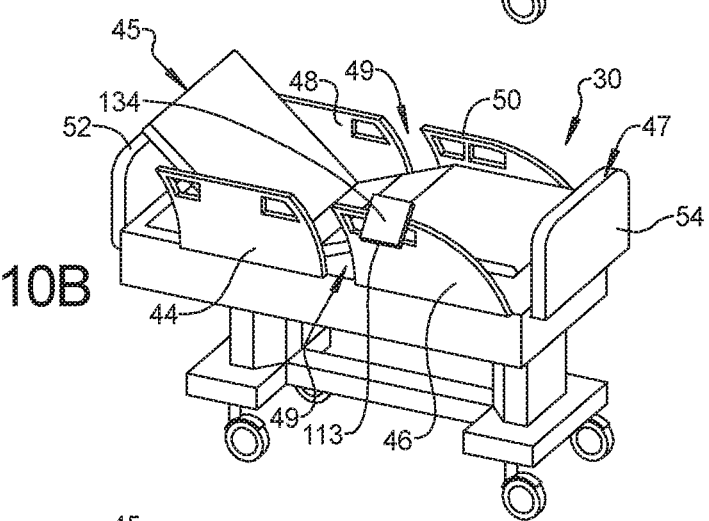
FIG. 10B is a perspective view of the patient support apparatus of FIG. 1 with the touchscreen of FIG. 10A coupled to another of the side rails of the patient support apparatus.
Figure 10C:
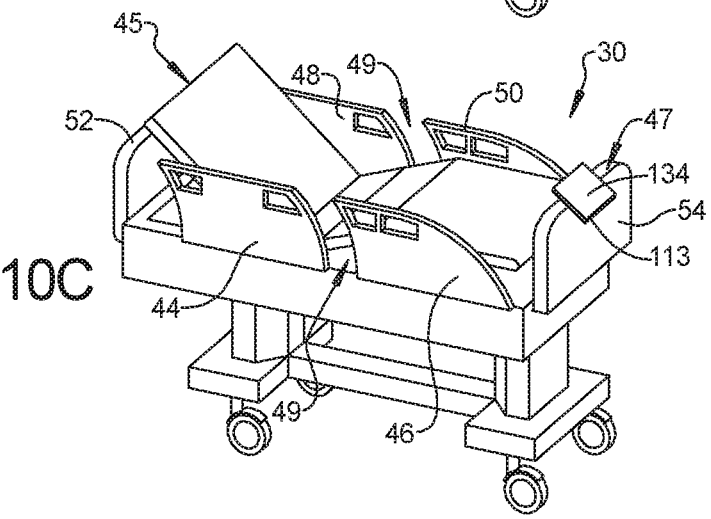
FIG. 10C is a perspective view of the patient support apparatus of FIG. 1 with the touchscreen of FIG. 10A coupled to the footboard of the patient support apparatus.

As previously described, the user interface 110 and/or the display 112 may be integrated with one or more of the side rails 44, 46, 48, 50, the headboard 52, the footboard 54, or other suitable locations. Referring now to FIGS. 10A-10C, the user interface 110 may be removably coupled with one of the side rails 44, 46, 48, 50, the headboard 52, the footboard 54, or other suitable locations. In one exemplary embodiment, one or more of the side rails 44, 46, 48, 50, the headboard 52, the footboard 54 comprise a docking port (not shown) configured to couple with the user interface 110 (and display 112) such as the touchscreen 113 of FIGS. 10A-10C.

The position-based user menu 134 and/or position-based output 142 may be based on, at least in part, to which of the side rails 44, 46, 48, 50, the headboard 52, and the footboard 54 the user interface 110 is coupled. Exemplary methods include receiving the user interface 110 coupled to one of the headboard 52, the footboard 54, and the side rails 44, 46, 48, 50. The controller 102 determines the first or second position-based outputs based on which one of the one of the headboard 52, the footboard 54, and the side rails 44, 46, 48, 50 the user interface 110 is coupled.

In one exemplary embodiment, the user interface 110 and the display 112 are integrated on the touchscreen 113 adapted to be docked to at least one of the headboard 52, the footboard 54, and the side rails 44, 46, 48, 50. FIG. 10A shows the touchscreen 113 coupled to an upper left side rail 46 (when viewed in plan) of the patient support apparatus 30. Should the user be interacting with the patient supported on the patient support apparatus 30 and/or using the touchscreen 113 in the position of FIG. 10A, it may be beneficial for the position-based user menu 134 to comprise indicia 116 of a particular one or more of the operational devices 70-90 of the patient support apparatus 30 (e.g., the patient raising device 70). Additionally or alternatively, it may be beneficial to display particular position-based output 142 such as the upper extremity observation chart of FIG. 11A or other pertinent or desired information. FIG. 10B shows the touchscreen coupled to a lower left side rail 44 (when viewed in plan) of the patient support apparatus 30. Based on the coupled position, it may be beneficial for the position-based user menu 134 to comprise indicia 116 of another one or more of the operational devices 70-90 of the patient support apparatus 30, and/or particular position-based output 142 (e.g., the lower extremity observation chart of FIG. 11B). FIG. 10C shows the touchscreen coupled to the footboard 54 of the patient support apparatus 30. Based on the coupled position, it may be beneficial for the position-based user menu 134 to comprise indicia 116 of another one or more of the operational devices 70-90 of the patient support apparatus 30, and/or particular position-based output 142 (e.g., the lower extremity observation chart of FIG. 11B).

The dockable touchscreen described herein may be utilized alternatively or in addition to the proximate position zones PZ1-PZ8 and other suitable methods for determining the position of the touchscreen 113 with respect to the patient support apparatus 30. For example, the position-based user menu 134 and/or the position-based output 142 may automatically be displayed on the touchscreen 113 when the touchscreen 113 is within the predetermined distance 136. The content, arrangement, scaling, and the like, of the position-based user menu 134 and/or the position-based output 142 may be based on the position of the touchscreen 113 within one of the proximate position zones PZ1-PZ8. The touchscreen 113 may subsequently be docked or otherwise coupled to the patient support apparatus 30. The position-based user menu 134 and/or the position-based output 142 may be updated consistent with the methods described herein, or remain the same based on where the touchscreen 113 is docked or coupled to the patient support apparatus 30. The present disclosure further contemplates the position-based user menu 134 and/or the position-based output 142 may be utilized in addition to the customized user menu 120b, 122b, 124b previously described herein.

Figure 14:
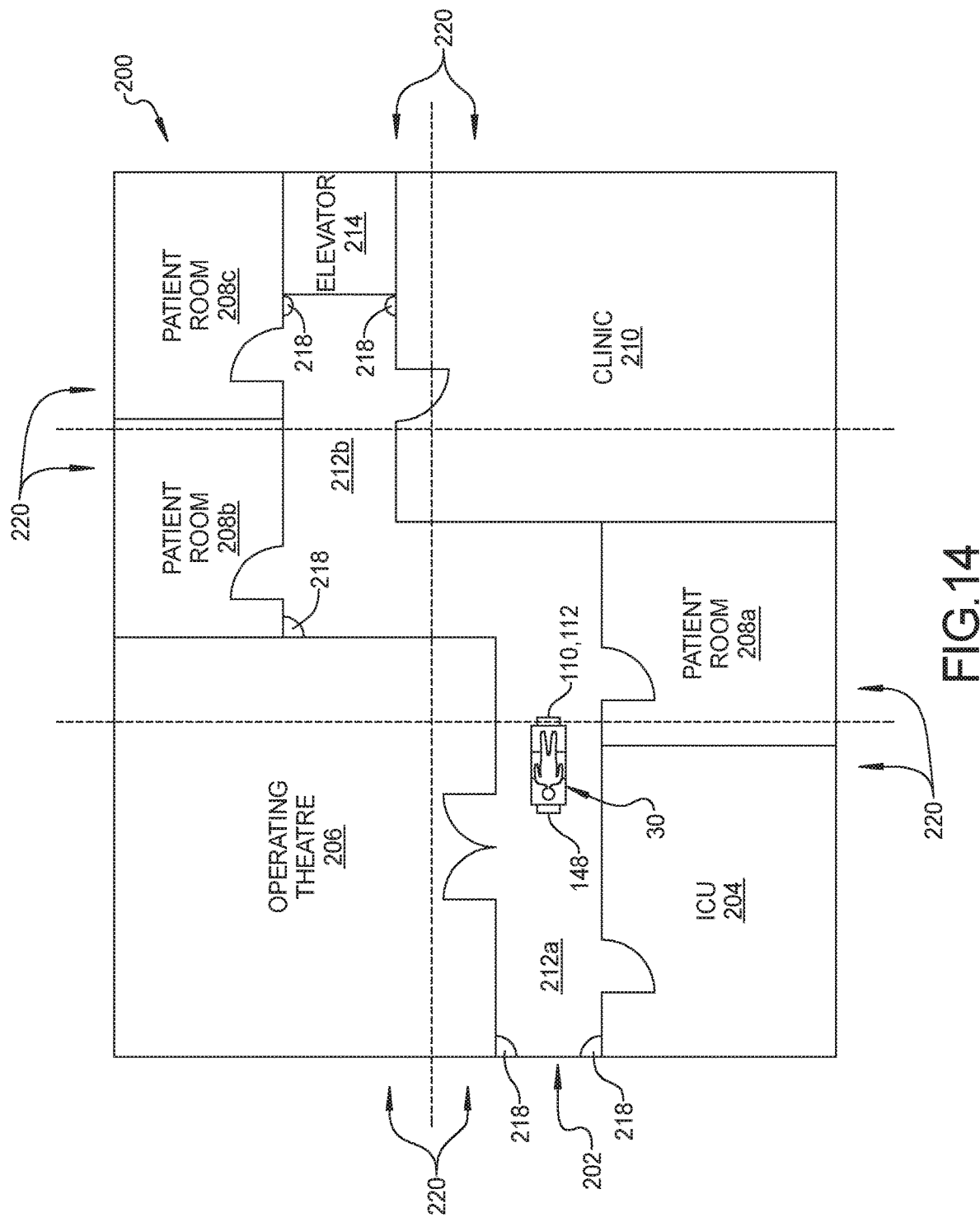
FIG. 14 is a schematic representation of a facility comprising a medical floor with the patient support apparatus of FIG. 1 positioned within the facility.

The customized and/or adaptive user menus may be extended to the patient while supported by the patient support apparatus 30. Referring to FIG. 14, the patient support apparatus 30 is shown supporting the patient P on the patient support surface 43. The patient P is holding the mobile device 156 such as a tablet, smartphone, or the like.

In many respects the mobile device 156 of the present embodiment operates in the same manner as those described throughout the present disclosure; i.e., the mobile device 156 comprises the touchscreen 113 configured to display indicia, output, or other information, and the user interface 110 configured to receive input from the patient P. Customized and/or adaptive user menus and other virtual objects (e.g., mobile applications) may be displayed with the mobile device 156 based, at least in part, on the patient's P interaction with features of the patient support apparatus 30 while being supported by the same.

Figure 12:
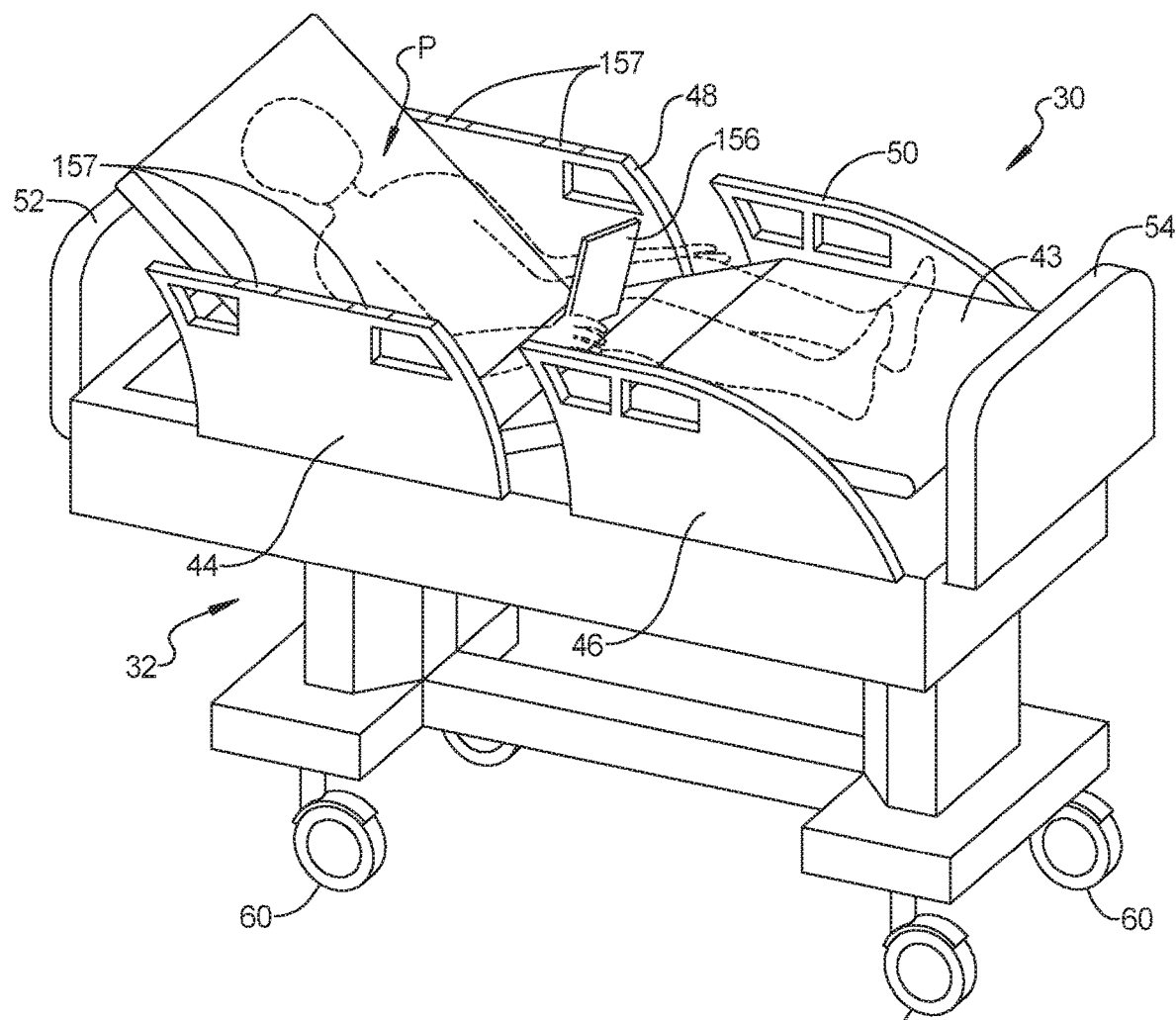
FIG. 12 is perspective view of a patient support apparatus of FIG. 1 supporting the patient with proximity sensors coupled to the patient support apparatus.
Figure 13:
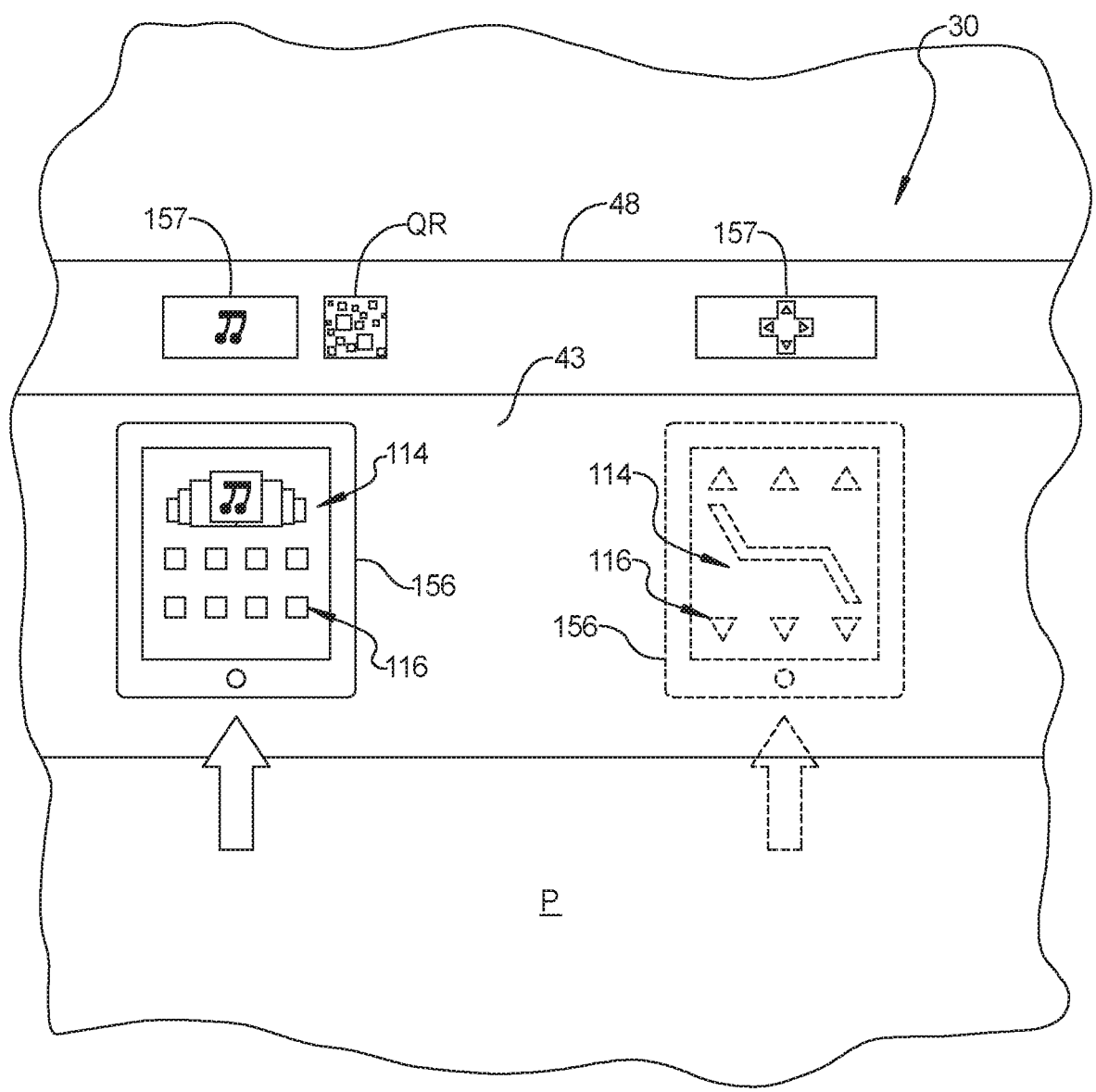
FIG. 13 is a partial plan view of the patient support apparatus of FIG. 12 showing the proximity sensors coupled to a side rail of the patient support apparatus. Mobile devices are positioned within a suitable proximity of the proximity sensors to establish short-range wireless communication.

In certain embodiments, the patient support apparatus 30 comprises proximity sensors 157 coupled to the side rails 44, 46, 48, 50. The embodiment of FIG. 14 shows two proximity sensors 157 coupled to each of the upper side rails 44, 48. Additionally or alternatively, the proximity sensors 157 may be coupled to other suitable structures of the patient support apparatus 30 such as the lower side rails 46, 50, the headboard 52, and/or the footboard 54. FIGS. 12 and 13 show the proximity sensors 157 positioned atop the upper side rails 44, 48, but positioning the proximity sensors 157 on the patient-side surface of the side rails 44, 46, 48, 50 is also contemplated. The proximity sensors 157 may harness short-range wireless technology to establish communication with the mobile device 156 being held by the patient. In one embodiment, the proximity sensors are near-field communication (NFC) tags that uses magnetic field induction (e.g., wireless connectivity standard (Ecma-340, ISO/IEC 18092)) to enable communication between the tag and the mobile device 156 when touched together or brought within a few centimeters (e.g., four centimeters) of each other. The proximity sensors 157 are in communication with the controller 102 through wired or wireless means commonly known in the art.

By positioning the mobile device 156 within a suitable proximity of the NFC tags, the patient P may be automatically presented with the user menus, output, or other information without requiring further navigation on the mobile device 156. Referring now to FIG. 13, one exemplary operation of the present embodiment will be described. The patient P is supported on the patient support surface 43 of the patient support apparatus 30. The patient is holding the mobile device 156 comprising a tablet. Two proximity sensors 157 comprising NFC tags are coupled to the upper right side rail 48 (when viewed in plan in FIG. 12). In one embodiment, each of the NFC tags is associated with different operational features 70-90 of the patient support apparatus 30. For example, one of the NFC tags may be associated with the entertainment device 88, and another associated with the deck adjustment device 84. FIG. 13 shows the patient P positioning the mobile device 156 (in solid) within the suitable proximity with the NFC tag associated with the entertainment device 88 as indicated by the music note insignia. Once near-field communication is established, the mobile device 156 is configured to display the user menu 114 comprising indicia 116 representative of the operational features associated with the entertainment device 88.

The patient P may interact with the user menu 114 as desired to control operational features such as the music and television, to browse the Internet on the mobile device 156, and the like. The user menu 114 associated with the entertainment device 88 may remain displayed on the mobile device 156 until the patient P navigates away from the same, or until the mobile device 156 is brought into proximity with another one of the NFC tags. In certain embodiments, after the mobile device 156 is brought into proximity of one of the NFC tags, the mobile device 156 continues to display the user menu 114 comprising indicia 116 representative of the operational features after the patient P navigates away from the same.

The patient P, for example, wishes to adjust one or more sections of the patient support apparatus 30. Another one of the proximity sensors 157 comprising an NFC tag is associated with the deck adjustment device 84. The patient P positions the mobile device 156 (in phantom) into proximity with the NFC tag associated with the deck adjustment device 84 as indicated by the directional keypad insignia. Once near-field communication is established, the mobile device 156 is configured to display the user menu 114 comprising indicia 116 representative of the operational features associated with the deck adjustment device 84. The patient P may interact with the user menu 114 as desired to control operational features such the angle of the fowler section, the angle of the leg section, the height of the seat section, and the like.

The resulting displayed output from each of the proximity sensors 157 may be predefined. The association between certain proximity sensors 157 and specific output may be non-modifiable and perhaps permanently demarcated with an insignia (e.g., the music note), and stored in the non-transitory memory 130 for access by the controller 102. Alternatively, the association between the proximity sensors 157 and corresponding output may be assigned or customized by a user thorough software or other means commonly known in the art. The association may be modified, reprogrammed, and the like, based on the specific patient, the facility, and/or any other circumstances.

Mobile applications (hereinafter "apps") may be integrated into the present embodiment. In addition or as an alternative to user menus 114 being displayed on the mobile device 156 when the patient P positions the mobile device 156 within the suitable proximity to the proximity sensors 157, the present embodiment contemplates an app may be opened. For example, the Apple iTunes® app may be opened automatically once the patient P positions the mobile device 156 in suitable proximity to the NFC tag of FIG. 13 with the music note insignia. In another example, there may be an app designed and customized to the operational functions of the patient support apparatus 30 supporting the patient (e.g., the particular model). The app may be opened once the patient P positions the mobile device 156 in suitable proximity to the corresponding NFC tag. Should the mobile device 156 not have the particular app installed, the system may be configured to open to the proper e-commerce location to purchase and/or install the app (e.g., Apple AppStore®, Google Play®, etc.). In practical effect, the resulting arrangement includes the mobile device 156 being used as a remote control for the patient support apparatus 30.

The present disclosure contemplates the use of quick response (QR) codes as an alternative or in addition to near-field communication. In some instances, the mobile device 156 may not be configured for near-field communication and the scanning of a QR code may be easier for the patient P. As shown in FIG. 13, a QR code is positioned on the upper right side rail 48 (when viewed in plan in FIG. 12). In the present example, the QR code is positioned adjacent the NFC tag with the music note insignia and therefore may be configured to similarly result in the user menu 114 associated with the entertainment device 88 (or desired app) being displayed on the mobile device 156 when scanned by the mobile device 156. The patient P, using a camera of the mobile device 156, scans or captures a picture of the QR code. A signal is sent from the mobile device 156 to the controller 102. In response, the controller 102 determines the corresponding output and transmits an output signal to the mobile device 156 to display the same. Whether the resulting displayed content is a customized user menu or an app, which of the operational functions that are controllable by the patient P may be predefined, ensuring patient safety and control over the patient environment while providing the patient with a degree of autonomy.

In many respects each of the proximity sensors 157 is coupled to the patient support apparatus 30 at a discrete position. In certain embodiments, the positions of the proximity sensors 157 is related to the corresponding output provided when the mobile device 156 is positioned within a suitable proximity. For example, the locating system 132 may comprise the proximity sensors 157. The patient support system 28 is configured to generate with the locating system 132 position-based signals based on positions of the mobile device 156 with respect to the patient support apparatus 30 once the mobile device 156 communicates with one of the proximity sensors 157. In the exemplary embodiment of FIGS. 12 and 13, a first position may be one of the NFC tags, and a second position may be another one of the NFC tags. Each of the NFC tag may be associated with a different position-based signal. Based on the position-based signal, the controller 102 may determine a corresponding position-based output and generate a display output signal. The display output signal is transmitted to the mobile device 156 to display the position-based output on the mobile device 156. Should the patient P move the mobile device 156 into proximity with another one of the NFC tags, a different position-based signal is transmitted to the controller 102, and a different position-based output may be determined and displayed on the mobile device 156. In certain embodiments, the position-based output is based on a combination of content associated with two or more of the NFC tags. Should the mobile device 156 be within a suitable proximity of two of the NFC tags each associated with a different position-based signal, the signals may be transmitted to the controller 102. The position-based output comprises a combination of the different position-based signals. For example, the position-based output may comprise a combination of different operational features 70-90 of the patient support apparatus 30, such as the entertainment device 88 and/or the deck adjustment device 84 (see FIG. 13). The display output signal is transmitted to the mobile device 156 to display the position-based output on the mobile device 156.

The present disclosure further contemplates that embodiments of the patient support system 28 using short-range wireless communication to generate customized and/or adaptive user menus may be utilized in connection with one or a combination of the location-based user menu 144, the customized user menu 120b, 122b, 124b, the position-based user menu 134, the position-based output 142, and the identification-based user menu 154. As one non-exhaustive example, the output associated with one of the NFC tags and/or QR codes may be based, at least in part, on the usage characteristics of the user (e.g., most frequently selected operational function, time of day, etc.), the identification of the user (e.g., patient, doctor, etc.), and the like. These characteristics are stored in the non-transitory memory 130 accessible by the controller 102 such that when the mobile device 156 is positioned within the suitable proximity to the NFC tag (and/or the QR code is captured), the optimal user menu, output, information, or app is presented to the patient P.

Those having skill in the art readily appreciate that patient support apparatuses are often transportable between locations within a facility, particularly a medical setting such as a hospital. The operational devices 70-90 of the patient support apparatus 30 most frequently utilized may be based on the location of the patient support apparatus 30 within the facility. Likewise, the most desirable output to be displayed on the display 112 may be based on the location of the patient support apparatus 30 within the facility. The patient support system 28 of the present disclosure provides location-based user menus based on a location of the patient support apparatus 30 within the facility.

Referring to FIG. 14, a schematic representation of a facility 200 is provided. The facility 200 may comprise a floor from a hospital, including an entrance 202, an intensive care unit (ICU) 204, operating theatre 206, patient room 208a-c, and a clinic 210. Two main corridors 212a, 212b access each of the areas. The medical facility 200 further includes an elevator 214 to move between different floors. FIG. 14 shows the patient support apparatus 30 positioned within one of the corridors 212a. The patient support apparatus 30 comprises the control system 100 configured to control the operational devices 70-90 of the patient support apparatus 30. The patient support system 28 comprises the user interface 110 configured to receive input from the user, and the display 112 configured to display user menus 114 comprising indicia 116 representative of the operational devices 70-90 of the patient support apparatus 30.

The patient support system 28 further comprises a tracking system 146 configured to determine a location of the patient support apparatus 30 within the facility 200 and generate and transmit a tracking input signal. In one exemplary embodiment, the tracking system 146 comprises a locator network 216 within the facility 200. The tracking system 146 may further comprise a tracking device 148 configured to be coupled to the patient support apparatus 30 with the locator network 216 configured to detect the tracking device 148. The locator network 216 comprises a plurality of sensors 218 configured to cooperatively detect and determine the location of the patient support apparatus 30 (e.g., the tracking device 148) within the facility 200. In the exemplary embodiment illustrated in FIG. 14, the tracking device 148 is coupled to the headboard 52 of the patient support apparatus 30, but the present disclosure contemplates any suitable coupling position and means. The tracking device 148 may be integrated with the patient support apparatus 30 or retrofit (e.g., a removably coupled beacon) on the patient support apparatus 30. The wireless detection of the patient support apparatus 30 with the tracking system 146 are well known to those having skill in the art. Exemplary indoor positioning systems (IPS) utilize Wi-Fi (WPS), Bluetooth™, ZigBee, other radiofrequency (RF) protocols, and other optical, magnetic, radio and/or acoustic technologies.

The patient support system 28 comprises the controller 102, the tracking system 146, the user interface 110, and the display 112. The controller 102 is configured to receive the tracking input signal transmitted from the tracking system 146. In an exemplary embodiment, the controller 102 receives the tracking input signal based on a location of the tracking device 148 within the facility 200 as detected by the locator network 216. Based on the tracking input signal, the controller 102 is configured to determine a location-based user menu 144 and generate a display output signal. The controller 102 is configured to transmit the display output signal to the display 112 to display the location-based user menu 144.

Figure 15A:
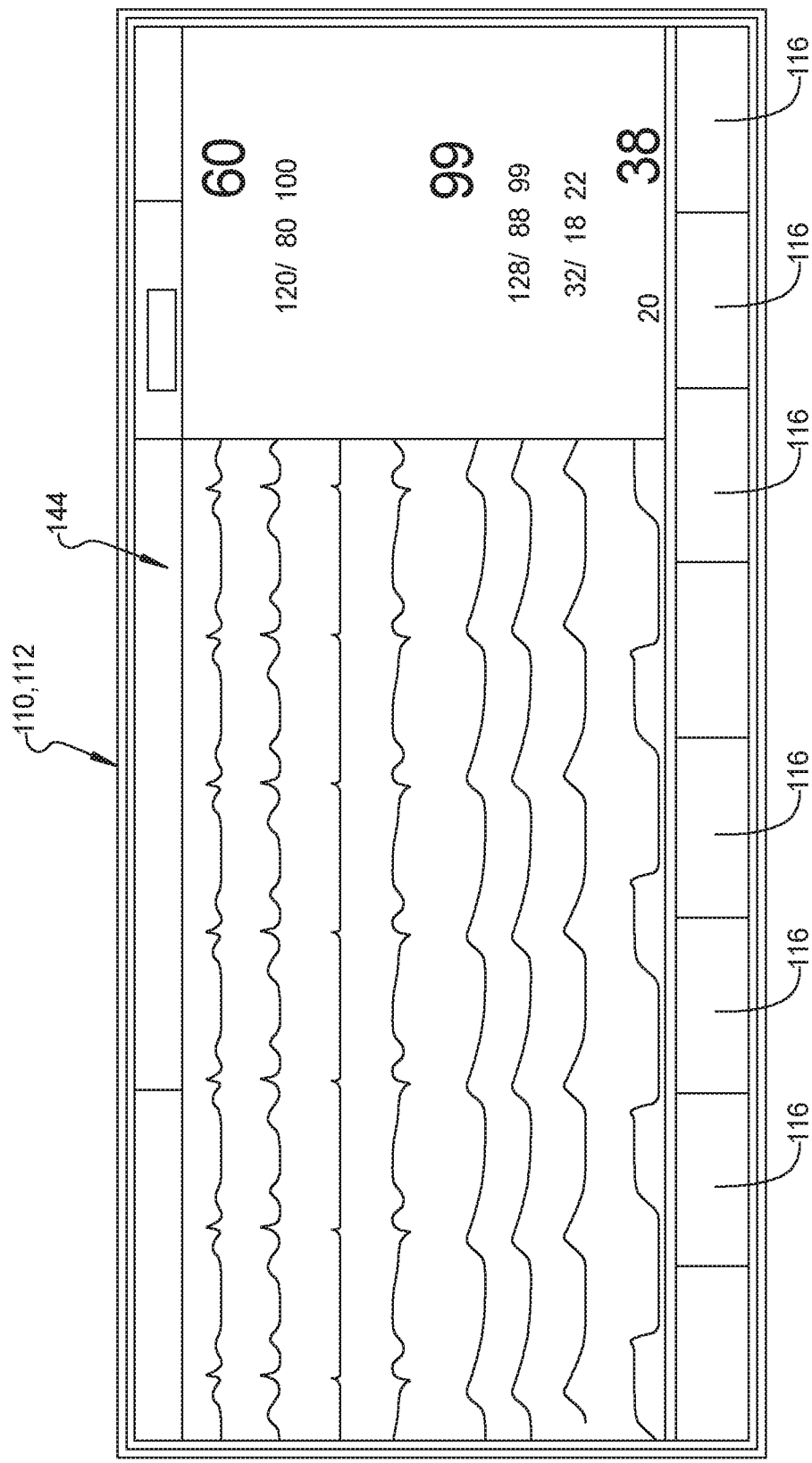
FIG. 15A is a location-based user menu comprising electrocardiographic output.
Figure 15B:
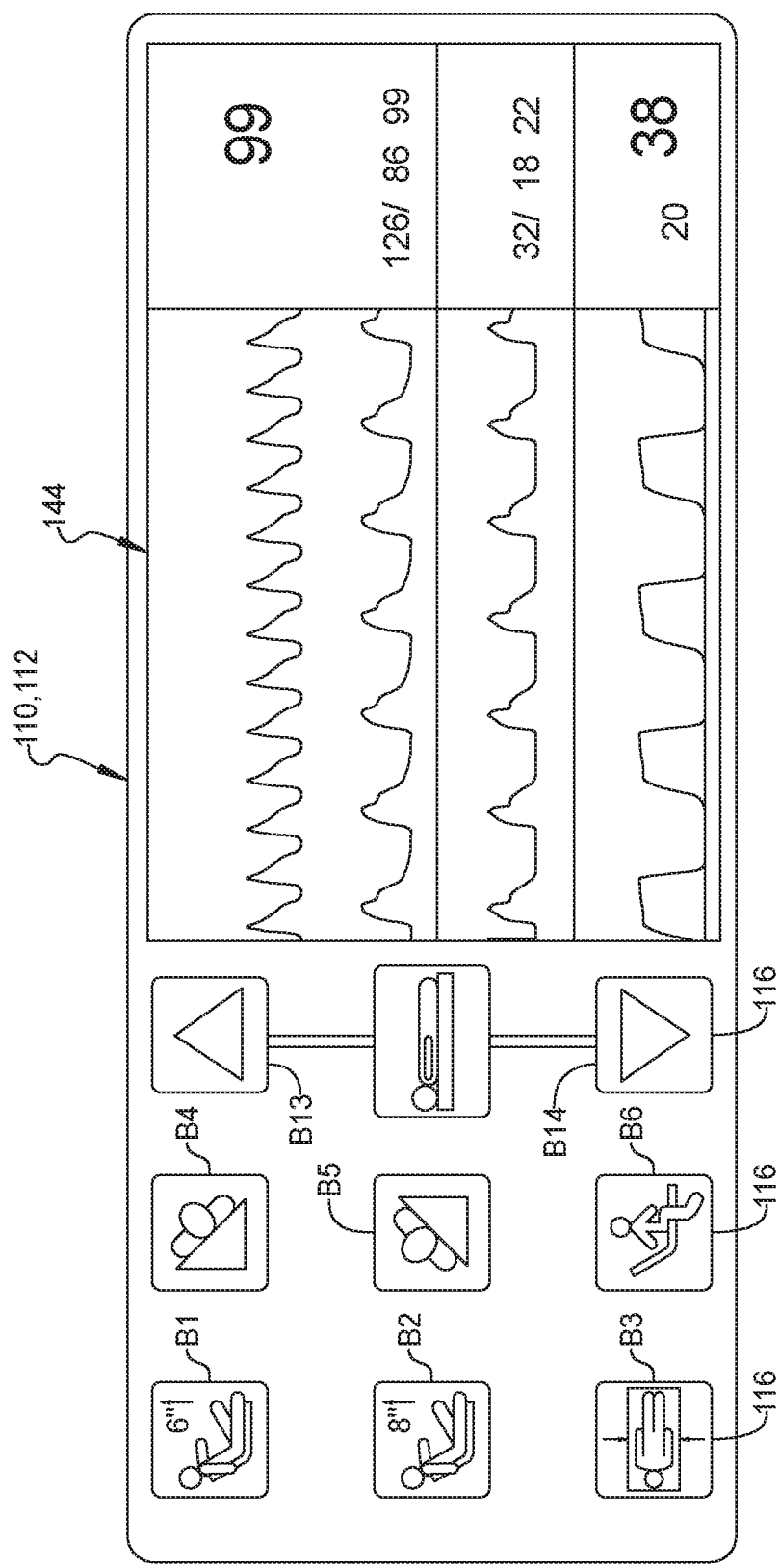
FIG. 15B is another location-based user menu comprising electrocardiographic output and indicia representative of the operations of the patient support apparatus of FIG. 1.

FIGS. 15A and 15B each show a location-based user menu 144. The user interface 110 and the display 112 are integrated into the touchscreen 113 and/or mobile device 156. The location-based user menu 144 of FIG. 15A comprises output of an electrocardiogram (EKG) and indicia 116 representative of the features of the EKG. FIG. 15B shows the location-based user menu 144 comprising indicia 116 representative of operational devices 70-90 of the patient support apparatus 30, and the output of the EKG.

Relative to FIG. 15B, the location-based user menu 144 of FIG. 15A provides more information directed to the EKG and in greater detail. Further, the indicia 116 of the location-based user menu 144 of FIG. 15A is directed to navigating the EKG-related menus. The location-based user menu 144 of FIG. 15A may be particularly appropriate to display at the entrance 202 of the facility 200, the ICU 204, and/or the operating theatre 206, as those locations often require detailed information regarding the patient's cardiovascular functioning. By contrast, the location-based user menu 144 of FIG. 15B provides scaled-down and lesser information directed to the EKG, and also provides indicia 116 representative of operational devices 70-90 of the patient support apparatus 30. The exemplary location-based user menu 144 of FIG. 15B may be particularly appropriate to display in the patient rooms 208a-c, the clinic 210, and/or the corridor 212a, 212b, as the patient is often stabilized in those locations and more likely to need, for example, the patient raising device 70 (buttons B1 and B2), the patient turning device (buttons B4 and B5), and the like. FIGS. 15A and 15B are non-limiting examples of the location-based user menu 144. The location-based user menu 144 may comprise any indicia, output, or other information responsive to the location of the user interface 110 within the facility 200.

In one exemplary operation, the patient support apparatus 30 approaches the facility 200 supporting a patient. Proximate to the entrance 202 of the facility 200, the tracking system 146 generates a tracking signal based on the location of the patient support apparatus 30 within the facility 200. The controller 102 determines a location-based output based on the tracking signal. Proximate to the entrance 202 of the facility 200, the location-based output may be an emergent intake examination chart to use as guidance and recording of key aspects such as neurologic functioning, temperature, mental status, and the like. Such a chart may take a form similar to the upper and lower extremities examination charts of FIGS. 11A and 11B. Additionally or alternatively, should the patient be coupled to an electrocardiograph (during transport or otherwise) or other diagnostic tool, the location-based output may at least include information transmitted from the EKG or diagnostic tool. A first display output signal is transmitted to the display 112 based on the location-based output. The location-based user menu 144 is displayed on the display 112 based on the first display output signal. For example, as the patient enters through the entrance 202 of the facility 200, the location-based user menu 144 of FIG. 15A is displayed on the display 112. Having the most desirable information displayed on the display 112, particularly in situations such as emergent admission to the hospital, is beneficial to attending medical professionals.

The location-based user menu 144 is updated on the display 112 when the patient support apparatus 30 is in a second location within the facility 200 different from the first location. The tracking system 146 generates a second tracking signal based on the second location. The controller 102 determines the updated location-based user menu 144 based on the second tracking signal, and transmits to the display 112 a second display output signal representative of the updated location-based user menu 144. The updated location-based user menu 144 is displayed on the display 112. In many instances, the updated location-based user menu 144 may be the same as the location-based user menu 144. For example, should the patient be transported to the second location such as, for example, the ICU 204 or the operating theatre 206, it may be beneficial to continue to display the location-based user menu 144 of FIG. 15A. Should the patient be transported to the second location such as, for example, the patient rooms 208a-208c or the clinic 210, it may be beneficial to display the location-based user menu 144 of FIG. 15B.

As previously described, the tracking system 146 is configured to determine the location of the patient support apparatus 30 within the facility 200, and the controller 102 is configured to determine the location-based user menu 144 based on the location. In one exemplary embodiment, the facility 200 comprises a plurality of predefined sectors 220. Each of the predefined sectors 220 may be associated with a different location-based user menu 144. For example, the predefined sectors 220 may be associated with the ICU 204, the operating theatre 206, the patient room 208a-208c, the corridor 212a, 212b, and the facility entrance 204. The bounds of the rooms define the sectors 220 such that when the patient support apparatus 30 is positioned within the room, the location-based user menu 114 may be unique to that predefined sector 220. For another example, the predefined sectors 220 may be associated with a spatial grid with each of the sectors 220 corresponding to a cell of the grid. Other suitable means for defining the sectors 220 are contemplated by the present disclosure. In some embodiments, the non-transitory memory 130 may be configured to store a floorplan of the medical facility 200. The stored floorplan may identify the predefined sectors 220. The floorplan may be uploaded or otherwise transmitted to the non-transitory memory 130. The stored floorplan may be updated as desired by an individual utilizing software designed for the same. In other words, the individual may selectively designate the predefined sectors 220 of the stored floorplan, or develop a floorplan with the predefined sectors 220. At least two of the predefined sectors 220 are associated with a different location input signal such that the location-based user menu 144 automatically updates as the location of the patient support apparatus 30 moves between predefined sectors 220 within the facility 200. For example, the predefined sectors 220 are associated with the ICU 204, the operating theatre 206, the patient room 208a-208c, the hallway 212a, 212b, and the facility entrance 204. The tracking system 216, via the sensors 218 or otherwise, may continuously track the tracking device 148 of the patient support apparatus 30. The location-based user menu 144 may change from that of, for example, FIG. 15A to FIG. 15B as the patient support apparatus 30 moves from the ICU 204 to the patient room 208a-208c.

The location-based user menu 144 and the updated location-based user menu each may comprise indicia 116 representative of the operational devices 70-90 of the patient support apparatus 30. The location-based user menu 144 may comprise indicia representative of a first subset of the operational devices 70-90, and the updated location-based user menu may comprise indicia 116 representative of a second subset of the operational devices 70-90. In some cases, the first subset of indicia 116 is at least partially different than the second subset of indicia 116. For example, the location-based user menu 144 when the patient support apparatus 30 is within the clinic 210 may include the first subset of indicia 116 representative of at least the patient turning device 74 (e.g., buttons B4 and B5 of FIG. 3), as caregivers may be interested in turning the patient for comfort and/or examination. The location-based user menu 144 when the patient support apparatus 30 is within the patient room 208a-208c may include the second subset of indicia 116 representative of at least the entertainment device 88 and the lighting device 90 (buttons B17 and B18 of FIG. 3, respectively), as the caregiver (or the patient) may be interested in controlling the same. The first and second subsets of indicia 116 may be predefined based on the location of the patient support apparatus 30 within the facility 200 such that, for example, the location-based user menu 144 always includes indicia 116 representative of the entertainment device 88 when the patient support apparatus 30 is within the patient room 208a-208c. The user interface 110 may receive a first user input comprising a user selection of one of the indicia 116 from the location-based user menu 144 when the patient support apparatus 30 is at the first location, and a second user input comprising a user selection of one of the indicia 116 from the updated location-based user menu when the patient support apparatus 30 is at the second location. The present disclosure also contemplates that the controller 102 may move the user interface 110 between a locked configuration and an unlocked configuration based on the location of the user interface 110 within the facility. In the locked configuration, engagement with the user interface 110 may not provide any corresponding input signal to the controller 102. Conversely, in the unlocked configuration, the user interface 110 may operate as described throughout the present disclosure. In one example, should the patient support apparatus 30 be located in the operating theatre 206 of the facility 200, the user interface 110 may be in the locked configuration so as to prevent inadvertent or unintended control of one of the operational devices 70-92. Other similar examples are considered contemplated by the present disclosure.

Exemplary methods may further comprise receiving on the user interface 110 a first user input comprising a selection of one of the indicia 116 representative of the first subset of operational devices 70-90 of the patient support apparatus 30 when the patient support apparatus is at the first location. A second user input may also be received on the user interface 110. The second user input comprises a selection of one of the indicia 116 representative of the second subset of operational devices 70-90 of the patient support apparatus 30 when the patient support apparatus is at the second location. In some cases, the second subset is at least partially different than the first subset. In other words, indicia 116 representative of different operational devices 70-90 of the patient support apparatus 30 may be displayed on the display at different locations within the facility 200. The first and second subsets of the operational devices 70-90 may be predefined based on the location of the patient support apparatus 30 within the facility 200. Additionally or alternatively, the present disclosure further contemplates the location-based user menu 144 may be provided in addition to the customized user menu 120b, 122b, 124b, the position-based user menu 134, and/or the position-based output 142 previously described herein. In one exemplary embodiment, the first subset of the operational devices 70-90 may be based on a frequency the indicia 116 is selected at the first location of the patient support apparatus 30 within the facility 200. Thus, for example, the frequency over time the user selects indicia 116 representative of each of the operational devices 70-90 of the patient support apparatus 30 may be correlated with where the patient support apparatus 30 is within the facility 200 when the indicia 116 is selected. The correlation may be stored in the non-transitory memory 130 and utilized with the controller 102 to determine the first and second subsets of the operational devices 70-90 to comprise the location-based user menu 144 based on the location of the patient support apparatus 30 within the facility 200.

Facilitation of effective medical care typically requires tailoring treatment specifically to the patient and his or her condition. Protocols or preferred treatment modalities exist for most conditions. For example, treatment for deep venous thrombosis (DVT) often includes, among other things, elevation of the legs. Providing a patient support system with customized user menus is beneficial to facilitate improved patient care. The patient support system 28 and methods of the present disclosure provide the customized user menu based, at least in part, on identifying characteristics of the user.

The patient support system 28 comprises the patient support apparatus 30 with the control system 100 configured to control operational devices 70-90 of the patient support apparatus 30. Non-limiting examples of the operational devices 70-90 that may be controlled by the control system 100 are described throughout the present disclosure. The patient support system 28 further comprises the display 112 configured to display the user menus 114 comprising indicia 116 representative of the operational devices 70-90, and/or selectable options, written or graphical instructions, or other information.

Referring to FIG. 2, the patient support system 28 comprises an identification system 150 comprising a module 152. The identification system 150 is in communication with the controller 102. The identification system 150 is configured to determine the identification of the user and transmit an identification input signal. The user may be the patient, the caregiver, and/or any other individual directly or indirectly using the patient support apparatus 30. The identification system 150 may comprise the identifier 158 associated with user and detectable by the module 152. In an exemplary embodiment, the identifier 158 may be a readable tag configured to be removably coupled to the user. In the exemplary embodiment of FIG. 16, the readable tag may be a radiofrequency identification (RFID) tag coupled to the caregiver with a lanyard, and/or an RFID tag coupled to the patient with a wristband. Other embodiments are contemplated, such as a near field communication (NFC) sensor coupled to the patient support apparatus 30 and configured to detect the identifier 158 disposed on a mobile device 156. The mobile device 156 is in wireless communication with the module 152 through NFC or other wireless means commonly known in the art. The mobile device 156 may integrate the user interface 110 and the display 112 consistent with earlier described embodiments of the patient support system 28.

The controller 102 is configured to receive the identification input signal from the identification system 150. Based on the identification input signal, the controller 102 is configured to determine an identification-based user menu 154 and generate an updated display output signal representative of the identification-based user menu 154. The controller 102 is further configured to transmit the updated display output signal to the display 112 to display the identification-based user menu 154 (see FIG. 17).

With reference again to FIG. 16, the touchscreen 113 comprising the user interface 110 and the display 112 is coupled to one of the side rails 46 of the patient support apparatus 30, and the mobile device 156 comprising the user interface 110 and the display 112 is supported by a caregiver C. The module 152 of the identification system 150 is coupled to the side rail 46, but other locations are contemplated. The identifier 158 of the identification system 150 is coupled to the patient P. In one embodiment, the identifier 158 comprises a readable tag incorporated in a wristband often worn by patients in medical facilities. The identifier 158 contains information associated with the patient P, such as a name, social security number, patient identification number, date of birth, and the like. In response to a user input to the user interface 110, the module 152 detects the identifier 158. In one example, the user input comprises scanning a barcode or quick response (QR) code printed on the readable tag. In another example, the user input comprises a user input to the user interface 110 for the module 152 to search for identifiers 158 within range or within a predetermined proximity to the patient support apparatus 30. In still another exemplary embodiment, the module 152 is configured to automatically detect and read the identifier 158 in the predetermined proximity. The identification system 150 generates and transmits the identification input signal. The identification input signal may be the information associated with the patient P from the identifier 158, or the identification system 150 may further process the information to generate the identification input signal. For example, the identification system 150 may correlate the identifying information of the patient P to the condition for which he or she is being treated (e.g., migraine). In such an example, the generated identification input signal is representative of the condition.

Figure 16:
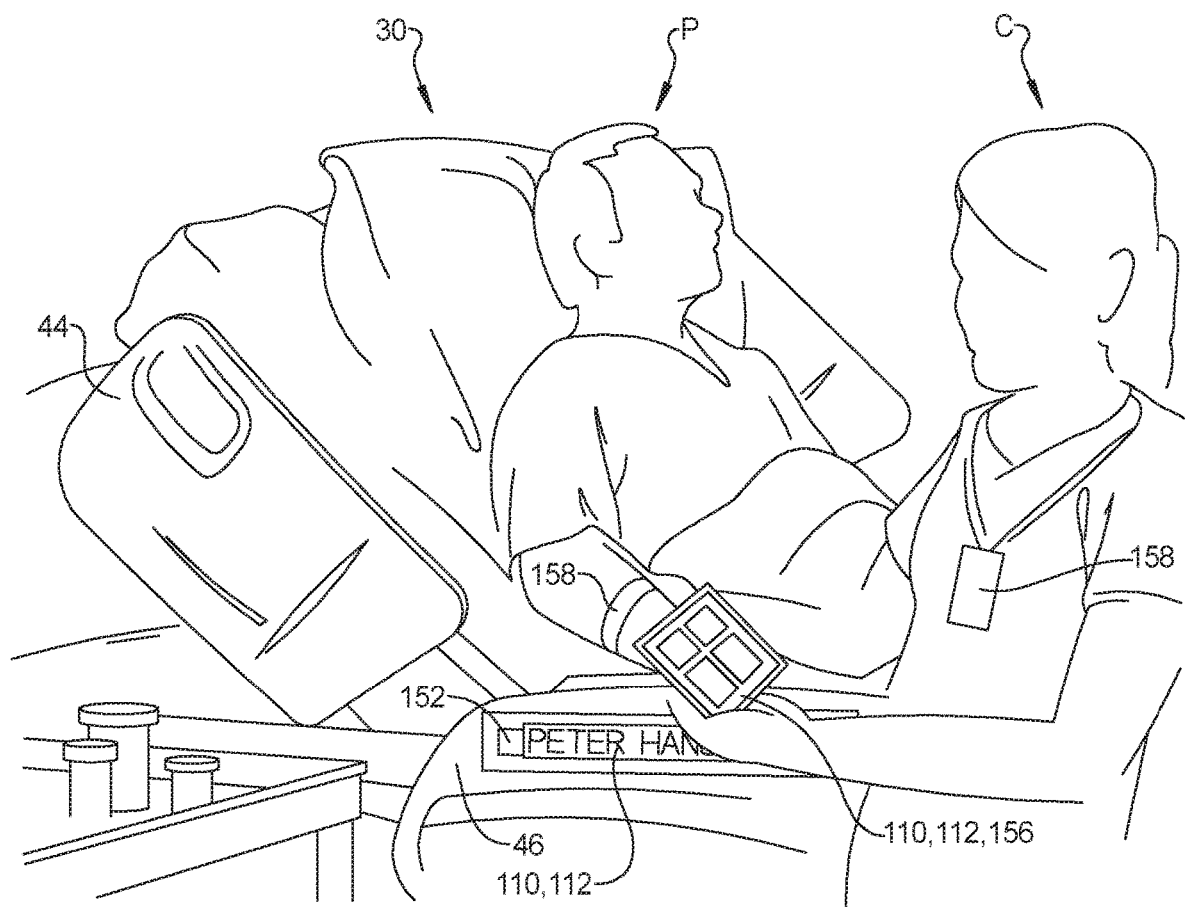
FIG. 16 is a representative illustration of a patient supported by the patient support apparatus of FIG. 1 with the caregiver attending to the patient. An identifier, such as a readable tag, is coupled to each of the patient and the caregiver. The caregiver is carrying a mobile device.

The controller 102 receives the identification input signal from the identification system 150. The controller 102 may transmit a signal to the display 112 to display the name and/or other identifying information associated with the patient P. FIG. 16 shows the display 112 coupled to the patient support apparatus 30 displaying the name of the patient P. Additionally or alternatively, the display 112 may display the condition of the patient P.

Figure 17:
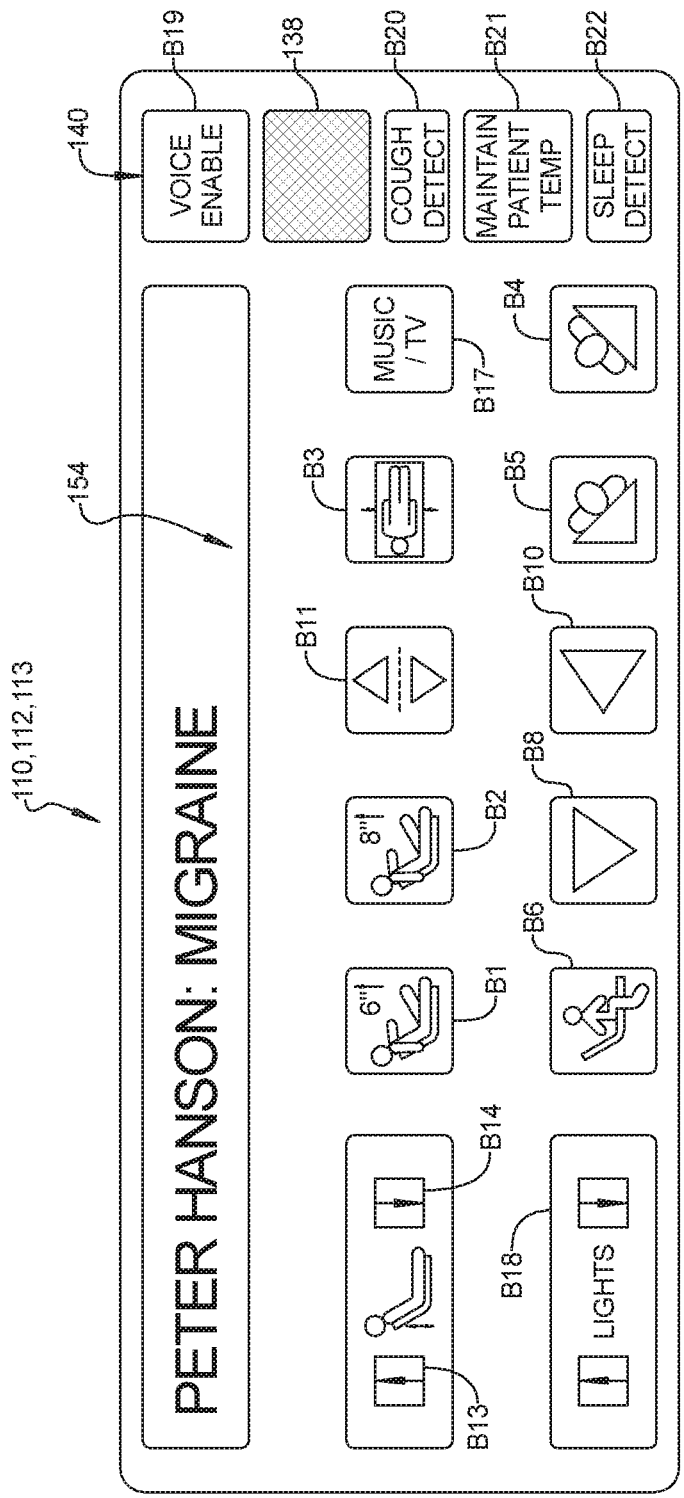
FIG. 17 is an identification-based user menu.

The identification-based user menu 154 is determined based, at least in part, on the identification input signal received from the identification system 150. In an exemplary embodiment, the identification-based user menu 154 comprises indicia 116 representative of the operational devices 70-90 most relevant or advantageous to the care of the patient P. Referring to FIG. 17, the identification-based user menu 154 for the patient P is shown. The identification-based user menu 154 of FIG. 17 comprises displaying information such as the patient's name, Peter Hanson, and his primary diagnosis, migraine. Additional identifying information may be displayed without limitation. The patient P is suffering from a migraine such that it may be beneficial for the identification-based user menu 154 to include indicia 116 at least representative of the deck adjustment device 84 (buttons B13 and B14) to decrease blood flow to the head, and/or the lighting device 90 (button B18), as individuals suffering from migraines often desire lower light conditions. Other advantageous features of the customized and/or responsive user menus described throughout the present disclosure may be incorporated into the identification-based user menu 154. For example, the identification-based user menu 154 may comprise an updated arrangement and/or updated scaling different from an initial arrangement and an initial scaling, respectively. FIG. 17 shows the deck adjustment device 84 and the lighting device 90, which in the present example are considered to be the two devices most relevant to the care of migraine, arranged at the left of the identification-based user menu 154. The updated arrangement may be different from an initial arrangement, such as a default arrangement, or an arrangement of indicia 116 for treating another condition such as DVT. The indicia 116 representative of the deck adjustment device 84 and the lighting device 90 are scaled differently than other, perhaps less relevant indicia 116 of the identification-based user menu 154. The updated scaling may be different from an initial scaling, such as a default scaling, or a scaling of indicia 116 for treating another condition such as DVT. The identification-based user menu 154 may be displayed on the touchscreen 113 coupled to the patient support apparatus 30, the mobile device 156 carried by the caregiver C, and/or any other suitable display.

To facilitate the determination of the identification-based user menu 154, the patient support system 28 may comprise a referential database 160 in communication with at least the controller 102 and the identification system 150. The referential database 160 may be stored on the non-transitory memory 130 of the patient support system 28 or a remote location (e.g., a server of a hospital local area network). The referential database 160 associates the identifier 158 of the user (e.g., the patient P or the caregiver C) with one or more of the operational devices 70-90 to be represented as indicia 116 of the identification-based user menu 154. In another exemplary embodiment, the referential database 160 associates the identification of the patient P with one or more conditions, and further associates the condition(s) with one or more of the operational devices 70-90 to be represented as indicia 116 of identification-based user menu 154. Exemplary referential databases are shown in FIGS. 18 and 19.

The referential database 160 may be predefined through software or other suitable means, or determined by the frequency of the user selections over time. The software may be provided to allow indicia 116 to be selected and included in the identification-based user menu 154 for a particular patient and/or a particular one or more of the patient's conditions. Additionally or alternatively, the non-transitory memory 130 may store over time, the frequency of the user selections of the operational devices 70-90 for each user, including the patient P. The frequency of the user selections may be associated with the identifier 158 of the patient P with the information stored in the non-transitory memory 130. The controller 130 may generate the referential database 160 based on the stored information. The indicia 116 representative of the most frequent selections comprises at least a portion of the identification-based user menu 154 for the patient P, which may be in addition to the frequency of the user selections comprising the usage characteristics of the customized user menu 120b, 122b, 124b previously described. Further, frequency of the user selections may be associated with the one or more of the patient's conditions as well as other patients being treated for the same condition(s) with the information stored in the non-transitory memory 130. The controller 102 may aggregate the collected information stored in the non-transitory memory 130 to generate the referential database 160 comprising the most frequent selections for a particular condition, such as migraines. The indicia 116 representative of the most frequent selections for the particular condition may comprise at least a portion of the identification-based user menu 154 for the patient P and possibly other patients being treated for migraines.

In the exemplary embodiment illustrated in FIG. 18, the referential database 160 comprises a list of conditions. Based on predefined parameters associated with typical treatment protocols, the conditions may be associated with one or more operational devices 70-90 of the patient support apparatus 30. When the patient P is, for example, admitted to the hospital, the identifying information is entered into the referential database 160 and correlated with the condition(s). The correlated referential database 160 is stored in the non-transitory memory 130. The stored correlated referential database may define a user profile 162 associated with each of the users. The user profiles 162 of FIGS. 18 and 19 each comprise the identifier 158, the user group 166, the conditions, and user permissions 164. Upon the module 152 detecting and/or receiving the identifier 158 associated with the patient P, the controller 102 is configured to access the referential database 160 after receiving the identification input signal from the identification system 150. The controller 102 is further configured to determine the updated display output signal based on the information received from the referential database 160. As previously described, the updated display output signal is representative of the identification-based user menu 154. The updated display output signal is transmitted to the display 113 to display the identification-based user menu 154.

Often during the facilitation of medical care, several types of medical professionals interact with the patient. The medical professionals may include physicians, nurses, physical therapists, occupational therapists, physicians' assistants, orderlies, and the like. The role of each medical professional involved in the care for the patient may be different, and each medical professional may require using different features of the patient support system 28. For improved patient care, the patient support system 28 of the present disclosure may provide customized user menus based on the identification of the user, such as the medical professional, for controlling the operational functions 70-90 of the patients support apparatus 30. This may be the case regardless of the identity of the patient being treated. In other words, relative to known systems that may display patient-specific information to the caregiver based on the role of the caregiver, advantageous features of the present disclosure provide identification-based user menus for controlling preferred or pertinent operational functions 70-90 of the patients support apparatus 30 based on the caregiver's role. Further, the customized user menus may further limit access of certain features of the patient support system 28 for patient privacy, safety, and the like. In certain embodiments, features of the patient support system 28 accessible to the user may be limited by conditions such as patient risk factors. For example, should the patient be assessed as having a higher risk of falling episodes, the customized user menus based on the identification of the user may prevent access to (or avoid displaying) certain features related to lowering the side rails 50 of the patient support apparatus 30. The referential database 160 comprises the identifier 158 associated with the user. In an exemplary embodiment, the user comprises a plurality of users with the identifier 158 associated with each of the plurality of users. For example, the plurality of users may be the patient(s), physician(s), the nurse(s), etc. The referential database 160 further comprises the user permissions 164 correlating the operational devices 70-90 controllable by each of the users and/or the indicia 116 (and/or other information) viewable by each of the users. Exemplary user permissions 164 may comprise electronically prescribing medication, viewing patients' electronic medical records (EMR), editing patients' EMRs, and controlling the operational devices 70-90 of the patient support apparatus (PSA) 30.

With continued reference to the referential database 160 of FIGS. 18 and 19, the identifier 158 comprises an alphanumeric code associated with each of the users. The alphanumeric code is one non-limiting example of data associated with the readable tag or other device detectable by the module 152 of the identification system 150. In one embodiment, the alphanumeric code is the identifier 158 received by the identification system 150 and transmitted as the identification input signal to the controller 102. The controller 102 associates with user permissions 164 with the identifier 158. In the illustrative embodiment, the user permissions 164 comprise "levels of access," with the users having more responsibility (e.g., credentials) being given a higher level of access. Physicians having the user permission 164 of "Level 5" may be able to, for example, electronically prescribe medications from the user interface 110, whereas the physical therapist having the user permission 164 of "Level 2" access may be unable to electronically prescribe medications, but rather use the user interface 110 to control the operational devices 70-90 of the patient support apparatus 30 described throughout the present disclosure. The specific configurations of each "level of access" may be predefined through software or other suitable means, or determined by user selections over time consistent with various embodiments described throughout the present disclosure. The referential database 160 of FIG. 19 similarly comprises the user permissions 164 correlating the devices controllable by each of the users based on the identifiers 158. Whereas the user permissions 164 of the physicians and the nurse practitioners may control all of the above, the access of other users of lesser responsibility or credentials may be limited. It is also contemplated that those within the same user group 166 or level of user permissions 164 may be assigned control of different subsets of the operational devices 70-90 of the patient support apparatus 30. For example, a cardiologist and an orthopedist are both assigned to the same user group 166, but each may have different user permissions 164 based on their role in facilitating patient care.

The controller 102 may be configured to access the referential database 160 after receiving the identification input signal from the identification system 150, and determine the identification-based user menu 154 based on the user permissions 164. More specifically, the controller 102 determines which function(s) of each of the operational devices 70-90 are controllable by the user profile 162 associated with the user based on the user permissions 164 associated with the identifier 158 of the referential database 160. Based on those controllable operational devices 70-90, the controller generates an updated display output signal representative of the identification-based user menu 154. In certain embodiments, the identification-based user menu 154 comprises indicia representative of the operational devices 70-90 of the patient support apparatus 30 controllable by the user. Additionally or alternatively, the identification-based user menu 154 comprises options, items, instructions, or other output or information (see, e.g., FIGS. 11A and 11B).

Referring to FIGS. 16 and 19, the caregiver C is, for example, physician Jill Smith. The identifier 158 associated with the user profile 162 is the alphanumeric code 'JS9821.' The identifier 158 is stored or otherwise embodied in the readable tag around her neck, and/or the mobile device 156 being carried by Dr. Smith in FIG. 16. Once the tag and/or mobile device 156 is within the predetermined proximity to the patient support apparatus 30, such as two feet, three feet, or five or more feet, the module 152 detects the tag and/or mobile device 156, and the identification system 150 in communication with the module 152 receives the alphanumeric code. The identification system 15 generates the identification input signal based on the alphanumeric code or transmits the alphanumeric code as the identification input signal to the controller 102. The controller 102 accesses the referential databases 160. Using techniques known in the software arts, the controller 102 determines the user, the user group 162, and the user permissions 164 based, at least in part, on the identifier 158. The controller 102 may transmit an updated display signal to the display 112 to display the name of the user (e.g., Jill Smith), the user group (e.g., Physician), and/or the user permissions 164 (e.g., Level 5). Based on the user permissions 164, the controller 102 determines the identification-based user menu 154. The identification-based user menu 154 comprises indicia 116 representative of the operational devices 70-90 of the patient support apparatus 30 controllable by Dr. Smith, and/or options, items, instructions, and/or other output or information desirable or suitable for viewing by Dr. Smith. The controller 102 generates the updated display output signal representative of the identification-based user menu 154, and transmits the updated display output signal to the display 112. FIG. 16 shows one display 112 coupled to the side rail 46 of the patient support apparatus 30 and another associated with the mobile device 156. Thus, by simply approaching the patient support apparatus 30, Dr. Smith may automatically receive on the display 112 the customized and/or adaptive user menu uniquely tailored to her role in treating the patient P. The present disclosure further contemplates the identification-based user menu 154 may be utilized in addition to the location-based user menu 144, the customized user menu 120b, 122b, 124b, the position-based user menu 134, and/or the position-based output 142 previously described herein.

In embodiments where more than one type of customized user menu is utilized (e.g., the position-based user menu 134, the location-based user menu 144, etc.), one or more algorithms may be implemented to facilitate optimal presentation of the customized user menus on the display 112. For example, should the user select all of the parameters of the options menu 128 (see FIG. 8) such that the customized user menu 120b, 122b, 124b is based on one or more of the usage characteristics, the position-based user menu 134, location-based user menu 144, and the identification-based user menu 154, the algorithms may be executed to selectively prioritize how the customized user menus are presented on the display 112. The algorithms may follow protocols to prioritize certain types of the customized user menus to more prominently display the prioritized customized user menus on the display 112. The protocols, for example, may be dependent on the individual using the patient support system 28. For example, if a physician is using the user interface 110, the algorithm may be executed to more prominently display the identification-based user menu 154 on the display 112 relative to the location-based user menu 144. The identification-based user menu 154 based on the identification of the physician may be more beneficial to the physician using the user interface 110 than the location of the patient support apparatus 30 within the medical facility. The present disclosure contemplates numerous manners in which the algorithms may be executed to facilitate optimal presentation of the customized user menus on the display 112.

After facilitation of patient care or otherwise, the caregiver C may move away from the patient support apparatus 30. In certain embodiments, the user interface 110 may be locked or disabled when the identifier 158 is not within the predetermined proximity. Additionally or alternatively, the display 112 may display a default screen when the identifier 158 is not within the predetermined proximity. The default screen may be a "screen saver" being displayed on the display 112, a default user menu, or any other information other than the identification-based user menu 154.

The patient support system 28 may further comprise a sensing system 170 in communication with the controller 102 and the control system 100, as shown in FIG. 2. The sensing system 170 may be used by the controller 102 for various purposes. The sensing system 170 comprises one or more sensors S. The sensors S may comprise one or more force sensors (e.g., load cells), timers, temperature sensors, switches, heart monitors, acoustic sensors (e.g., a cough monitor), microphones, breathing monitors, optical sensors, electromagnetic sensors, motion sensors, accelerometers, potentiometers, infrared sensors, ultrasonic sensors, mechanical limit switches, membrane switches, and cameras. Other types of sensors are also contemplated. The sensors S can be located anywhere on the patient support apparatus 30 or remote from the patient support apparatus 30. For example, the sensors S may be located on or in the base 34, the intermediate frame 36, the patient support deck 38, the mattress 40, the side rails 44, 46, 48, 50, the headboard 52, the footboard 54, or other suitable locations.

In one embodiment, the sensing system 170 may be used to detect or determine a current patient condition. Various current patient conditions may be determined and used to control the operational devices 70-90 of the patient support apparatus 30. Such patient conditions can comprise current positions of the patient (e.g., the patient is slouched, the patient is off center, the patient is lying supine, the patient is getting ready to exit, the patient is sitting up, etc.). Patient conditions can also comprise physiological conditions (e.g., a patient's heart rate, respiration, temperature, blood pressure, the patient is sleeping, the patient is coughing, skin conditions of the patient, etc.). Patient conditions can also comprise standard patient characteristics (e.g., weight, width, height, pathology, race, etc.). Patient conditions can also comprise patient history (e.g., activity level, movement history, etc.). Patient conditions can be determined by the controller 102 using the sensing system 170 and/or by input from the caregiver, patient, or other person, and/or retrieved from an electronic medical record (EMR). Data from the sensing system 170 can be stored in the non-transitory memory 130 of the controller 102 and can be used to provide a history log or charts for the caregiver, as well as activate alarms or other indicators to the caregiver if needed.

In various embodiments, the controller 102 is configured to determine the customized user menu based, at least in part, on the patient conditions. The sensing system 170 determines one of the patient conditions and transmits a patient condition input signal. The controller 102 is configured to receive the patient condition input signal from the sensing system 170. The controller 102 determines the customized user menu based on the patient condition input signal and generates an updated display output signal representative of the customized user menu. The controller transmits the updated display output signal to the display 112 to display the customized user menu. For example, the sensors S comprising load cells detect uneven weight distribution on the patient support surface 42, 43 of the patient support apparatus 30. The sensing system 170 determines the patient condition comprising the patient being at risk of egress from one of the sides 49 of the patient support apparatus 30. The sensing system 170 provides the controller 102 with the patient condition input signal representative of the patient condition. The controller 102, in response to receiving the patient condition input signal, determines that the customized user menu should comprise the patient centering device 72 and/or the bed width extension device 82. The controller 102 generates an updated display output signal representative of the customized user menu such that the customized user menu comprises indicia 116 representative of the patient centering device 72 (button B3 of FIG. 3) and/or the bed width extension device 82 (buttons B11 and B12 of FIG. 4). The display 112 displays the customized user menu.

In various embodiments, the sensing system 170 provides a second input signal to the controller 102 to initiate, continue or terminate the operational devices 70-90 of the patient support apparatus 30. In some cases, the second input signal is the patient condition input signal. The controller 102 may respond to the second input signal to automatically continue operation of one of the operational devices 70-90 until the patient reaches a desired patient condition, as indicated by the second input signal. In these embodiments, the caregiver is enabled to perform other tasks while the sensing system 170 facilitates ongoing control of the operational devices 70-90. In certain embodiments, the sensing system 170 may indicate when the predetermined function has been completed by the operational devices 70-90 of the patient support apparatus 30. Further, the controller 102 may be configured to continue operating the operational devices 70-90 until the predetermined function is complete. In the above example, the sensing system 170 may detect when the patient has returned near the centerline and the controller 102 may cease operation of the patient centering device 72 when this is sensed.

In embodiments wherein the user interface 110 and the display 112 are embodied on the mobile device 156, the mobile device 156 may be associated with the user as opposed to the patient support apparatus 30 of the patient support system 28. In other words, the mobile device 156 belongs to the user(s) and provides portability to the patient support system 28. The mobile device (e.g., iWatch®, iPhone®, iPad®, or similar electronic devices) includes identification data of the user, such as the identifier 158 associated with the user that is correlated with the user profile 162. The mobile device 156 belonging to the user may be in addition to the user interface 110 being associated with the patient support apparatus 30. In certain embodiments, many of the caregivers have a mobile device with all of the mobile devices 156 adapted to facilitate the functions of the patient support system 28 described throughout the present disclosure.

The patient support system 28 may further provide the user with the option to selectively customize the user menus. The user menu 114 being displayed on the display 112 may be stored in the non-transitory memory 130 by default or in response to an input to the user interface 110 to do so. The user menu 114 comprises indicia 116 representative of the operational devices 70-90 of the patient support apparatus 30, and/or any other options, items, instructions, or other output or information consistent with the present disclosure. The user may define the customized user menu by selectively adding, removing, and/or replacing one or more of the indicia 116 of the user menu 114. The user may further customize the arrangement and/or the scaling of the indicia 116 displayed on the display in a manner consistent with the various embodiments of the present disclosure. In one exemplary embodiment illustrated in FIGS. 20 and 21, a control suite 180 may be incorporated into the patient support apparatus 30 (e.g., coupled to the side rail 46) and comprises the user interface 110 and the display 112. In some embodiments, at least a portion of the display 112 displays the control suite 180, such as on the touchscreen 113, mobile device 156, and the like. In other embodiments, the control suite 180 may be operated as a pendant or mobile device to control the operational devices 70-90 of the patient support apparatus 30. The control suite 180 includes a plurality of customizable controls 182a-e that allow the user to move the patient support apparatus 30 to a memorized custom configuration.

One or more of the customizable controls 182a-e, when actuated, automatically moves the patient support apparatus 30 to a defined configuration that was customized by the user. In one embodiment, the customizable controls 182a-e are initially not associated with a defined configuration, and the customizable controls 182a-e do not move the patient support apparatus 30 until they are associated by the user with one of an infinite number of defined configurations. The precise manner in which the customizable controls 182a-e are associated with the desired configuration of patient support apparatus 30 can vary widely. In one embodiment, when the patient support apparatus 30 is moved to the desired configuration and the user actuates and holds a selected one of the customizable controls 182a-f for a minimum time period, that particular customizable control 182a-f becomes associated with that particular desired configuration. In other words, actuating and holding one of the customizable controls 182a-f memorizes (e.g., the controller 102 stores in memory) the current configuration and automatically associates the current configuration with the customizable control 182a-f. If the patient support apparatus 30 subsequently assumes a different configuration, the user may actuate the particular control 182a-f that was previously customized such that the patient support apparatus 30 automatically returns to the desired configuration.

Regardless of the specific manner in which one of the customizable controls 182a-f is associated with the desired configuration, one or more parameters associated with the desired configuration may be stored in the non-transitory memory 130 and retrieved when one of the customizable controls 182a-f is subsequently actuated. With respect to patient support apparatus 30, the non-transitory memory 130 may store, for example, a backrest angle, a leg rest angle, a seat tilt angle, and a seat height, and the like, for the customizable controls 182a-e. The controller 102 retrieves these parameters when the corresponding one of the customizable controls 182a-f is actuated and operates one or more of the operational devices 70-90 of the patient support apparatus 30 so as to drive the backrest, seat, leg rest, and/or other component to the stored angles, positions, and/or other stored configuration.

In some embodiments, the customizable controls 182a-f are customizable in a manner that allows the user to move one or more of the movable components (e.g., the fowler section, the seat section, the thigh section, the foot section) to atypical orientations or positions that lie outside of the movement paths of patient support apparatuses commonly employed. The user may create custom orientations for the patient support apparatus 30 otherwise not achievable by most predefined or default configurations. Stated differently, the customizable controls 182a-f enable the user, in at least one embodiment, to adjust the components of the patient support apparatus 30 to the desired configuration, thereby enabling custom combinations of the backrest angle, seat angle, leg rest angle, seat height, and the like, to be defined by the user. In one embodiment, each component may move individually (i.e., without the other components moving), and the user actuates and holds a particular one of the customizable controls 182a-f for the predetermined period. The angles and positions of the movable components are stored and associated with that particular customizable control.

In addition to associating a particular configuration of patient support apparatus 30 with a particular one of the customizable controls 182a-f, the control suite 180 is also adapted to allow a user to provide a custom name for each of the customizable controls 182a-f. This helps the user to remember and track which of the customizable controls 182a-f is associated with each of the desired configurations of the patient support apparatus 30. FIG. 20 shows default labels (e.g., "MEM_1") for each of the customizable controls 182a-f. None of the controls 182a-f have been named by the user. FIG. 21 shows three of the controls 182a, 182b have been named with the labels "Incline 20°," "Incline 40°," and "Decline," respectively. The "Incline 20°" label, for example, may be associated with the desired configuration of the patient support apparatus 30 comprising the patient support surface 42, 43 being angled relative to the floor surface at 20°. The remaining three controls 182b-f have not been named in FIG. 21.

The manner in which the user provides the labels for the customizable controls 182a-f varies in different embodiments. In one embodiment, the user interface 110 and the display 112 comprise the touchscreen 113 (coupled to the patient support apparatus 30 or remote as a mobile device 156) that displays a keyboard when the user actuates and holds a selected one of the customizable controls 182a-f. The user then uses the keyboard to type the desired name to be associated with the selected customizable controls 182a-f. In another embodiment, an image of a virtual keyboard is projected on a surface of the patient support apparatus 30 and the user uses the keyboard image to type a desired name for the selected customizable control. One example of a system for displaying images of a virtual keyboard that may be used for this purpose is disclosed in commonly assigned U.S. patent application Ser. No. 14/549,006 filed Nov. 20, 2014, by inventors Richard A. Derenne et al. and entitled PERSON SUPPORT APPARATUSES WITH VIRTUAL CONTROL PANELS, the entire disclosure of which is hereby incorporated herein by reference. In still another embodiment, the user is able to provide the label for the customizable controls 182a-e by using other buttons, keys, or controls that temporarily switch functionality and become alphanumeric inputs. For example, in one embodiment, when a user is assigning a custom name to one of controls 182a-f, other indicia 116 of the user menu 114 temporarily switch to inputs comprising the letters A-C, D-F, G-I, J-L, M-O, P-R, S-U, V-X, and Y-Z, respectively. The user may access the different letters by actuating the control repeatedly to toggle through the different letters. Thus, for example, if the user wanted to assign a name that began with the letter 'K' to one of the customizable controls 182a-f, the user actuates the input associated with J-L twice.

In still another embodiment, the names associated with custom controls 182a-f are assigned remotely via a computer having a keyboard associated therewith. The computer, which may be part of a healthcare facility computer network, forwards the assigned name to the control suite 180 associated with each patient support apparatus 30 within the healthcare facility via a wired or wireless network connection. In certain embodiments, the desired orientations of the patient support apparatus 30 associated with each of the custom customizable controls 182a-f may also be assigned remotely. Stated differently, instead of assigning the desired orientation of the patient support apparatus 30 to one of the customizable controls 182a-f by actuating and holding the control after the patient support apparatus 30 has been moved to the desired configuration, the patient support apparatus 30 is configured to communicate with the remote computer that assigns the configuration to one or more of the customizable controls 182*a-f*. The user at the remote computer, in one embodiment, selects the desired angles for each of the movable components, inputs the information into the remote computer, assigns the desired configuration to a selected one of the customizable controls 182*a-f*, and then forwards the data to the patient support apparatus 30.

It will be understood that, although FIGS. 20 and 21 depict six customizable controls 182*a-f*, the number of customizable controls may be varied from this number. Further, although customizable controls 182*a-f* have been primarily described herein with respect to configurations and operational devices 70-90 of patient support apparatus 30, it will be understood that customizable controls of the type disclosed herein can be used with other types of patient support apparatuses that have different parameters for their configurations. For example, when such customizable controls are used on a chair, each customized control defines one or more of the angles for each of the backrest, seat tilt, and leg rest, as well as a height for a seat.

In certain embodiments, the user interface 110 and the display 112 may also provide information related to the vital signs of the patient. The display 112 may provide the body temperature, pulse rate, respiration rate, blood pressure, and/or other parameters of the patient. The vital sign information may be provided on the "home screen" and/or any one of the default user menus, customized user menus, and/or submenus. In certain embodiments, a portion of the display 112 (e.g., upper-right corner) is dedicated to the vital signs information such that the vital signs information is continuously displayed. In other embodiments, the user may select indicia 116 to view the vital signs information. In certain embodiments, the vital signs information may be displayed with certain one or more of the customized user menu 120*b*, 122*b*, 124*b* based on one or more of the usage characteristics, the position-based user menu 134, location-based user menu 144, and the identification-based user menu 154. For example, caregivers treating the patient may be interested in receiving the vital signs information upon approaching the patient supported on the patient support apparatus 30. The locating system 132 generates and transmits to the controller 102 the position input signal based on the position of the approaching user interface 110. The controller 102 is configured to determine a position-based user menu 134 based on the position input signal with the positioned-based user menu 134 comprising the vital signs information. The controller 102 generates an updated display output signal representative of the position-based user menu 134 and transmits the updated display output signal to the display 112 to display the position-based user menu 134. The vital signs information is displayed on the display 112.

Figure 22A:
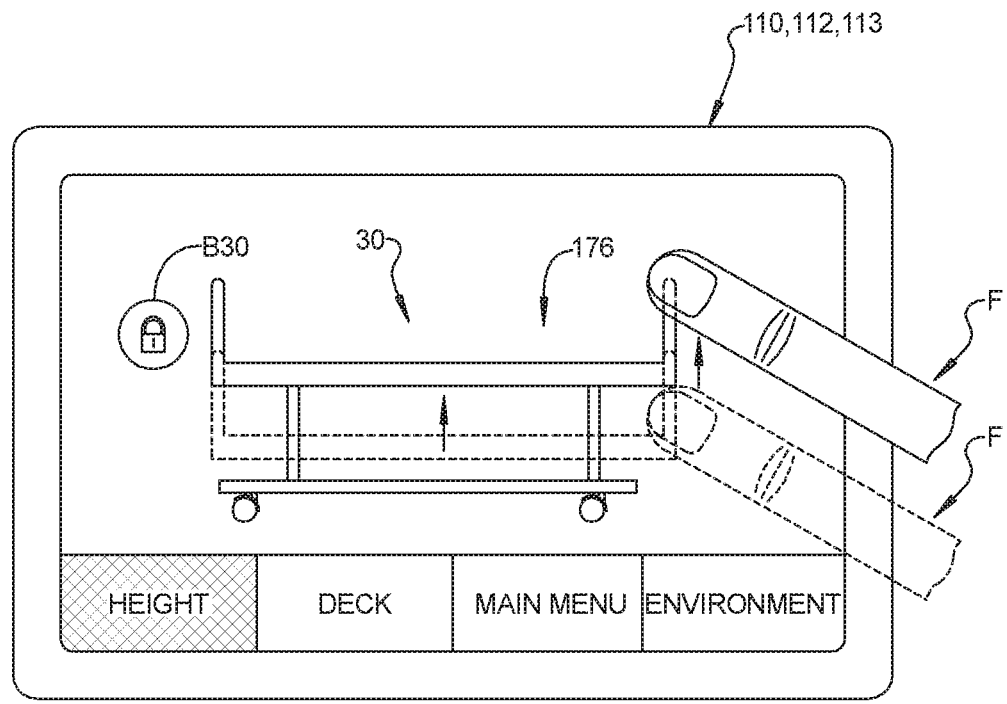
FIG. 22A is a pictorial representation of the patient support apparatus of FIG. 1, shown schematically, for controlling the operations of the patient support apparatus.
Figure 22B:
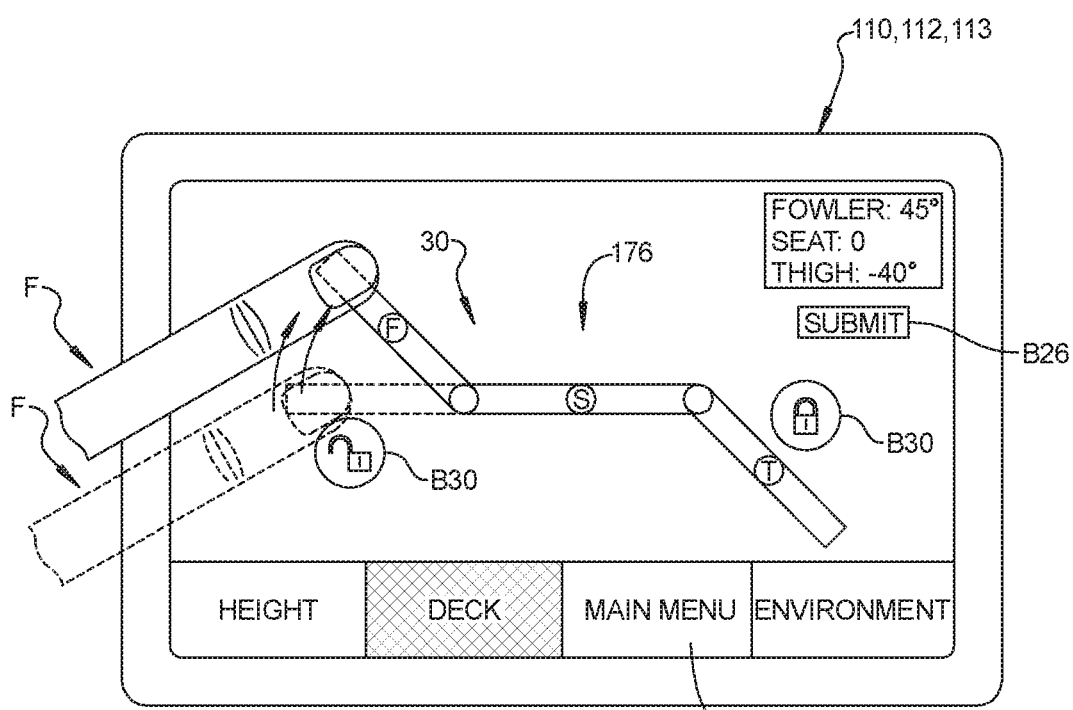
FIG. 22B is another pictorial representation of the patient support apparatus of FIG. 1, shown schematically, for controlling the operations of the patient support apparatus.

In various embodiments described throughout the present disclosure, the indicia 116 are icons representative of the operational devices 70-90 of the patient support apparatus 30. Other non-limiting examples of the indicia 116 may comprise lists and/or grids and/or arrays of text and/or graphics displayed on the display 112. The user interface 110 and the display 112 may be integrated on a touchscreen coupled to the patient support apparatus 30 (see FIG. 1) and/or embodied as the mobile device 156 (see FIGS. 1 and 16). In certain embodiments, the touchscreen 113 displays a pictorial representation 176 of the patient support apparatus 30. FIGS. 22A and 22B show exemplary pictorial representations of the patient support apparatus 30. The pictorial representation 176 may be a static or dynamic two-dimensional graphical object, as shown, or three-dimensional graphical object. The pictorial representation 176 may be realistic (e.g., a computer aided design (CAD) model) or simplified or stylized to any extent. FIGS. 22A and 22B shows the pictorial representation 176 occupying only a portion of the touchscreen 113 and bounded by a taskbar below. It is contemplated that the pictorial representation 176 may occupy an entirety of the touchscreen 113 without the taskbars, other indicia, menu buttons, and the like. In such a variant, the indicia, menus, and the like may "pop up" while directly engaging the pictorial representation 176 of the patient support apparatus 30. Further, the pictorial representation 176 may be rotated and/or repositioned (e.g., panned) through inputs to the touchscreen 113. Similarly, the user may zoom in or zoom out on the pictorial representation 176 through input to the touchscreen 113, such as, for example, by a pinching motion with two of the user's fingers touching the touchscreen 113.

The input from the user to the touchscreen 113 may comprise directly engaging the pictorial representation 176 to control one or more operations of the operational devices 70-90 of the patient support apparatus 30. Engaging the pictorial representation 176 may include touching the touchscreen 113 with a finger, hand, stylus, or any other suitable object or device. In particular, the user may touch a desired component or feature of the pictorial representation 176 of the patient support apparatus 30 displayed on the touchscreen 113 to produce a corresponding result of the patient support apparatus 30. For example, FIG. 22A shows an elevational view of a schematic representation of the patient support apparatus 30 in an initial position (shown in phantom) and a desired or final position (shown in solid). The initial and final positions of the pictorial representation 176 are representative of the initial and final positions, respectively, of the patient support surface 42, 43 relative to the base 32 of the patient support apparatus 30. In the initial position, the user touches the touchscreen 113 with a finger F (shown in phantom), and slides the finger F upwardly as shown. In particular, the user touches the relevant portion of the pictorial representation 176 (e.g., the fowler section F, the seat section S or litter, and/or the thigh section T) on the touchscreen 113. The final position of the pictorial representation 176 (shown in solid) may be interpreted by the controller 102 as the desired position of the patient support surface 45, 46 or other suitable component of the patient support apparatus 30. The touchscreen 113 provides an input signal to the controller 102 as previously described. The controller 102 provides a corresponding signal to control the operational devices 70-90 of the patient support apparatus 30, in this example the lift device 78. Consequently, the patient support surface 45, 46 or other suitable component moves in a manner corresponding to the user input to the touchscreen 113. Unlike some conventional user interfaces that use buttons such as "up" and "down" or "+" and "−", embodiments of the present disclosure correlates the movement of the user's finger F relative to the pictorial representation 176 of the patient support apparatus 30, to command movement providing for a more intuitive operation of the patient support apparatus 30.

It is contemplated that tutorials or instructions may be provided with the pictorial representation 176. Exemplary modalities of instruction include pop-up instruction, voice instruction, video instruction, and/or minimal text instruction. In certain embodiments, the user may manipulate the pictorial representation 176 on the touchscreen 113 before or after engaging the desired portion of the pictorial representation 176. Certain operational devices 70-90 of the patient support apparatus 30 that are controllable via the touchscreen 113 may not be visible upon display of the pictorial representation 176. For example, the indicia 116 that are icons representative of the operational devices 70-90 of the patient support apparatus 30 may be too small to be effectively selected via the touchscreen 113, or the indicia 116 may be positioned on a side opposite what is displayed initially. The user may rotate, pan, and/or zoom in on or out of the pictorial representation 176 to more effectively visualize the indicia 116 representative of the operational devices 70-90 to be controlled. Further, as the user provides the input to zoom in and zoom out, the pictorial representation 176 may be refreshed or be re-rendered to provide more or less detail. For example, the pictorial representation 176 shown in FIG. 22A shows relatively little detail of the patient support apparatus 30. Should the user provide an input to the touchscreen 113 to zoom in on the headboard, the pictorial representation 176 of the headboard may be rendered to show structures, devices, and/or features not previously shown. In certain variants, the pictorial representation 176, as it is refreshed or re-rendered to provide more detail, may include virtual features corresponding to features of the patient-support apparatus. In other words, with more and more detail shown, the pictorial representation 176 appears as a one-to-one model of the patient support apparatus 30, including not only the larger structures but also the smaller controls (e.g., tactile buttons) on the patient support apparatus 30. The caregiver may zoom in on the pictueral representation 176 of a known location of a button on the patient support apparatus 30. Such a variant may be particularly useful with a caregiver knowledgeable of the operation of the patient support apparatus 30 using the mobile device 156 remove from the same. Knowing the location of the desired input on the patient support apparatus 30 facilitates quick navigation on the pictorial representation 176. Conversely, should the user provide an input to the touchscreen 113 to zoom out, the features previously shown may be removed or genericized as the pictorial representation 176 shows a greater portion of the patient support apparatus 30. In other embodiments, CAD software may be provided to permit the user to manipulate the pictorial representation 176 in the manner desired. FIGS. 22A and 22B each show a single elevation view of the patient support apparatus 30. Multiple views (e.g., plan view, perspective view, etc.) of the patient support apparatus 30 may be displayed on the touchscreen 113, and in particular in a single window.

The user may engage the indicia 116 through, for example, engaging the touchscreen 113 or double clicking with the CAD software to select the corresponding portion of the patient support apparatus 30. The selected portion may be visually emphasized in manners previously described. Should the user provide an input that may, as determined by the controller 102, be applicable to more than one feature of the patient support apparatus 30 shown in the pictorial representation 176, a prompt may be provided to confirm which component should be engaged. Such a confirmation may be particularly useful when several components are illustrated within a small area. In other embodiments, the confirmatory prompt may be provided in every instance, including those when the input from the user is clearly directed to a particular component, and/or instances where uncertainty is low as which feature or component is being selected.

The user may engage the pictorial representation 176 in a manner that provides simulated movements of the pictorial representation 176 on the display 112. The simulated movements of the pictorial representation 176 may or may not provide corresponding movements of the patient support apparatus 30. In one non-limiting example, a lever (not shown) associated with the patient support apparatus 30 may be represented in the pictorial representation 176. Actuation of the lever (on the patient support apparatus 30) is adapted to provide a corresponding movement of a physical structure of the patient support apparatus 30. The user may engage the pictorial representation 176 on the user interface 110 to simulate the movement of the representation of the lever and view the corresponding result virtually on the display 112. In certain embodiments, the user, perhaps knowing the result from the simulation provided on the display 112, may subsequently elect to engage the pictorial representation 176 in a manner that provides corresponding movements of the patient support apparatus 30.

Another non-limiting example is shown in FIG. 22B with an elevational view of the patient support apparatus 30 schematically represented as the fowler section F, the seat section S, and the thigh section T. A portion of the touchscreen 113 also provides angles of inclination of the fowler section F, the seat section S, and the thigh section T relative to horizontal or another reference. The initial and final positions of the pictorial representation 176 of FIG. 22B are representative of the initial and final positions, respectively of the sections F, S, T of the patient support apparatus 30. In the initial position, the user may touch the pictorial representation 176 on the touchscreen 113 with the finger F (shown in phantom), and slides the finger F arcuately as shown. The final position of the pictorial representation 176 (shown in solid) may be interpreted by the controller 102 as the desired position of the fowler section F. The touchscreen 113 provides an input signal to the controller 102 as previously described. The controller 102 provides a corresponding signal to control the operational devices 70-90 of the patient support apparatus 30, in this example the deck adjustment device 84. The fowler section F moves in a manner corresponding to the user input to the touchscreen 113. The above example may be considered to control movement of the fowler section F to a desired deck angle by directly engaging the pictorial representation 180 of the patient support apparatus 30.

The speed with which the user slides the finger F may be associated with the speed of the corresponding movement of the patient support apparatus 30 (or component thereof). In one embodiment, the speed of the movement of the finger F may be interpreted proportionally, such as by a multiplying factor, to the speed of the corresponding movement of the patient support apparatus 30. The multiplying factor may be selected by the user with the user interface 110. Additionally or alternatively, the patient support apparatus 30 may be moved simultaneously with the virtual movement of the pictorial representation 176 if the speed of the input is suitably slow, and/or another safety mechanism is optionally in place.

In certain embodiments, the user may engage the pictorial representation 176 displayed on the touchscreen 113 to move the pictorial representation 176 to final position without initially effectuating the corresponding movement of the patient support apparatus 30. After the user is satisfied with the final position of the pictorial representation 176, the user may provide a subsequent input to the touchscreen 113 to facilitate the corresponding movement of the patient support apparatus 30. With FIG. 22B as exemplary, a button B26 ("Submit") is shown on the touchscreen 113. The user touches the touchscreen 113 with the finger F (shown in phantom), and slides the finger F arcuately as previously described. No corresponding movement of the patient support apparatus 30 occurs at this point. The user may make adjustments to the final position of the pictorial representation 176 (shown in solid) until the user is satisfied with the final position. The user selects the button B26, after which the final position of the pictorial representation 176 (shown in solid) may be interpreted by the controller 102 as the desired position of the fowler section F. The touchscreen 113 provides an input signal to the controller 102, and the controller 102 provides a corresponding signal to control the deck adjustment device 84. The fowler section F moves in a manner corresponding to the user input to the touchscreen 113. In certain embodiments, the user may preview (i.e., simulate) the movement on the touchscreen 113 before providing the subsequent input to confirm the final position. In another embodiment, the user may be required to "double click" in order to initiate the corresponding movement of the patient support apparatus 30. In still another embodiment, a "pop-up window" may be generated requesting confirmation of the final position prior to the controller 102 initiating the corresponding movement of the patient support apparatus 30. Voice confirmation may alternatively or additionally be utilized. Using a button, a pop-up window, voice confirmation, and/or similar confirmatory measures may prevent the patient support apparatus 30 from potentially erratic movements (as the user adjusts the final position of the pictorial representation 176) that may discomfort the patient supported on the same. In each of the above embodiments, adjustment may be provided before the user provides the subsequent input confirming the desired action.

The present disclosure contemplates that control of any number of operational devices 70-90 of the patient support apparatus 30 may be controlled through the touchscreen 113 displaying the pictorial representation 176 of the patient support apparatus 30. The touchscreen 113 may comprise submenus to selectively display different pictorial representations 176 of the patient support apparatus 30. FIGS. 22A and 22B each show four submenus along a bottom of the touchscreen, but any number and positioning of the submenus are contemplated. Selecting a submenu may result in one of the pictorial representations 176 of the patient support apparatus 30 being displayed that most effectively facilitates control of the operational devices 70-90 associated with the selected submenu. For example, FIG. 22A shows the submenu "Height" selected, with the lift device 78 being at least one of the operational devices 70-90 associated with the selected submenu. The touchscreen 113 displays a side elevation view such that the user optimally visualizes the relative height adjustment as the user engages the pictorial representation 176. FIG. 22B shows the submenu "Deck" selected, with the deck adjustment device 84 being at least one of the operational devices 70-90 associated with the selected submenu. The touchscreen 113 displays a side elevation view with segmented sections (i.e., the fowler section F, the seat section S, and the thigh section T) such that the user optimally visualizes the relative angular adjustment to the sections F, S, T. In another example, the touchscreen 113 displays a top plan view such that the user may control the bed length extension device 80, the bed width extension device 82, and the like.

The present disclosure further contemplates the pictorial representation 176 of the patient support apparatus 30 may be utilized in connection with the location-based user menu 144, the customized user menu 120b, 122b, 124b, the position-based user menu 134, the position-based output 142, and/or the identification-based user menu 154. In other words, the pictorial representation 176, at least as it presented to the user upon viewing the touchscreen 113 (e.g., a "home screen"), may "evolve" based on any of the aforementioned user menus. Of particular interest is the evolution of the pictorial representation 176 based on usage characteristics and user identity. It may become apparent to the controller 102, through machine-learning algorithms, that certain user profiles 162, subspecialties of those user profiles and/or individuals utilize the pictorial representation 176 to perform certain operational functions 70-90 more than others. As the caregiver, separate from the patient, is viewing the touchscreen 113, the controller 102 may update the pictorial representation 176 to zoom in on a certain part of the pictorial representation 176 that is more frequently utilized by that caregiver. Additionally or alternatively, as the caregiver is viewing the touchscreen 113, the controller 102 may update the pictorial representation 176 to provide indicia, menu buttons, pop ups, and the like, of operational functions 70-90 more frequently accessed by that caregiver. For example, if the user comprises a physical therapist that frequently adjusts the height of the patient support apparatus 30 through engaging the pictorial representation 176, the controller 102 may determine the usage characteristics over time with the usage characteristics comprising the frequency the physical therapist engages the pictorial representation 176 to control the patient raising device 70. The controller 102 determines the customized user menu based, at least in part, on the usage characteristics. At least a portion of the customized user menu may comprise the elevation view of the pictorial representation 176 to control the lift device 48. The usage characteristics may be associated with the user profile 162 of the physical therapist (see FIGS. 18 and 19) such that, when the physical therapist is within a predetermined proximity of the patient support apparatus 30, as determined by the locating system 132, the customized user menu is displayed, perhaps automatically. The physical therapist is provided with the pictorial representation 176 to control the lift device 78 without undue navigation of the various menus. The above example combines features from the customized, position-based, and identification-based user menus.

The touchscreen 113 may comprise a button B28 ("Main Menu") to direct the user to, for example, the indicia-based user menus (e.g., icons arranged in a list or grid) previously described. Providing an input to the touchscreen 113 comprising selection of the button B28 may, for example, result in transmitting an input signal to the controller 102. In response to the input signal, the controller 102 generates the updated display signal representative of the user menu 114 of, for example, FIG. 3. The controller 102 transmits the updated display signal to the touchscreen 113 to display the user menu of FIG. 3. Conversely, when the touchscreen 113 displays the indicia-based user menus (e.g., FIG. 3), the menus may comprise a submenu to display the pictorial representation 176. In such an embodiment, the user may effectively toggle between the indicia-based user menus and the pictorial representation-based user menus.

A locking feature may be incorporated to prevent inadvertent movement of the patient support apparatus 30 as the user engages the touchscreen 113. The locking feature may comprise a button B30 displayed on the touchscreen 113. FIG. 22A shows the button B30 in a locked configuration. In the locked configuration, engagement with the pictorial representation 176 may not provide any corresponding movement of the pictorial representation 176 and/or the patient support apparatus 30. In one embodiment, the user slides the finger F when the pictorial representation 176 is in the locked configuration, the pictorial representation 176 remains static and provides no corresponding movement. In another embodiment, the user slides the finger F when the pictorial representation 176 is in the locked configuration, the pictorial representation 176 provides the corresponding movement, but the patient support apparatus 30 does not provide the corresponding movement, at least until the locking button B30 is moved from the locked configuration to an unlocked configuration.

The locking feature of FIG. 22B shows two buttons B30, the first associated with the fowler section F and the other associated with the thigh section T. Any number of locking buttons may be included. The button B30 associated with the fowler section F is in the unlocked configuration such that the user may engage the touchscreen 113 to control the deck adjustment device 84 and provide a corresponding movement to the patient support apparatus 30 as previously described. The button B30 associated with the thigh section T is in the locked configuration such that engagement with the thigh section T of the pictorial representation 176 may not provide any corresponding movement of the thigh section T, either on the pictorial representation 176 or the patient support apparatus 30. The user selecting the button B30 may toggle the locking feature between the locked and unlocked configurations. Other features of the patient support system 28 utilizing the touchscreen 113 comprising the pictorial representation 176 will be readily apparent to those having skill in the art.

In certain embodiments, the user interface 110 may comprise a plurality of user interfaces 110 each disposed on different portions of the patient support apparatus 30. The plurality of user interfaces 110 may be coupled to any suitable structure of the patient support apparatus 30, including the patient support deck 38, the intermediate frame 36, the headboard 52, the footboard 54, the side rails 44, 46, 48, 50, and the like. The plurality of user interfaces 110 may be positioned at and associated with the fowler section F, the seat section S, and/or the thigh section T (see FIG. 22B). The plurality of user interfaces 110 may comprise virtual and/or tactile buttons or gesture-sensing devices. Each of the plurality of user interfaces 110 may be adapted to control one or more predefined operational functions with the portion or structure of the patient support apparatus 30 to which the user interface 110 is coupled. For example, a gesture-sensing device may be coupled to the fowler section F to control the fowler section F, to the thigh section T to control the thigh section T, and the like. The caregiver positioned proximate to make a gesture (e.g., wave of hand) detected by the gesture sensing device, and the corresponding actuator controlling positioning of the fowler section F or thigh section T is controlled, perhaps automatically. In certain embodiments, the buttons or gesture sensing devices may be devoid of an integrated or corresponding display. Providing the buttons or gesture sensing devices about the patient support apparatus 30 on the actual parts being manipulated minimizes the space required by the user interfaces 110 relative to, for example, the touchscreen 113 integrated with the display 112. Convenience is also provided to the user by removing the need to walk about the patient support apparatus 30 to the location of the touchscreen 113. The buttons or gesture sensing devices disposed at certain locations about the patient support apparatus 30 may be considered "satellite" or secondary user interfaces 110 to a primary user interface embodied on the touchscreen 113 and/or mobile device 156. The secondary user interfaces 110 may be communicated with the primary user interface so that both the secondary and primary user interfaces can be utilized in combination in some cases.

Figure 23:
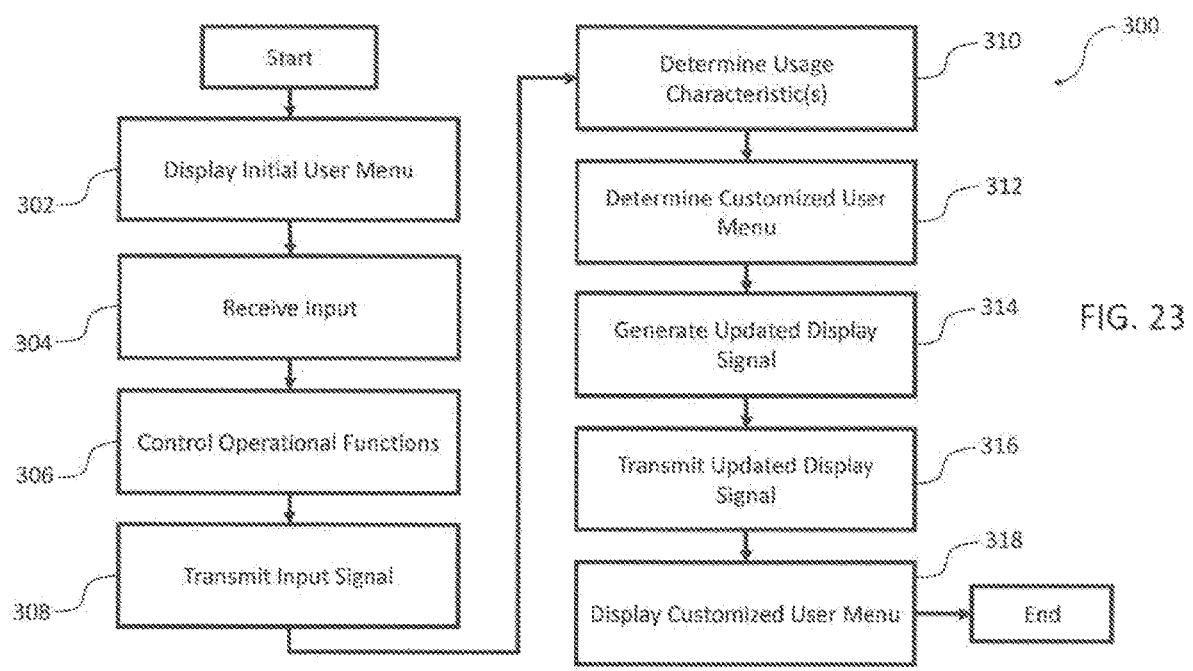
FIG. 23 is a schematic diagram detailing exemplary operation of the patient support system in accordance with certain embodiments of the present disclosure.

Exemplary methods of providing a customized user menu displayed on the display 112 are also provided. In certain embodiments, the user interface 110 is configured to receive input from the user of the patient support apparatus 30 with the controller 102 in communication with the user interface 110. The control system 100 is configured to control operational functions of the patient support apparatus 30. Referring to FIG. 23, the method 300 comprises the step of displaying (step 302) on the display 112 an initial user menu 120a comprising the indicia 116 representative of the operational functions of the patient support apparatus 30. The user interface 110 receives (step 304) the input from the user comprising a user selection of one of the indicia 116. The control system 100 controls (step 306) the operational functions of the patient support apparatus 30. An input signal is transmitted (step 308) from the user interface 110 to the controller 102 based on the user selection. Further, the method 300 comprises the step 310 of determining with the controller 102 a usage characteristic based on the input signals from the user interface 110. The controller 102 determines (step 312) the customized user menu 120b, 122b, 124b based on the usage characteristic and generates (step 314) an updated display signal representative of the customized user menu 120b, 122b, 124b. The updated display signal is transmitted (step 316) from the controller 110 to the display 112, and the display 112 displays (step 318) the customized user menu 120b, 122b, 124b.

In certain embodiments, the controller 102 updates the usage characteristic after a subsequent user selection to determine the customized user menu 120b, 122b, 124b. The customized user menu 120b, 122b, 124b may be displayed on the display 112 after updating of the usage characteristic, and/or after a predetermined number of updates of the usage characteristic. The usage characteristics may be based on an identifier associated with the user, such as a user group such that said customized user menu is common to users of the user group.

Figure 24:
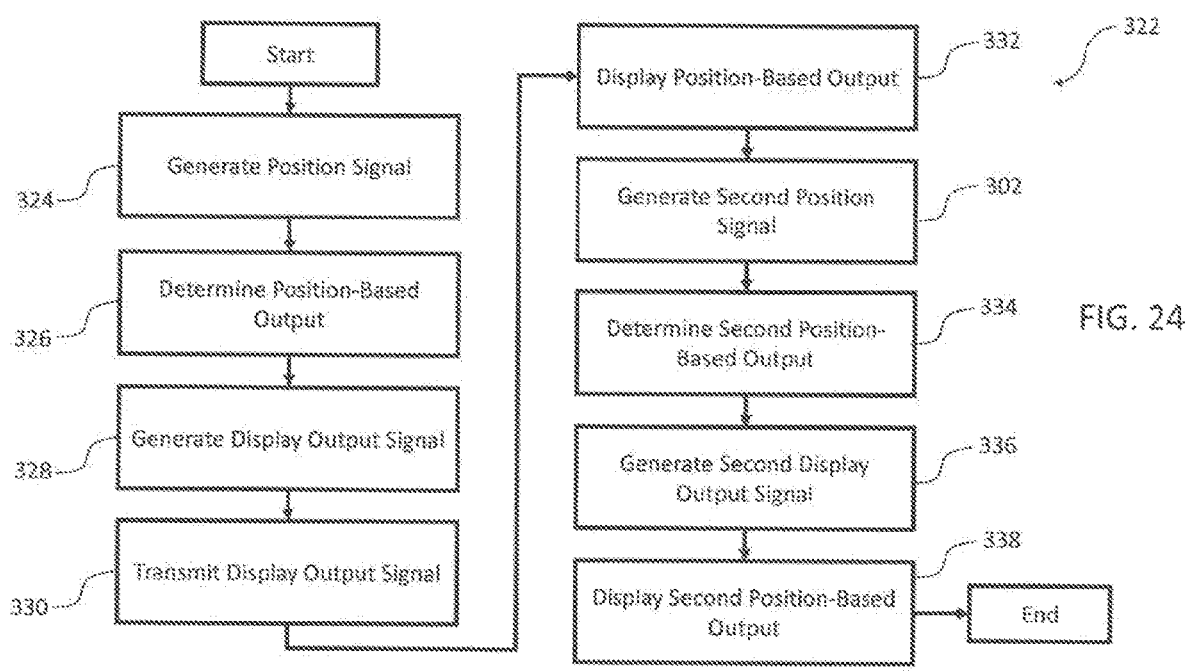
FIG. 24 is a schematic diagram detailing exemplary operation of the patient support system in accordance with certain embodiments of the present disclosure.

According to another exemplary method 322 of providing a customized user menu, the locating system 132 is configured to determine a position of the user interface 110 with respect to the patient support apparatus 30 with the controller 102 in communication with the user interface 110. Referring to FIG. 24, the method 322 comprises the step 324 of generating with the locating system 132 a first position signal based on a first position of the user interface 110 in proximity to the patient support apparatus 30. The controller 102 determines (step 326) a first position-based output based on the first position signal, and generates (step 328) a first display output signal representative of the first position-based output. The controller 102 transmits (step 330) to the display 112 a first display output signal representative of the first position-based output. The display 112 displays (step 332) the first position-based output based on the first display output signal. The locating system 132 generates (step 334) a second position signal based on a second position of the user interface 110 in proximity to the patient support apparatus with the second position being different from the first position. The method 322 further comprises the step 336 of determining with the controller 102 a second position-based output based on the second position signal. A second display output signal representative of the second position-based output is generated (step 338) and transmitted to the display 112. The second position-based output is displayed (step 340) on the display 112.

In certain embodiments, the user interface 110 is received on one of the headboard 52, the footboard 54, and the side rail, 44, 46, 48, 50, such as by removably coupling the user interface 110. The first or second position-based outputs is determined based on which one of the headboard 52, the footboard 54, and the side rail 44, 46, 48, 50, the user interface 110 is coupled. The locating system 132 may determine a distance of the user interface 110 from the patient support apparatus 32, and generate one of the first or second position signals with the locating system 132 when the distance is within a predetermined distance.

Figure 25:
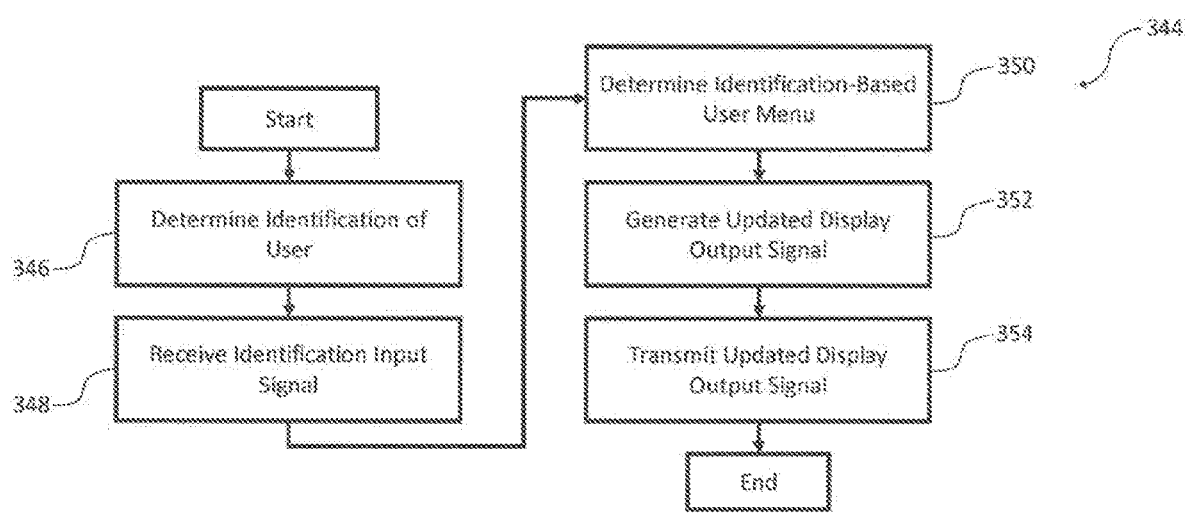
FIG. 25 is a schematic diagram detailing exemplary operation of the patient support system in accordance with certain embodiments of the present disclosure.
Figure 26:
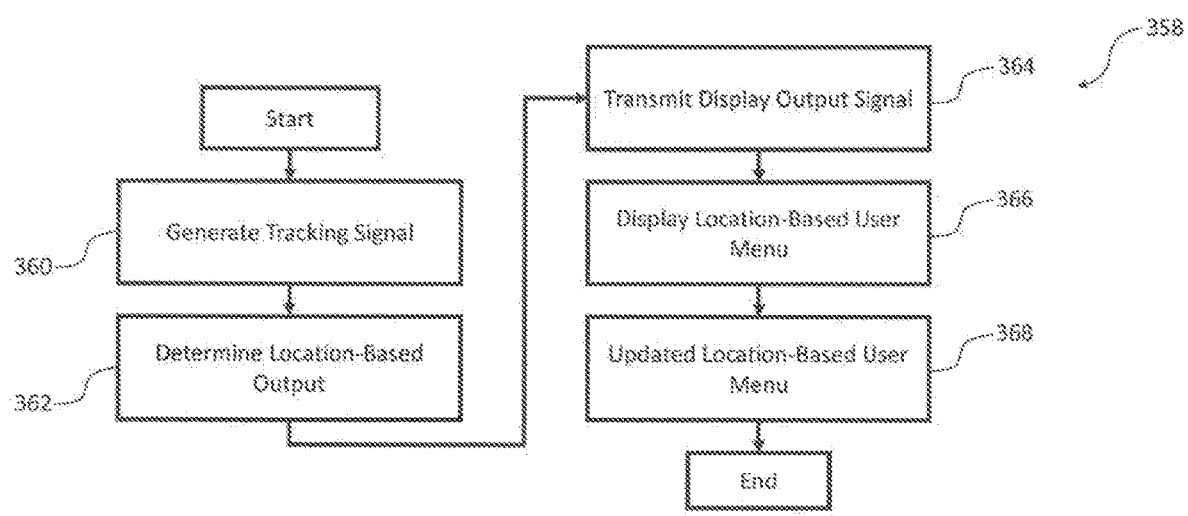
FIG. 26 is a schematic diagram detailing exemplary operation of the patient support system in accordance with certain embodiments of the present disclosure.

Referring to FIG. 25, another exemplary method 344 of providing a customized user menu includes providing the identification system 150 with the controller 102 in communication with the identification system 150. The identification system 150 determines (step 346) an identification of the user to generate and transmit an identification input signal. The controller receives (step 348) the identification input signal from the identification system, and determines (step 350) the identification-based user menu 154 based on the identification input signal. The controller 102 generates (step 352) an updated display output signal representative of the identification-based user menu 154. The controller transmits (step 354) the updated display output signal to the display 112 to display the identification-based user menu 154.

According to another exemplary method 358 of the present disclosure, the tracking system 146 is configured to determine locations of the patient support apparatus 30 within the facility 200. A tracking signal is generated (step 360) with the tracking system 146 based on a location of the patient support apparatus 30 within the facility 200. The controller 102 determines (step 362) a location-based output based on the tracking signal, and a first display output signal is transmitted (step 364) to the display 112 based on the location-based output. The location-based user menu 144 is displayed (step 366) on the display 112 based on the first display output signal. The location-based user menu 144 is updated (step 368) on the display 112 when the patient support apparatus 30 is in a second location within the facility 200 different from the first location, with the updated location-based user menu at least partially different than the location-based user menu 144.

It should be appreciated that the patient support system 28 advantageously provides customized and/or adaptive user menus/interfaces in response to various factors. In some embodiments, these same factors can be used to provide customized and/or adaptive displays, independent of any user input functionality. For example, displays mounted to any component of the patient support apparatus 30 or mobile displays may be customized or adapted in the same manner described herein for the user menus and/or user interfaces.

As noted above, the subject patent application is related to U.S. Provisional Patent Application No. 62/525,353 filed on Jun. 27, 2017. In addition, the subject patent application is also related to: U.S. Provisional Patent Application No. 62/525,359 filed on Jun. 27, 2017 and its corresponding Non-Provisional patent application Ser. No. 16/020,052 filed on Jun. 27, 2018; U.S. Provisional Patent Application No. 62/525,363 filed on Jun. 27, 2017 and its corresponding Non-Provisional patent application Ser. No. 16/020,085 filed on Jun. 27, 2018; U.S. Provisional Patent Application No. 62/525,368 filed on Jun. 27, 2017 and its corresponding Non-Provisional patent application Ser. No. 16/019,973 filed on Jun. 27, 2018; U.S. Provisional Patent Application No. 62/525,373 filed on Jun. 27, 2017 and its corresponding Non-Provisional patent application Ser. No. 16/020,003 filed on Jun. 27, 2018; and U.S. Provisional Patent Application No. 62/525,377 filed on Jun. 27, 2017 and its corresponding Non-Provisional patent application Ser. No. 16/019,986 filed on Jun. 27, 2018. The disclosures of each of the above-identified Provisional Patent Applications and corresponding Non-Provisional Patent Applications are each hereby incorporated by reference in their entirety.

It will be further appreciated that the terms "include," "includes," and "including" have the same meaning as the terms "comprise," "comprises," and "comprising."

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A patient support system comprising:
a patient support apparatus comprising a control system configured to control operational functions of said patient support apparatus;
a user interface configured to receive input from a user;
a display configured to display a user menu comprising indicia representative of said operational functions; and
a controller in communication with said user interface and said display, said controller being configured to:
receive an input signal from said user interface based on the input from the user to said user interface;
determine a usage characteristic based on said input signal from said user interface over time;
determine a customized user menu based, at least in part, on said usage characteristic and generate an updated display signal representative of said customized user menu;
transmit said updated display signal to said display to display said customized user menu; and
transmit an initial display signal to said display to display an initial user menu and receive said input signal from said user interface based on the input from the user to said user interface while displaying said initial user menu,
wherein said customized user menu comprises updated indicia different from said indicia of said initial user menu, and wherein two of said updated indicia are associated with one of said operational functions of said patient support apparatus, with a first of said two updated indicia determined by a usage characteristic based on input signals and a second of said two updated determined by association with said one operational function.

2. The patient support system of claim 1, wherein said usage characteristic comprises one of (i) a frequency the user selects one of said indicia representative of one of said operational functions, (ii) a previous user selection of one of said indicia representative of one of said operational functions, and (iii) a time of day the user selects said one of said indicia representative of one of said operational functions.

3. The patient support system of claim 1, wherein said customized user menu comprises at least one of an updated arrangement of said updated indicia different from an initial arrangement of said indicia, and an updated scaling of said updated indicia different from an initial scaling of said indicia.

4. The patient support system of claim 1, further comprising a touchscreen comprising said user interface and said display with said touchscreen being configured to provide a pictorial representation of said patient support apparatus, wherein said pictorial representation is adapted to be directly engaged by the user with said touchscreen to control said operational functions of said patient support apparatus.

5. The patient support system of claim 4, wherein said customized user menu comprises an updated rendering of said pictorial representation of said patient support apparatus based on said usage characteristics, wherein said updating rendering includes at least one of a default view of said pictorial representation, a default view of a portion of said pictorial representation, and said updated indicia.

6. The patient support system of claim 1, wherein said two updated indicia are arranged adjacent one another.

7. A patient support system comprising:
   a patient support apparatus comprising a control system configured to control operational functions of said patient support apparatus;
   a user interface configured to receive input from a user;
   a display configured to display a user menu comprising indicia representative of said operational function; and
   a controller in communication with said user interface and said display, said controller being configured to:
      transmit an initial display signal to said display to display an initial user menu;
      receive an input signal from said user interface based on the input from the user to said user interface while displaying said initial user menu;
      determine a usage characteristic based on said input signal from said user interface;
      determine a customized user menu based, at least in part, on said usage characteristic and generate an updated display signal representative of said customized user menu; and
      transmit said updated display signal to said display to display said customized user menu,
   wherein said customized user menu comprises updated indicia, and wherein a first of said updated indicia is determined by said indicia previously selected on said initial user menu and associated with one of said operational functions, and a second of said updated indicia is determined by and associated with the same one of said operational functions as said first indicia.

8. The patient support system of claim 7, wherein the association between said first and second indicia is pre-defined and programmed to said controller.

9. The patient support system of claim 7, wherein the association between said first and second indicia is based on said usage characteristics over time.

10. The patient support system of claim 7, wherein said first and second indicia are arranged adjacent to one another on said customized user menu.

* * * * *